US012758657B2

(12) United States Patent
Meyer et al.

(10) Patent No.: US 12,758,657 B2
(45) Date of Patent: Oct. 13, 2026

(54) GENE THERAPY TARGETING COCHLEAR CELLS

(71) Applicant: RESEARCH INSTITUTE AT NATIONWIDE CHILDREN'S HOSPITAL, Columbus, OH (US)

(72) Inventors: Kathrin Christine Meyer, Columbus, OH (US); Karim Bey, Nantes (FR)

(73) Assignee: RESEARCH INSTITUTE AT NATIONWIDE CHILDREN'S HOSPITAL, Columbus, OH (US)

(*) Notice: Subject to any disclaimer, the term of this patent is extended or adjusted under 35 U.S.C. 154(b) by 1129 days.

(21) Appl. No.: 17/769,952

(22) PCT Filed: Oct. 19, 2020

(86) PCT No.: PCT/US2020/056385

§ 371 (c)(1),
(2) Date: Apr. 18, 2022

(87) PCT Pub. No.: WO2021/077115

PCT Pub. Date: Apr. 22, 2021

(65) Prior Publication Data

US 2022/0378945 A1 Dec. 1, 2022

Related U.S. Application Data

(60) Provisional application No. 62/923,398, filed on Oct. 18, 2019.

(51) Int. Cl.

*A61K 48/00* (2006.01)
*A61P 27/16* (2006.01)
*C07K 14/47* (2006.01)
*C12N 15/113* (2010.01)
*C12N 15/864* (2006.01)

(52) U.S. Cl.

CPC ........ *A61K 48/0075* (2013.01); *A61K 48/005* (2013.01); *A61P 27/16* (2018.01); *C07K 14/47* (2013.01); *C12N 15/1138* (2013.01); *C12N 15/8645* (2013.01); *C12N 2310/14* (2013.01); *C12N 2310/141* (2013.01); *C12N 2750/14143* (2013.01)

(58) Field of Classification Search

CPC .............. A61K 48/0075; A61K 48/005; C12N 15/8645; C12N 2310/14; C12N 2310/141; C12N 2750/14143; A61P 27/16
USPC ......... 514/44 R, 44 A; 424/199.1, 93.6, 93.2
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 6,258,595 B1 | 7/2001 | Gao et al. | |
| 6,566,118 B1 | 5/2003 | Atkinson et al. | |
| 9,434,928 B2 | 9/2016 | Mendell et al. | |
| 2005/0053922 A1 | 3/2005 | Schaffer et al. | |
| 2006/0233755 A1 | 10/2006 | Kaneda et al. | |
| 2009/0202490 A1 | 8/2009 | Schaffer et al. | |
| 2019/0192691 A1* | 6/2019 | Barrett | C07K 14/70517 |
| 2021/0355504 A1* | 11/2021 | Burns | A61K 9/0046 |

FOREIGN PATENT DOCUMENTS

| | | |
|---|---|---|
| JP | 2018-536420 A | 12/2018 |
| WO | 95/13365 A1 | 5/1995 |
| WO | 95/13392 A1 | 5/1995 |
| WO | 96/17947 A1 | 6/1996 |
| WO | 97/06243 A1 | 2/1997 |
| WO | 97/08298 A1 | 3/1997 |
| WO | 97/09441 A2 | 3/1997 |
| WO | 97/21825 A1 | 6/1997 |
| WO | 98/09657 A2 | 3/1998 |
| WO | 99/11764 A2 | 3/1999 |
| WO | 01/83692 A2 | 11/2001 |
| WO | WO-2004/030702 A1 | 4/2004 |
| WO | 2015/054653 A2 | 4/2015 |
| WO | WO-2017/100791 A1 | 6/2017 |
| WO | 2018/039375 A1 | 3/2018 |
| WO | 2019/200016 A1 | 10/2019 |
| WO | WO2020/198737 * | 10/2020 |

OTHER PUBLICATIONS

Stover et al. (2000) Gene Ther., vol. 7, 377-383.*
Castle et al. (2018) Sci. Adv., vol. 4, eaau9859, pp. 1-10.*
Oshima et al. (2003) FASEB J., express article 10.1096/fj.03-0567fje. publishd online Nov. 20, 2003, pp. 1-21.*
Richardson et al. (2015) Exp. Opin. Biol. Ther., vol. 15(3), 417-430.*
Shibata et al. (2017) Scientific Reports, vol. 7:9609. DOI: 10.1038/s41598-017-09805-x, pp. 1-11.*
Lee et al. (2018) Biomed. Res. Int., Article ID 8137614, doi.org/10.1155/2018/8137614, pp. 1-11.*
NM_005172 *Homo sapiens* atonal bHLH transcription factor (ATOH1), mRNA, published as early as 1996.*
Ribera et al., Correction of Visual and Auditory Function by AAV9-Mediated Gene Therapy in a Mouse Model of Mucopolysaccharidosis Type IIIB, Molecular Therapy, 26(5):114 (May 2018).
Ahmed et al., Emerging Gene Therapies for Genetic Hearing Loss, J. Assoc. Res. Otolaryngol., 18(5):649-670 (2017).

(Continued)

*Primary Examiner* — Anne Marie S Wehbe
(74) *Attorney, Agent, or Firm* — MARSHALL, GERSTEIN & BORUN LLP

(57) ABSTRACT

The present disclosure relates to methods of targeting specific cell types within the cochlea using optimized gene therapy vectors. In particular, the disclosure provides gene therapy vectors to specifically target cochlear cells and methods of treating hearing impairment and hearing-loss related disorders.

6 Claims, 23 Drawing Sheets

Specification includes a Sequence Listing.

(56) References Cited

OTHER PUBLICATIONS

Akil et al., Restoration of hearing in the VGLUT3 knockout mouse using virally mediated gene therapy, Neuron., 75(2):283-93 (2012).
Askew et al., Tmc gene therapy restores auditory function in deaf mice, Sci. Transl. Med., 7(295):295ra108 (2015).
Bey et al., Efficient CNS targeting in adult mice by intrathecal infusion of single-stranded AAV9-GFP for gene therapy of neurological disorders, Gene Ther., 24(5):325-332 (2017).
Carter, Adeno-associated virus vectors, Curr. Opin., Biotechnol., 3:533-539 (1992).
Chien et al., Cochlear gene transfer mediated by adeno-associated virus: Comparison of two surgical approaches, Laryngoscope, 125(11):2557-64 (2015).
Chien et al., Gene Therapy Restores Hair Cell Stereocilia Morphology in Inner Ears of Deaf Whirler Mice, Mol. Ther., 24(1):17-25 (2016).
Choudhury et al., In Vivo Selection Yields AAV-B1 Capsid for Central Nervous System and Muscle Gene Therapy, Mol. Ther., 24(7):1247-1257 (2016).
Clark et al., A stable cell line carrying adenovirus-inducible rep and cap genes allows for infectivity titration of adeno-associated virus vectors, Gene. Therapy, 3(12):1124-1132 (1996).
Clark et al., Highly purified recombinant adeno-associated virus vectors are biologically active and free of detectable helper and wild-type viruses, Hum. Gene. Ther., 10(6):1031-1039 (1999).
De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).
Dias et al., Molecular genetics and emerging therapies for retinitis pigmentosa: Basic research and clinical perspectives, Prog Retin Eye Res., 63:107-131 (2018).
Fukui et al., Gene therapy for the inner ear, Hear Res., 297:99-105 (2013).
Gao et al., Clades of Adeno-associated viruses are widely disseminated in human tissues, J. Virol., 78(12):6381-6388 (2004).
Giles et al., Deamidation of Amino Acids on the Surface of Adeno-Associated Virus Capsids Leads to Charge Heterogeneity and Altered Vector Function, Molecular Therapy, 26(12):2848-2862 (2018).
Hermonat et al., Use of adeno-associated virus as a mammalian DNA cloning vector: transduction of neomycin resistance into mammalian tissue culture cells, Proc. Natl. Acad. Sci. U.S.A., 81(20):6466-6470 (1984).
International Application No. PCT/US2020/056385, International Preliminary Report on Patentability, mailed Apr. 28, 2022.
International Application No. PCT/US2020/056385, International Search Report and Written Opinion, mailed Feb. 22, 2021.
Landegger et al., A synthetic AAV vector enables safe and efficient gene transfer to the mammalian inner ear, Biotechnology, 35(3):280-284 (2017).
Laughlin et al., Cloning of infectious adeno-associated virus genomes in bacterial plasmids, Gene., 23(1):65-73 (1983).
Lebkowski et al., Adeno-associated virus a vector system for efficient introduction and integration of DNA into a variety of mammalian cell types, Mol. Cell. Biol., 8(10)3988-3996, (Oct. 1988).
Likhite, Therapeutic suppression of mutant SOD1 by AAV9-mediated gene therapy approach in Amyotrophic Lateral Sclerosis, Retrieved from https://etd.ohiolink.edu/pg_10?0::NO:10:P10_ETD_SUBID:100020 (2014).
Liu et al., Specific and efficient transduction of Cochlear inner hair cells with recombinant adeno-associated virus type 3 vector, Mol. Ther., 12(4):725-33 (2005).
Luebke et al., 87-98: Adenoviral and AAV-Mediated Gene Transfer to the Inner Ear: Role of Serotype, Promoter, and Viral Load on In Vivo and In Vitro Infection Efficiencies, Adv. Otorhinolaryngol., 66:87-98 (2009).
Ma et al., New molecular therapies for the treatment of hearing loss, Pharmacol. Ther., 200:190-209 (2019).
Marsic et al., Vector Design Tour de Force: Integrating Combinatorial and Rational Approaches to Derive Novel Adeno-associated Virus Variants, Molecular Therapy, 22(11):1900-1909 (2014).
Mclaughlin et al., Adeno-associated virus general transduction vectors: analysis of proviral structures, J. Virol., 62(6):1963-73 (1988).
Meyer et al., Improving single injection CSF delivery of AAV9-mediated gene therapy for SMA: a dose-response study in mice and nonhuman primates, Mol. Ther., 23(3):477-87 (2015).
Montgomery et al., Whole Mount Dissection and Immunofluorescence of the Adult Mouse Cochlea, J. Vis. Exp., (107):53561 (2016).
Mori et al., Two novel adeno-associated viruses from cynomolgus monkey: pseudotyping characterization of capsid protein, Virology, 330(2):375-383 (2004).
Muzyczka, Use of Adeno-Associated Virus as a General Transduction Vector for Mammalian Cells, Current Topics in Microbiology and Immunology, 158:97-129 (1992).
Paul et al., Increased Viral Titer Through Concentration of Viral Harvests from Retroviral Packaging Lines, Human Gene Therapy, 4(5):609-615 (1993).
Perrin et al., An experimental rabies vaccine produced with a new BHK-21 suspension cell culture process: use of serum-free medium and perfusion-reactor system, Vaccine, 13(13):1244-1250 (1995).
Polesskaya et al., Ablation of mixed lineage kinase 3 (MIK3) does not inhibit ototoxicity induced by acoustic trauma or aminoglycoside exposure, Hear Res., 270(1-2), 21-27 (2010).
Ren et al., Gene Therapy for Human Sensorineural Hearing Loss, Front. Cell. Neurosci., 13(323):1-12 (2019).
Sambrook et al., Molecular Cloning: A Laboratory Manual, 2nd Ed., Cold Spring Harbor Laboratory, (1989).
Samulski et al., Cloning of adeno-associated virus into pBR322: rescue of intact virus from the recombinant plasmid in human cells, Proc. Natl. Acad. Sci. U.S.A., 79(6):2077-2081 (1982).
Samulski et al., Helper-free stocks of recombinant adeno-associated viruses: normal integration does not require viral gene expression, J. Virol., 63(9):3822-3828 (1989).
Schenpp et al., Highly purified recombinant adeno-associated virus vectors. Preparation and quantitation, Methods Mol. Med., 69:427-443 (2002).
Senapathy et al., Molecular cloning of adeno-associated virus variant genomes and generation of infectious virus by recombination in mammalian cells, J. Biol. Chem., 259:4661-4666 (1984).
Srivastava et al., Nucleotide sequence and organization of the adeno-associated virus 2 genome, J. Virol., 45(2):555-564 (1983).
Stover et al., Transduction of the contralateral ear after adenovirus-mediated cochlear gene transfer, Gene Ther., 7(5):377-383 (2000).
Suzuki et al., Cochlear gene therapy with ancestral AAV in adult mice: Complete transduction of inner hair cells without cochlear dysfunction, Sci. Rep., 3:7:45524 (2017).
Tratschin et al., A human parvovirus, adeno-associated virus, as a eucaryotic vector: transient expression and encapsidation of the procaryotic gene for chloramphenicol acetyltransferase, Mol. Cell. Biol., 4(10):2072-2081 (1984).
Tratschin et al., Adeno-associated virus vector for high-frequency integration, expression, and rescue of genes in mammalian cells, Mol. Cell. Biol., 5(11):3251-3260 (1985).
Zinn et al., In Silico Reconstruction of the Viral Evolutionary Lineage Yields a Potent Gene Therapy Vector, Cell Reports, 12(6):1056-1068 (2015).

* cited by examiner shx2IT-LFLR cochlea

H&E of mouse cochlea

1 -- Organ of Corti

2 -- Organ of Corti (Focus 1)

3 -- Spiral Limbus

4 -- Organ of Corti

5 -- Spiral ganglion

6 -- Vestibular epithelium

GENE THERAPY TARGETING COCHLEAR CELLS

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: 54882_Seqlisting.txt; Size: 81,037 bytes; Created: Oct. 19, 2020.

FIELD

The present disclosure relates to methods of targeting specific cell types within the cochlea using optimized gene therapy vectors. In particular, the disclosure provides gene therapy vectors to specifically target cochlear cells and methods of treating hearing impairment and hearing-related disorders.

BACKGROUND

Hearing loss is a common sensory disorder worldwide, and many of pre-lingual deafness is due to genetic causes. More than 300 genetic loci linked to hereditary hearing loss and >100 causative genes have also been identified. Therefore, gene therapy is an attractive method of therapy for hearing loss. However, sensory cells of the adult mammalian cochlea lack the capacity for self-renewal and invasive methods of administration may add to the damage to these cells.

The human inner ear is a small, three-dimensionally complex, fluid-filled structure encased in the densest bone in the body and located deep in the base of skull. Acoustic energy from sound is transmitted to the fluids of the cochlea via vibrations of the tympanic membrane and ossicular chain in the middle ear, producing a traveling wave along the basilar membrane. The length of the cochlea and stiffness of the basilar membrane enables the differentiation of sound frequencies. This in turn leads to activation of mechanotransduction by hair cells, specialized sensory cells located in the organ of Corti, which turn mechanical stimulation into electrical depolarization. The electrical signal initiated by the inner hair cells (IHCs) is then processed by spiral ganglion neurons (SGNs) that make up the auditory nerve and ultimately decoded in the auditory cortex of the temporal lobe 1.

The organ of Corti includes two classes of sensory hair cells: inner hair cells (IHCs), which convert mechanical information carried by sound into electrical signals transmitted to neuronal structures, and outer hair cells (OHCs), which amplify and tune the cochlear response, a process required for complex hearing function. Other potential targets in the inner ear include spiral ganglion neurons, columnar cells of the spiral limbus, which are important for the maintenance of the adjacent tectorial membrane, and supporting cells, which have protective functions and can be triggered to transdifferentiate into hair cells up to an early neonatal stage.

The inner ear is a difficult to access fluid-filled space. There are significant physical and diffusion barriers to accessing the inner hair cells, including the blood-labyrinthine barrier, and therefore systemic delivery of therapeutic agents to the inner ear is limited. The blood-labyrinthine may slow distribution of large molecules, such as viral vectors and other gene therapy reagents. In addition, disruption of the barrier may lead to leakage of high potassium into the perilymphatic spaces that bathe the basolateral surface of hair cells and neurons can chronically depolarize these cells and lead to cell death. Further, breach of the tight junctions between endolymph and perilymph can lead to rundown of the endocochlear potential, which would reduce the driving force for sensory transduction in hair cells and therefore result in reduced cochlear sensitivity and elevated auditory thresholds. (See Ahmed et al., J Assoc Res Otolaryngol. 18(5): 649-670, 2017)

It has been hypothesized that direct access to hair cells for gene therapy may be achievable through vector injection into the cochlear duct. However, injections directly into the cochlear duct could alter the delicate high-potassium endolymph fluid in the duct and thereby disrupt the endocochlear potential, leading to damage of the sensory cells and irreversible hearing loss. The perilymph-filled spaces surrounding the cochlear duct, scala tympani and scala vestibuli can be accessed from the middle ear, either through the oval window membrane or the round window membrane (RWM). The RWM, which is the only non-bony opening into the inner ear, is relatively easily accessible in many animal models, and administration of viral vector using this route has been well tolerated (Askew et al., Sci Transl Med. 7(295):295ra108, 2015, Chien et al., Mol Ther. 24(1):17-25, 2016, Chien et al., Laryngoscope.; 125(11):2557, 201).

Viral gene therapy vectors such as adenovirus, AAV, lentivirus, herpes simplex virus I, vaccinia virus have been tested in the cochlea, and these vectors only resulted in transient or suboptimal gene transfer (Fukui & Rapheal, Hear Res. 297:99-105, 2013). Only adenovirus to date has progressed to a clinical program (Luebke et al. Adv. Otorhinolaryngol: 87-98, 2009). Previous studies of AAV serotypes in vivo inner ear injection via different routes of administration highlighted the difficulties in targeting outer hair cells (OHCs), particularly via RWM injection (Liu et al., Mol Ther. 12(4):725-33, 2005), and resulted in only partial rescue of hearing in mouse models of inherited deafness (Akil et al., Neuron. 75(2):283-93, 2012, Askew et al., Science Trans. Med. 7:295ra108, 2015; Chien et al. Mol Ther. 24(1):17-25, 2016). AAV vector Anc80L65 was shown to transduce OHC with high efficiency when administered via injection into the round window membrane (Landegger et al., Biotechnology 35(3): 280-284, 2017).

In particular, there are many difficulties for targeting gene therapy vectors to the inner hair cells within the cochlea. For example, there is a very low number of inner hair cells in the cochlea. In addition, hair cells do not proliferate and the final number of hair cells is reached early in development and the number will not increase later in life.

Currently there are no biological treatments for hearing loss. Current state-of-art treatments focus on sound amplification and implanted electrodes that stimulate the auditory nerve. These strategies offer partial recovery of function for a limited patient population but do not come close to restoring natural hearing. Thus, there is a need for development of methods of delivering gene therapy vectors to the relevant cell types in the organ of Corti in the cochlea that are not invasive or damaging to the cochlear cells.

SUMMARY

The disclosure provides gene therapy vectors that target specific cell types in the cochlea. These gene therapy vectors are useful for delivering a transgene to cells within the cochlea. The disclosure provides for methods of treating hearing loss comprising administering the gene therapy vectors using systemic delivery such as intravenous delivery, intratympanic delivery or intrathecal delivery or any other delivery method used to apply the vector directly into the cerebrospinal fluid. Gene therapy methods that target specific cells types have advantages for treating hearing loss.

The term "hearing loss" is interchangeable with the term "hearing impairment" and these terms refer to hearing determined by audiometry to be below threshold levels for normal hearing.

The disclosure provides for methods of delivering a transgene to a cochlear cell in a subject comprising administering to the subject a gene therapy vector encoding the transgene, wherein the gene therapy vector is administered to the subject using systemic delivery, such as intravenous (IV) delivery, intratympanic delivery, intrathecal delivery or any other delivery method used to apply the vector directly into the cerebrospinal fluid. For example, the disclosed methods result in delivering the transgene to cochlear cells such as inner hair cells, outer hair cells, ganglion cells, supporting cells, Deiters' cells, pillar cells and/or epithelium cells.

The disclosure also provides for methods of treating hearing-loss, such as hereditary hearing loss, age-related hearing loss, or hearing-loss related to injury or disease comprising administering to the subject a gene therapy vector encoding a transgene, wherein the gene therapy vector is administered using systemic delivery such as intravenous (IV) delivery, intratympanic delivery, intrathecal delivery or any other delivery method used to apply the vector directly into the cerebrospinal fluid. The provided methods treat hearing loss caused by genetic mutation or hearing loss caused by damage.

For example, the disclosure provides for method of treating a subject suffering from a hearing loss-related disorder such as Waardenburg syndrome (WS), Branchiootorenal spectrum disorders, Neurofibromatosis 2 (NF2), Stickler syndrome, Usher syndrome type I, Usher syndrome type II, Usher syndrome type III, Pendred syndrome, Jervell and Lange-Nielsen syndrome, Biotinidase deficiencyRefsum disease, Alport syndrome, Deafness-dystonia-optic neuronopathy syndrome, or Mohr-Tranebjaerg syndrome.

The disclosure also provides for compositions for delivering a transgene to a cochlear cell in a subject, wherein the composition comprises a gene therapy vector encoding the transgene, and wherein the composition is formulated for administration using systemic delivery, such as intravenous (IV) delivery, intratympanic delivery, intrathecal delivery or any other delivery method used to apply the vector directly into the cerebrospinal fluid. For example, the disclosed compositions deliver the transgene to cochlear cells such as inner hair cells, outer hair cells, ganglion cells, supporting cells, Deiters' cells, pillar cells and/or epithelium cells.

The disclosure also provides for composition for treating hearing-loss, such as hereditary hearing loss, age-related hearing loss, or hearing-loss related to injury or disease, wherein the composition comprises a gene therapy vector encoding a transgene, and wherein the composition is formulated for systemic delivery such as intravenous (IV) delivery, intratympanic delivery, intrathecal delivery or any other delivery method used to apply the vector directly into the cerebrospinal fluid. The provided compositions are useful for treating hearing loss caused by genetic mutation or hearing loss caused by damage.

For example, the disclosure provides for compositions for treating a subject suffering from a hearing loss-related disorder such as Waardenburg syndrome (WS), Branchiootorenal spectrum disorders, Neurofibromatosis 2 (NF2), Stickler syndrome, Usher syndrome type I, Usher syndrome type II, Usher syndrome type III, Pendred syndrome, Jervell and Lange-Nielsen syndrome, Biotinidase deficiencyRefsum disease, Alport syndrome, Deafness-dystonia-optic neuronopathy syndrome, or Mohr-Tranebjaerg syndrome.

The disclosure also provides for use of a gene therapy vector encoding a transgene for the preparation of a medicament for delivering a transgene to a cochlear cell in a subject, wherein the gene therapy encodes the transgene, and wherein the medicament is formulated for systemic delivery, such as intravenous (IV) delivery, intratympanic delivery, intrathecal delivery or any other delivery method used to apply the vector directly into the cerebrospinal fluid. For example, use of disclosed gene therapy vectors results in delivering the transgene to cochlear cells such as inner hair cells, outer hair cells, ganglion cells, supporting cells, Deiters' cells, pillar cells and epithelium cells.

The disclosure also provides use of a gene therapy vector for the preparation of a medicament for treating hearing-loss, such as hereditary hearing loss, age-related hearing loss, or hearing-loss related to injury or disease comprising administering to the subject a gene therapy vector encoding a transgene, wherein the medicament is formulated for systemic delivery such as intravenous (IV) delivery, intratympanic delivery, intrathecal delivery or any other delivery method used to apply the vector directly into the cerebrospinal fluid. For example, the disclosed gene therapy vectors may be used for preparation of a medicament for treating hearing loss caused by genetic mutation or hearing loss caused by damage.

For example, the disclosure provides for medicaments for treating a subject suffering from a hearing loss-related disorder such as Waardenburg syndrome (WS), Branchiootorenal spectrum disorders, Neurofibromatosis 2 (NF2), Stickler syndrome, Usher syndrome type I, Usher syndrome type II, Usher syndrome type III, Pendred syndrome, Jervell and Lange-Nielsen syndrome, Biotinidase deficiencyRefsum disease, Alport syndrome, Deafness-dystonia-optic neuronopathy syndrome, or Mohr-Tranebjaerg syndrome.

The disclosed methods, compositions and uses deliver any transgene of interest to a cochlear cell. The transgene is a polynucleotide sequence that encodes a polypeptide of interest or is a nucleic acid that inhibits, interferes or silences expression of a gene of interest, such as a siRNA or miRNA. Exemplary transgenes are polynucleotides that encode human atonal transcription factor (ATOH1) (Genbank Accession no. NM_005172.2; SEQ ID NO: 2), otoferlin (SEQ ID NO: 4), gap junction protein beta 2 (Genbank Accession no. NM_004004.6; SEQ ID NO:6), pendrin (SLC26A) (Genebank Accession No. XM_006716025.3; SEQ ID NO: 8), forkhead box 1 (FOXG1) (Genebank Accession No. NM_005249; SEQ ID NO: 10), activin A or Inhibin (Genebank Accession No. NM_002192; SEQ ID No: 12), follistatin (FST) (SEQ ID NO: 14), galectin-1 (Genbank Accession No. NM_002305.4; SEQ ID NO: 19) or galectin-3 (Genbank Accession No. AB006780.1; SEQ ID NO: 20). In addition, the transgenes are a wild type nucleotide sequence of a gene get out in Table 1, Table 2, Table 3, Table 4 or Table 5 herein.

In any of the disclosed methods, composition or uses, the gene therapy vector is AAV1, AAV2, AAV3, AAV4, AAV5, AAV6, AAV7, AAV8, AAV9, AAVRH10, AAVRH74, AAV11, AAV12, AAV13, AAVTT or Anc80, AAV7m8 and their derivatives.

In any of the disclosed methods, the gene therapy vector comprises the CB promoter (SEQ ID NO: 1), P546 promoter (SEQ ID NO: 16), CMV promoter (SEQ ID NO: 17 or the Myo7A promoter (SEQ ID NO: 18).

In addition, in any of the disclosed methods, compositions or uses, the gene therapy vector, composition or medicament is administered using intrathecal delivery, the subject is placed in the Trendelenburg position after administering of the gene therapy vector, composition or medicament.

DETAILED DESCRIPTION

Figure 1:
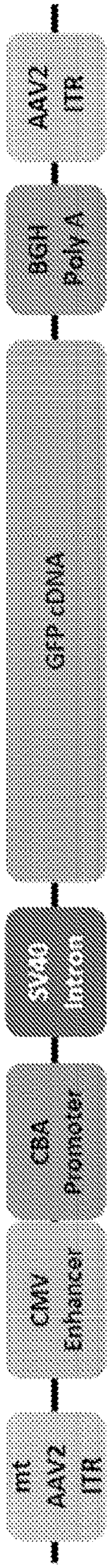
FIG. 1 provides the schematic of the AAV vector tested in this disclosure.

The disclosure provides optimization of AAV gene therapy for targeting the cochlea to treat hearing loss disorders. The data provided herein focuses on administration of AAV9 vectors, but the disclosure contemplates using any gene therapy vector that comprises a promoter that specifically targets a cochlear cell, and these optimized vectors are administered using intravenous (IV) delivery or intrathecal delivery or any other delivery method that accesses the cerebrospinal fluid (CSF). For example, the data demonstrated that AAV9 injected directly into the cerebrospinal fluid via intrathecal injection was effective in targeting transgene expression in the inner hair cells of the cochlea. Thus, intrathecal injections can be used to deliver gene therapy vectors to the cochlea and specifically for delivering gene therapy vectors to inner hair cells.

Gene Therapy Vectors

Adeno-associated virus (AAV) is a replication-deficient parvovirus, the single-stranded DNA genome of which is about 4.7 kb in length including two 145 nucleotide inverted terminal repeats (ITRs) and may be used to refer to the virus itself or derivatives thereof. The term covers all subtypes and both naturally occurring and recombinant forms, except where specified otherwise. There are multiple serotypes of AAV. The serotypes of AAV are each associated with a specific clade, the members of which share serologic and functional similarities. Thus, AAVs may also be referred to by the clade. For example, AAV9 sequences are referred to as "clade F" sequences (Gao et al., J. Virol., 78: 6381-6388 (2004). The present disclosure contemplates the use of any sequence within a specific clade, e.g., clade F. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in *Mol. Ther.,* 13(1): 67-76 (2006); the AAV-11 genome is provided in *Virology,* 330(2): 375-383 (2004); portions of the AAV-12 genome are provided in Genbank Accession No. DQ813647; portions of the AAV-13 genome are provided in Genbank Accession No. EU285562. The sequence of the AAV rh.74 genome is provided in see U.S. Pat. No. 9,434,928, incorporated herein by reference. The sequence of the AAV-B 1 genome is provided in Choudhury et al., *Mol. Ther.,* 24(7): 1247-1257 (2016). Anc80 is an AAV vector that is of AAV1, AAV2, AAV8 and AAV9. The sequence of Anc80 is provided in Zinn et al., Cell Reports 12: 1056-1068, 2015, Vandenberghe et al, PCT/US2014/060163, both of which are incorporated by reference herein, in their entirety and GenBank Accession Nos. KT235804-KT235812.

Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology,* 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The native AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. In some instances, the rep and cap proteins are provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

The term "AAV" as used herein refers to the wild type AAV virus or viral particles. The terms "AAV," "AAV virus," and "AAV viral particle" are used interchangeably herein. The term "rAAV" refers to a recombinant AAV virus or recombinant infectious, encapsulated viral particles. The terms "rAAV," "rAAV virus," and "rAAV viral particle" are used interchangeably herein.

The term "rAAV genome" refers to a polynucleotide sequence that is derived from a native AAV genome that has been modified. In some embodiments, the rAAV genome has been modified to remove the native cap and rep genes. In some embodiments, the rAAV genome comprises the endogenous 5' and 3' inverted terminal repeats (ITRs). In some embodiments, the rAAV genome comprises ITRs from an AAV serotype that is different from the AAV serotype from which the AAV genome was derived. In some embodiments, the rAAV genome comprises a transgene of interest flanked on the 5' and 3' ends by inverted terminal repeat (ITR). In some embodiments, the rAAV genome comprises a "gene cassette."

The term "scAAV" refers to a rAAV virus or rAAV viral particle comprising a self-complementary genome. The term "ssAAV" refers to a rAAV virus or rAAV viral particle comprising a single-stranded genome.

The rAAV genomes provided herein, in some embodiments, comprise one or more AAV ITRs flanking the transgene polynucleotide sequence. The transgene polynucleotide sequence is operatively linked to transcriptional control elements (including, but not limited to, promoters, enhancers and/or polyadenylation signal sequences) that are functional in target cells to form a gene cassette. Examples of promoters are the CMV promoter, chicken β actin promoter (CB), the P546 promoter and the Myo7A promoter. Additional promoters are contemplated herein including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter.

Additionally provided herein are a CMV promoter sequence, a CB promoter sequence, a P546 promoter sequence, Myo7A promoter and promoter sequences at least: 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical to the nucleotide sequence of the CMV (SEQ ID NO: 17), CB (SEQ ID NO: 1) Myo7A (SEQ ID NO: 18) or P546 (SEQ ID NO: 16) sequence which exhibit transcription promoting activity.

Other examples of transcription control elements are tissue specific control elements, for example, promoters that allow expression specifically within neurons or specifically within astrocytes. Examples include neuron specific enolase and glial fibrillary acidic protein promoters. Inducible promoters are also contemplated. Non-limiting examples of inducible promoters include, but are not limited to a metallothionine promoter, a glucocorticoid promoter, a progesterone promoter, and a tetracycline-regulated promoter. The gene cassette may also include intron sequences to facilitate processing of a transgene RNA transcript when expressed in mammalian cells. One example of such an intron is the SV40 intron.

"Packaging" refers to a series of intracellular events that result in the assembly and encapsidation of an AAV particle. The term "production" refers to the process of producing the rAAV (the infectious, encapsulated rAAV particles) by the packing cells.

AAV "rep" and "cap" genes refer to polynucleotide sequences encoding replication and encapsidation proteins, respectively, of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses may encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

The rAAV genomes provided herein lack AAV rep and cap DNA. AAV DNA in the rAAV genomes (e.g., ITRs) contemplated herein may be from any AAV serotype suitable for deriving a recombinant virus including, but not limited to, AAV serotypes Anc80, Anc80L65, AAV-1, AAV-2, AAV-3, AAV-4, AAV-5, AAV-6, AAV-7, AAV7mb, AAV-8, AAV-9, AAV-10, AAV-RH10, AAV-11, AAV-12, AAV-13, AAV rh.74 and AAV-B1 and their derivatives. As noted above, the nucleotide sequences of the genomes of various AAV serotypes are known in the art. rAAV with capsid mutations, are also contemplated. See, for example, Marsic et al., *Molecular Therapy,* 22(11): 1900-1909 (2014). Modified capsids herein are also contemplated and include capsids having various post-translational modifications such as glycosylation and deamidation. Deamidation of asparagine or glutamine side chains resulting in conversion of asparagine residues to aspartic acid or isoaspartic acid residues, and conversion of glutamine to glutamic acid or isoglutamic acid is contemplated in rAAV capsids provided herein. See, for example, Giles et al., Molecular Therapy, 26(12): 2848-2862 (2018). Modified capsids herein are also contemplated to comprise targeting sequences directing the rAAV to the affected tissues and organs requiring treatment.

DNA plasmids provided herein comprise rAAV genomes described herein. The DNA plasmids may be transferred to cells permissible for infection with a helper virus of AAV (e.g., adenovirus, E1-deleted adenovirus or herpesvirus) for assembly of the rAAV genome into infectious viral particles with AAV9 capsid proteins. Techniques to produce rAAV, in which an rAAV genome to be packaged, rep and cap genes, and helper virus functions are provided to a cell are standard in the art. Production of rAAV particles requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs. Production of pseudotyped rAAV is disclosed in, for example, WO 01/83692 which is incorporated by reference herein in its entirety. In various embodiments, AAV capsid proteins may be modified to enhance delivery of the recombinant rAAV. Modifications to capsid proteins are generally known in the art. See, for example, US 2005/0053922 and US 2009/0202490, the disclosures of which are incorporated by reference herein in their entirety.

A method of generating a packaging cell is to create a cell line that stably expresses all the necessary components for rAAV production. For example, a plasmid (or multiple plasmids) comprising a rAAV genome lacking AAV rep and cap genes, AAV rep and cap genes separate from the rAAV genome, and a selectable marker, such as a neomycin resistance gene, may be integrated into the genome of a cell. rAAV genomes may be introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line may then be infected with a helper virus such as adenovirus. The advantages of this method are that the cells are selectable and are suitable for large-scale production of rAAV. Other non-limiting examples of suitable methods employ adenovirus or baculovirus rather than plasmids to introduce rAAV genomes and/or rep and cap genes into packaging cells.

General principles of rAAV particle production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV particle production.

Further provided herein are packaging cells that produce infectious rAAV particles. In one embodiment packaging cells may be stably transformed cancer cells such as HeLa cells, 293 cells and PerC.6 cells (a cognate 293 line). In another embodiment, packaging cells may be cells that are not transformed cancer cells such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Also provided herein are rAAV (e.g., infectious encapsidated rAAV particles) comprising a rAAV genome of the disclosure. The genomes of the rAAV lack AAV rep and cap DNA, that is, there is no AAV rep or cap DNA between the ITRs of the genomes of the rAAV. The rAAV genome can be a self-complementary (sc) genome. A rAAV with a sc genome is referred to herein as a scAAV. The rAAV genome can be a single-stranded (ss) genome. A rAAV with a single-stranded genome is referred to herein as an ssAAV.

The rAAV may be purified by methods standard in the art such as by column chromatography or cesium chloride gradients. Methods for purifying rAAV from helper virus are known in the art and may include methods disclosed in, for example, Clark et al., *Hum. Gene Ther.,* 10(6): 1031-1039 (1999); Schenpp and Clark, *Methods Mol. Med.,* 69: 427-443 (2002); U.S. Pat. No. 6,566,118 and WO 98/09657.

Compositions comprising rAAV are also provided. Compositions comprise a rAAV encoding a polypeptide of interest. Compositions may include two or more rAAV encoding different polypeptides of interest. In some embodiments, the rAAV is scAAV or ssAAV.

Compositions provided herein comprise rAAV and a pharmaceutically acceptable excipient or excipients. Acceptable excipients are nontoxic to recipients and are preferably inert at the dosages and concentrations employed, and include, but are not limited to, buffers such as phosphate e.g., phosphate-buffered saline (PBS), citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, copolymers such as poloxamer 188, pluronics (e.g., Pluronic F68) or polyethylene glycol (PEG). Compositions provided herein can comprise a pharmaceutically acceptable aqueous excipient containing a non-ionic, low-osmolar compound or contrast agent such as iobitridol, iohexol, iomeprol, iopamidol, iopentol, iopromide, ioversol, or ioxilan, where the aqueous excipient containing the non-ionic, low-osmolar compound can have one or more of the following characteristics: about 180 mgl/mL, an osmolality by vapor-pressure osmometry of about 322 mOsm/kg water, an osmolarity of about 273 mOsm/L, an absolute viscosity of about 2.3 cp at 20° C. and about 1.5 cp at 37° C., and a specific gravity of about 1.164 at 37° C. Exemplary compositions comprise about 20 to 40% non-ionic, low-osmolar compound or about 25% to about 35% non-ionic, low-osmolar compound. An exemplary composition comprises scAAV or rAAV viral particles formulated in 20 mM Tris (pH8.0), 1 mM $MgCl_2$, 200 mM NaCl, 0.001% poloxamer 188 and about 25% to about 35% non-ionic, low-osmolar compound. Another exemplary composition comprises scAAV formulated in and 1×PBS and 0.001% Pluronic F68.

Dosages may be expressed in units of viral genomes (vg). Dosages contemplated herein include about $1\times10^7$ vg, about $1\times10^8$ vg, about $1\times10^9$ vg, about $5\times10^9$ vg, about $6\times10^9$ vg, about $7\times10^9$ vg, about $8\times10^9$ vg, about $9\times10^9$ vg, about $1\times10^{10}$ vg, about $2\times10^{10}$ vg, about $3\times10^{10}$ vg, about $4\times10^{10}$ vg, about $5\times10^{10}$ vg, about $1\times10^{11}$ vg, about $1.1\times10^{11}$ vg, about $1.2\times10^{11}$ vg, about $1.3\times10^{11}$ vg, about $1.2\times10^{11}$ vg, about $1.3\times10^{11}$ vg, about $1.4\times10^{11}$ vg, about $1.5\times10^{11}$ vg, about $1.6\times10^{11}$ vg, about $1.7\times10^{11}$ vg, about $1.8\times10^{11}$ vg, about $1.9\times10^{11}$ vg, about 2x10" vg, about $3\times10^{11}$ vg, about $4\times10^{11}$ vg, about $5\times10^{11}$ vg, about $1\times10^{12}$ vg, about $1\times10^{13}$ vg, about $1.1\times10^{13}$ vg, about $1.2\times10^{13}$ vg, about $1.3\times10^{13}$ vg, about $1.5\times10^{13}$ vg, about $2\times10^{13}$ vg, about $2.5\times10^{13}$ vg, about $3\times10^{13}$ vg, about $3.5\times10^{13}$ vg, about $4\times10^{13}$ vg, about $4.5\times10^{13}$ vg, about $5\times10^{13}$ vg, about $6\times10^{13}$ vg, about $1\times10^{14}$ vg, about $2\times10^{14}$ vg, about $3\times10^{14}$ vg, about $4\times10^{14}$ vg, about $5\times10^{14}$ vg, about $1\times10^{15}$ vg, to about $1\times10^{16}$ vg, or more total viral genomes. Dosages of about $1\times10^9$ vg to about $1\times10^{10}$ vg, about $5\times10^9$ vg to about $5\times10^{10}$ vg, about $1\times10^{10}$ vg to about $1\times10^{11}$ vg, about $1\times10^{11}$ vg to about $1\times10^{15}$ vg, about $1\times10^{12}$ vg to about $1\times10^{15}$ vg, about $1\times10^{12}$ vg to about $1\times10^{14}$ vg, about $1\times10^{13}$ vg to about $6\times10^{14}$ vg, and about $6\times10^{13}$ vg to about $1.0\times10^{14}$ vg, $2.0\times10^{14}$ vg, $3.0\times10^{14}$ vg, $5.0\times10^{14}$ are also contemplated. One dose exemplified herein is $1.65\times10^{11}$ vg.

Methods of transducing target cochlear cells with rAAV are provided. The cochear cells include inner hair cells, outer hair cells, ganglion cells, supporting cells, Deiters' cells, pillar cells and epithelium cells.

The term "transduction" is used to refer to the administration/delivery of the CLN6 polynucleotide to a target cell either in vivo or in vitro, via a replication-deficient rAAV of the disclosure resulting in expression of a functional polypeptide by the recipient cell. Transduction of cells with rAAV of the disclosure results in sustained expression of polypeptide or RNA encoded by the rAAV. The present disclosure thus provides methods of administering/delivering to a subject rAAV encoding a transgene encoded polypeptide by an intrathecal or IV delivery, or any combination thereof. Intrathecal delivery refers to delivery into the space under the arachnoid membrane of the brain or spinal cord. In some embodiments, intrathecal administration is via intracisternal administration.

Disorders Related to Hearing Loss

The disclosure provides methods of treating hearing loss. Conductive hearing loss results from abnormalities of the external ear and/or the ossicles of the middle ear. Sensorineural hearing loss results from malfunction of inner ear structures (i.e., cochlea or auditory nerve). Mixed hearing loss is a combination of conductive and sensorineural hearing loss. Central auditory dysfunction results from damage or dysfunction at the level of the eighth cranial nerve, auditory brain stem, or cerebral cortex.

Genetic hearing loss is subcategorized into Mendelian inheritance including both syndromic and non-syndromic cases, or complex inheritance which includes both genetic and environmental factors. A summary of the genetic causes of syndromic hearing loss are provided in Table 1. A summary of the genetic causes of nonsydromic hearing loss are provided in Table 2 and Table 3. A summary of the X-linked nonsyndromic hearing Loss is provided in Table 4 (See Shearer A E, Hildebrand M S, Smith R J H. Hereditary Hearing Loss and Deafness Overview. 1999 Feb. 14 [Updated 2017 Jul. 27]. In: Adam M P, Ardinger H H, Pagon R A, et al., editors. GeneReviews® [Internet]. Seattle (WA): University of Washington, Seattle; 1993-2019.)

TABLE 1

| Syndrome | Mode of Inheritance | Genes | Hearing Impairment Type | Onset | Severity |
|---|---|---|---|---|---|
| Waardenburg syndrome (WS) | Autosomal Dominant | PAX3<br>MITF<br>EDNRB<br>EDN3<br>SOX10 | WS1: sensorineural | Congenital | Variable |
| Branchiootorenal spectrum disorders | Autosomal Dominant | EYA1<br>SIX1<br>SIX5 | Conductive; sensorineural; mixed | Variable | Variable |
| Neurofibromatosis 2 (NF2) | Autosomal Dominant | NF2 | sensorineural | ~3rd decade | Generally unilateral & gradual; can be bilateral & sudden |
| Stickler syndrome | Autosomal Dominant | COL2A1<br>COL11A1<br>COL11A2<br>COL9A1<br>COL9A2<br>COL9A3 | Conductive, sensorineural | Variable | Variable |
| Usher syndrome type I | Autosomal Recessive | MYO7A<br>USH1C<br>CDH23<br>PCDH15<br>USH1G<br>CIB2 | sensorineural | Congenital | Severe to profound |
| Usher syndrome type II | Autosomal Recessive | ADGRV1<br>WHRN<br>USH2A | sensorineural | Congenital | Mild to severe |
| Usher syndrome type III | Autosomal Recessive | CLRN1<br>HARS1 | sensorineural | Congenital | Progressive |
| Pendred syndrome | Autosomal Recessive | SLC26A4 | sensorineural | Congenital | Usually (but not invariably) severe to profound |
| Jervell and Lange-Nielsen syndrome | Autosomal Recessive | KCNQ1<br>KCNE1 | sensorineural | Congenital | Profound Severe; progressive |
| Biotinidase deficiency | Autosomal Recessive | BTD | sensorineural | Variable | Variable |
| Refsum disease | Autosomal Recessive | PHYH<br>PEX7 | sensorineural | Variable | severity; progressive |
| Alport syndrome | X-linked (85%)<br>Autosomal Recessive (15%) | COL4A5<br>COL4A3 [7]<br>COL4A4 | sensorineural | After age 10 | Varying severity; progressive |
| Deafness-dystonia-optic neuronopathy syndrome (Mohr-Tranebjaerg syndrome) | X-linked | TIMM8A | sensorineural | Early childhood | Progressive; pre- or postlingual |

TABLE 2

| Autosomal Dominant Nonsydromic Hearing Loss: | | | |
|---|---|---|---|
| Gene | Locus | Onset/Decade | Audioprofile |
| ACTG1 | DFNA20/26 | Postlingual | High frequency; progressive |
| CCDC50 | DFNA440 | Postlingual | Low to mild frequencies; progressive |
| CD164 | DFNA66 | Postlingual | Flat or mid-frequency; progressive |
| CEACAM16 | DFNA4B | Postlingual | Flat; progressive |
| COCH | DFNA9 | Postlingual/2nd | High frequency; progressive |
| COL11A2 | DFNA13 | Postlingual/2nd | Mid-frequency loss |
| GSDME | DFNA5 | Postlingual/1st | High frequency; progressive |
| DIAPH1 | DFNA1 | Postlingual/1st | Low frequency; progressive |
| DMXL2 | — | Postlingual/2nd | Flat; progressive |
| DSPP | DFNA39 | Postlingual | High frequency; progressive |
| EYA4 | DFNA10 | Postlingual/3rd, 4th | Flat/gently downsloping |
| GJB2 [1] | DFNA3 | Prelingual | High frequency; progressive |
| GJB3 | DFNA2B | Postlingual/4th | High frequency; progressive |
| GJB6 [1] | DFNA3 | Prelingual | High frequency; progressive |
| GRHL2 | DFNA28 | Postlingual | Flat/gently downsloping |
| HOMER2 | DFNA68 | Postlingual/1st | High frequency; progressive |
| KCNQ4 | DFNA2 | Postlingual/2nd | High frequency; progressive |
| MIR96 | DFNA50 | Postlingual/2nd | Flat; progressive |
| MCM2 | DFNA70 | Postlingual | High frequency; progressive |

TABLE 2-continued

| Autosomal Dominant Nonsydromic Hearing Loss: | | | |
|---|---|---|---|
| Gene | Locus | Onset/Decade | Audioprofile |
| MYH14 | DFNA4 | Postlingual | Flat/gently downsloping |
| MYH9 | DFNA17 | Postlingual | High frequency; progressive |
| MYO1A | DFNA48 | Postlingual | Progressive |
| MYO6 | DFNA22 | Postlingual | High frequency; progressive |
| MYO7A [2] | DFNA11 | Postlingual/1st | Flat/gently downsloping |
| OSBPL2 | DFNA67 | Postlingual | High frequency; progressive |
| P2RX2 | DFNA41 | Postlingual | Flat; progressive |
| POU4F3 | DFNA15 | Postlingual | High frequency; progressive |
| SIX1 | DFNA23 | Prelingual | Downsloping |
| SLC17A8 | DFNA25 | Postlingual/2nd-6th | High frequency; progressive |
| TBC1D24 | DFNA65 | Postlingual | High frequency; progressive |
| TECTA [3, 4] | DFNA8/12 | Prelingual | Mid-frequency loss |
| TJP2 & FAM189A2 | DFNA51 | Postlingual/4th | High frequency; progressive |
| TMC1 | DFNA36 | Postlingual | Flat/gently downsloping |
| WFS1 [5] | DFNA6/14/38 | Prelingual | Low frequency; progressive |

TABLE 3

| Autosomal Recessive Nonsyndromic Hearing Loss | | | |
|---|---|---|---|
| Gene | Locus | Onset | Type |
| ADCY1 | DFNB44 | Prelingual | Mild to moderate; stable |
| BDP1 | DFNB49 | Postlingual | High frequency; stable |
| BSND | DFNB73 | Prelingual | Severe to profound; stable |
| CABP2 | DFNB93 | Prelingual | Moderate to severe; stable |
| CDC14A | DFNB105 | Prelingual | Severe to profound |
| CDH23 [1] | DFNB12 | Prelingual | Severe to profound; stable |
| CIB2 | DFNB48 | Prelingual | Severe to profound |
| CLDN14 | DFNB29 | Prelingual | Severe to profound; stable |
| CLIC5 | DFNB103 | Prelingual | High frequency; progressive |
| COL11A2 | DFNB53 | Prelingual | Severe to profound; stable |
| DCDC2 | DFNB66 | Prelingual | Severe to profound |
| PJVK | DFNB59 | Prelingual | Severe to profound; stable |
| ELMOD3 | DFNB88 | Prelingual | Severe to profound; mixed |
| EPS8 | DFNB102 | Prelingual | Severe to profound |
| EPS8L2 | — | Postlingual | High frequency; progressive |
| ESPN | DFNB36 | Prelingual | — |
| ESRRB | DFNB35 | Unknown | Severe to profound |
| GIPC3 [2] | DFNB15/72/95 | Prelingual | Severe to profound |
| GJB2 [3] | DFNB1 | Prelingual [4] | Usually stable |
| GJB6 [3] | DFNB1 | Prelingual [4] | Usually stable |
| GPSM2 | DFNB32/82 | Prelingual | Severe to profound; stable |
| GRXCR1 | DFNB25 | Prelingual | Moderate to profound; progressive |
| GRXCR2 | DFNB101 | Prelingual | High frequency; progressive |
| HGF | DFNB39 | Prelingual | Severe to profound; downsloping |
| ILDR1 | DFNB42 | Prelingual | Moderate to severe |
| KARS1 | DFNB89 | Prelingual | Moderate to severe; stable |
| LHFPL5 | DFNB67 | Prelingual | Severe to profound; stable |
| LOXHD1 | DFNB77 | Postlingual | Moderate to profound; progressive |
| LRTOMT | DFNB63 | Prelingual | Severe to profound; stable |
| MARVELD2 | DFNB49 | Prelingual | Moderate to profound; stable |
| MET | DFNB97 | Prelingual | Severe to profound |
| MSRB3 | DFNB74 | Prelingual | Severe to profound |
| MYO15A | DFNB3 | Prelingual | Severe to profound; stable |
| MYO3A | DFNB30 | Prelingual | Severe to profound; stable |
| MYO6 | DFNB37 | Prelingual | — |
| MYO7A [5] | DFNB2 | Prelingual, postlingual | Unspecified |
| NARS2 [6] | DFNB94 | Prelingual | Severe to profound; stable |
| OTOG | DFNB18B | Prelingual | Mild to moderate; stable |
| OTOGL | DFNB84 | Prelingual | High frequency; stable |
| OTOA | DFNB22 | Prelingual | Severe to profound; stable |
| OTOF | DFNB9 | Prelingual | Usually severe to profound; stable |
| PCDH15 | DFNB23 | Prelingual | Severe to profound; stable |
| PNPT1 | DFNB70 | Prelingual | Severe to profound; stable |
| PTPRQ | DFNB84 | Prelingual | Moderate to profound; progressive |
| RDX | DFNB24 | Prelingual | Severe to profound; stable |
| RIPOR2 | DFNB104 | Prelingual | Severe to profound |
| ROR1 [7] | — | Prelingual | Severe to profound |
| S1PR2 | DFNB68 | Prelingual | Severe to profound |
| SERPINB6 | DFNB91 | Prelingual | Moderate to severe |
| SLC22A4 | DFNB60 | Prelingual | Severe to profound |

TABLE 3-continued

| Autosomal Recessive Nonsyndromic Hearing Loss | | | |
|---|---|---|---|
| Gene | Locus | Onset | Type |
| SLC26A4 [8] | DFNB4 | Prelingual, postlingual | Stable; progressive |
| SLC26A5 | DFNB61 | Prelingual | Severe to profound; stable |
| STRC | DFNB16 | Prelingual | Severe to profound; stable |
| SYNE4 | DFNB76 | Prelingual | High frequency; progressive |
| TECTA [9, 10] | DFNB21 | Prelingual | Severe to profound; stable |
| TBC1D24 | DFNB86 | Prelingual | Severe to profound |
| TMC1 | DFNB7/11 | Prelingual | Severe to profound; stable |
| TMEM132E | DFNB99 | Prelingual | Severe to profound |
| TMIE | DFNB6 | Prelingual | Severe to profound; stable |
| TMPRSS3 | DFNB8/10 | Postlingual [11], prelingual | Progressive; stable |
| TPRN | DFNB79 | Prelingual | Severe to profound; stable |
| TRIOBP | DFNB28 | Prelingual | Severe to profound; stable |
| TSPEAR | DFNB98 | Prelingual | Severe to profound |
| USH1C [12] | DFNB18 | Prelingual | Severe to profound; stable |
| WBP2 | — | Prelingual | High frequency; progressive |
| WHRN | DFNB31 | Prelingual | — |

TABLE 4

| X-linked Nonsyndromic Hearing Loss: | | | | |
|---|---|---|---|---|
| Gene | Locus | Onset | Type/Degree | Frequencies |
| PRPS1 | DFNX1 | Postlingual | Progressive sensorineural/severe to profound | All |
| POU3F4 | DFNX2 | Prelingual | Progressive, mixed/variable, but progresses to profound | All |
| SMPX | DFNX4 | Postlingual | Progressive sensorineural/mild to profound | All |
| AIFM1 | DFNX5 | Prelingual | Progressive auditory neuropathy | Low frequency |
| COL4A6 | DFNX6 | Prelingual | Progressive sensorineural/severe to profound | All |

Mitochondrial DNA pathogenic variants have been implicated in a variety of diseases with hearing loss ranging from rare neuromuscular syndromes such as Kearns-Sayre syndrome, mitochondrial encephalomyopathy with lactic acidosis and stroke-like episodes (MELAS), myoclonic epilepsy with ragged-red fibers (MERRF), and neurogenic weakness with ataxia and retinitis pigmentosa (NARP), to common conditions such as diabetes mellitus, Parkinson disease, and Alzheimer disease. For examples. An exemplary pathogenic variant associated with hearing loss in diabetes mellius patients is the 3243 A-to-G transition in MTTL1 and MELAS. A summary of mitochondrial DNA mutations related to hearing loss is provided in Table 5. (See Shearer A E, Hildebrand M S, Smith R J H. Hereditary Hearing Loss and Deafness Overview. 1999 Feb. 14 [Updated 2017 Jul. 27]. In: Adam M P, Ardinger H H, Pagon R A, et al., editors. GeneReviews® [Internet]. Seattle (WA): University of Washington, Seattle; 1993-2019.)

TABLE 5

| Gene | Pathogenic Variant | Severity | Penetrance |
|---|---|---|---|
| MT-RNR1 | 961 different variants | Variable | Highly variable, aminoglycoside induced |
| | 1494C > T | Variable | |
| | 1555A > G | Variable | |
| MT-TS1 | 7445A > G | Variable | Highly variable |
| | 7472insC | Variable | |
| | 7510T > C | Variable | |
| | 7511T | Variable | |

TABLE 5-continued

| Gene | Pathogenic Variant | Severity | Penetrance |
|---|---|---|---|
| MT-CO1 | 7444G > A | Severe to profound | Complete, aminoglycoside associated; associated with MT-RNR1 1555A > G |

In any of the disclosed methods, the step of treating hearing-loss in a subject in need results in improved hearing in the subject or an improvement or reduction in hearing impairment in the subject. Tests for determining whether a method of treatment described herein improves or reduces hearing loss or hearing impairment include physiological tests which objectively determine the functional status of the auditory system; and audiometry which subjectively determines how the individual processes auditory information. Physiological tests include the auditory brain stem response testing (ABR, also known as BAER, BSER), which uses a stimulus (e.g. clicks) to evoke electrophysiologic responses, which originate in the eighth cranial nerve and auditory brain stem and are recorded with surface electrodes. ABR “wave V detection threshold” correlates best with hearing sensitivity in the 1500- to 4000-Hz region in neurologically normal individuals; ABR does not assess low frequency (<1500 Hz) sensitivity.

Auditory steady-state response testing (ASSR) uses an objective, statistics-based mathematical detection algorithm to detect and define hearing thresholds. ASSR can be obtained using broadband or frequency-specific stimuli and can offer hearing threshold differentiation in the severe-to-profound range. The ASSR test is frequently used to give frequency-specific information that ABR does not give. Test frequencies of 500, 1000, 2000, and 4000 Hz are commonly used.

Evoked otoacoustic emissions (EOAEs) are sounds originating within the cochlea that are measured in the external auditory canal using a probe with a microphone and transducer. EOAEs reflect primarily the activity of the outer hair cells of the cochlea across a broad frequency range and are present in ears with hearing sensitivity better than 40-50 dB HL. Immittance testing (tympanometry, acoustic reflex thresholds, acoustic reflex decay) assesses the peripheral auditory system, including middle ear pressure, tympanic membrane mobility, Eustachian tube function, and mobility of the middle ear ossicles.

Audiometry includes behavioral tests such as behavioral observation audiometry (BOA) and visual reinforcement audiometry (VRA). Pure-tone audiometry (air and bone conduction) involves determination of the lowest intensity at which an individual "hears" a pure tone, as a function of frequency (or pitch). Octave frequencies from 250 (close to middle C) to 8000 Hz are tested using earphones. Intensity or loudness is measured in decibels (dB), defined as the ratio between two sound pressures. 0 dB HL is the average threshold for a normal hearing adult; 120 dB HL is so loud as to cause pain. Speech reception thresholds (SRTs) and speech discrimination are assessed. For air conduction audiometry sounds are presented through earphones; thresholds depend on the condition of the external ear canal, middle ear, and inner ear. For bone conduction audiometry sounds are presented through a vibrator placed on the mastoid bone or forehead, thus bypassing the external and middle ears; thresholds depend on the condition of the inner ear. Additional tests include conditioned play audiometry which develops a complete frequency-specific audiogram for each ear, and conventional audiometry which indicates when an individual hears a sound.

An audioprofile refers to the recording of several audiograms on a single graph. These audiograms may be from one individual at different times, but more frequently they are from different members of the same family segregating deafness usually in an autosomal dominant fashion. By plotting numerous audiograms with age on the same graph, the age-related progression of hearing loss can be appreciated within these families.

Transgenes

The disclosed methods comprising delivering any transgene of interest to a cochlear cell. The transgene is a polynucleotide sequence that encodes a polypeptide of interest or is a nucleic acid that inhibits, interferes or silences expression of a gene of interest, such as a siRNA or miRNA. Exemplary transgenes are the human atonal transcription factor (ATOH1) cDNA (SEQ ID NO: 2), otoferlin cDNA (SEQ ID NO: 4), gap junction protein beta 2 (GJB2) cDNA (SEQ ID NO: 6), SLC264 cDNA (SEQ ID NO: 8), Forkhead Box 03 (FOXO3) cDNA (SEQ ID NO: 10), Activin A cDNA (SEQ ID NO: 12), follistatin cDNA (SEQ ID NO: 14).

Exemplary transgenes are polynucleotides that encode human atonal transcription factor (SEQ ID NO: 3), otoferlin (SEQ ID NO: 5), gap junction protein beta 2 (SEQ ID NO: 7), pendrin (SEQ ID NO: 9), forkhead box 1 (SEQ ID NO: 11), activin A or inhibin (SEQ ID No: 13), follistatin (SEQ ID NO: 15) galectin-1 (SEQ ID NO: 20) and galectin-3 (SEQ ID NO: 22) proteins.

miRNA shRNA and miRNA, that are expressed in the cochlea, are contemplated as transgenes to include in the disclosed optimized gene therapy vectors.

rAAV genomes provided herein may comprise a wild type nucleic acid sequence of any of the genes provided in Table 1, Table 2, Table 3, Table 4 or Table 5 herein. In addition, rAAV genomes provided herein may comprise a cDNA sequence of one of the following human atonal transcription factor (ATOH1) cDNA (SEQ ID NO: 2), otoferlin cDNA (SEQ ID NO: 4), gap junction protein beta 2 (GJB2) cDNA (SEQ ID NO: 6), SLC264 cDNA (SEQ ID NO: 8), forkhead Box 1 (FOXO3) cDNA (SEQ ID NO: 10), activin A cDNA (SEQ ID NO: 12), follistatin (SEQ ID NO: 14), galectin-1 (SEQ ID NO: 19) or galectin-3 (SEQ ID NO: 21) cDNA. For example, the polypeptide encoded by the transgene include polypeptides comprising an amino acid sequence that is at least: 90%, 91%, 92%, 93%, 94%, 95%, 96%, 97%, 98%, or 99% identical to the amino acid sequence encoded by the transgene sequence, and retains the desired activity.

For example, rAAV genomes provided herein comprise a polynucleotide encoding a human atonal transcription factor (SEQ ID NO: 3), otoferlin (SEQ ID NO: 5), gap junction protein beta 2 (SEQ ID NO: 7), pendrin (SEQ ID NO: 9), forkhead box 1 (SEQ ID NO: 11), activin A or inhibin (SEQ ID NO: 13), follistatin (SEQ ID NO: 15), galectin-1 (SEQ ID NO: 20) or galectin-3 (SEQ ID NO: 22). The polypeptide include polypeptides comprising an amino acid sequence that is at least: 90%, 91%, 92%, 93%, 94%, 95%, 96%, 97%, 98%, or 99% identical to an amino acid sequence encoded by the transgene sequence and retains the desired activity.

rAAV genomes provided herein, in some cases, comprise a polynucleotide encoding a polypeptide or a polynucleotide at least: 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical to the nucleotide sequence that encodes a polypeptide with the desired activity.

rAAV genomes provided herein, in some embodiments, comprise a transgene comprising a polynucleotide sequence that encodes a polypeptide with a desired activity and that hybridizes under stringent conditions to any one of nucleic acid sequence of a known transgene of interest, or the complement thereof.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing include but are not limited to 0.015 M sodium chloride, 0.0015 M sodium citrate at 65-68° C. or 0.015 M sodium chloride, 0.0015M sodium citrate, and 50% formamide at 42° C. See, for example, Sambrook et al., Molecular Cloning: A Laboratory Manual, 2nd Ed., Cold Spring Harbor Laboratory, (Cold Spring Harbor, N.Y. 1989).

Methods of Administration

Intrathecal administration is exemplified herein. These methods include transducing target cells with one or more rAAV described herein. In some embodiments, the rAAV viral particle comprising a transgene is administered or delivered to the ear, brain and/or spinal cord of a patient. In some embodiments, the polynucleotide is delivered to the brain. Areas of the brain contemplated for delivery include, but are not limited to, the motor cortex, visual cortex, cerebellum and the brain stem. In some embodiments, the polynucleotide is delivered to the spinal cord. In some embodiments, the polynucleotide is delivered to a lower motor neuron. The polynucleotide may be delivered to a cochlear cell such as inner hair cells, outer hair cells, ganglion cells, supporting cells, Deiters' cells, pillar cells and epithelium cells.

In some embodiments of methods provided herein, the patient is held in the Trendelenberg position (head down position) after administration of the rAAV (e.g., for about 5, about 10, about 15 or about 20 minutes). For example, the patient may be tilted in the head down position at about 1 degree to about 30 degrees, about 15 to about 30 degrees, about 30 to about 60 degrees, about 60 to about 90 degrees, or about 90 to about 180 degrees).

For intracerebroventicular injections, a needle is inserted into the skull and the liquid is injected into the ventricles containing cerebrospinal fluid. For example, intracerebroventicular injections are carried out by a clinically trained surgeon using methods known in the art.

The methods provided herein comprise the step of administering an effective dose, or effective multiple doses, of a composition comprising a rAAV provided herein to a subject (e.g., an animal including, but not limited to, a human patient) in need thereof. If the dose is administered prior to development of the symptoms of the hearing loss-related disorder, the administration is prophylactic. If the dose is administered after the development of symptoms of the hear loss-related disorder, the administration is therapeutic. An effective dose is a dose that alleviates (eliminates or reduces) at least one symptom associated with the hearing loss-related disorder, that slows or prevents progression of the disorder, that diminishes the extent of disorder, that results in remission (partial or total) of disorder, and/or that prolongs hearing and/or survival. In comparison to the subject before treatment or in comparison to an untreated subject, methods provided herein result in stabilization, reduced progression of hearing loss, or improvement in hearing.

EXAMPLES

While the following examples describe specific embodiments, it is understood that variations and modifications will occur to those skilled in the art. Accordingly, only such limitations as appear in the claims should be placed on the invention.

Example 1

Production of scAAV9.GFP

A human GFP cDNA clone was obtained from Origene, Rockville, MD. GFP cDNA alone or GFP cDNA and shSOD-1 cDNA was further subcloned into a self-complementary AAV9 genome under the hybrid chicken (3-Actin promoter (CB). The plasmid construct also included one or more of the CB promoter (SEQ ID NO: 1), an intron such as the simianvirus 40 (SV40) chimeric intron and a Bovine Growth Hormone (BGH) polyadenylation signal (BGH PolyA). A schematic of the plasmid constructs showing the GFP cDNA inserted between AAV2 ITRs is provided in FIG. 1 referred to as AAV9.CB.GFP. The AAV9.CB.shSOD1.GFP plasmid has a human SOD-1 cDNA inserted between the SV40 intron and the GFP cDNA. The constructs were packaged into either AAV9 genome.

Example 2

Intrathecal AAV9 Delivery and Cochlear Cell Targeting

Mice received one intrathecal (IT) injection of either $1.65\times10^{11}$ vg or $3.3\times10^{11}$ vg of scAAV9.shSOD1.CB.GFP or scAAV9.CB.GFP. The scAAV9.shSOD1.CB.GFP or scAAV9.CB.GFP was formulated in 1×PBS and 0.001% Pluronic F68 (denoted as PBS/F68). The mice were euthanized 3 weeks after injection. The cochlea of the treated mice were cryosectioned and stained for GFP. The section was also stained with DAPI to show the location of the cells.

Figure 2:
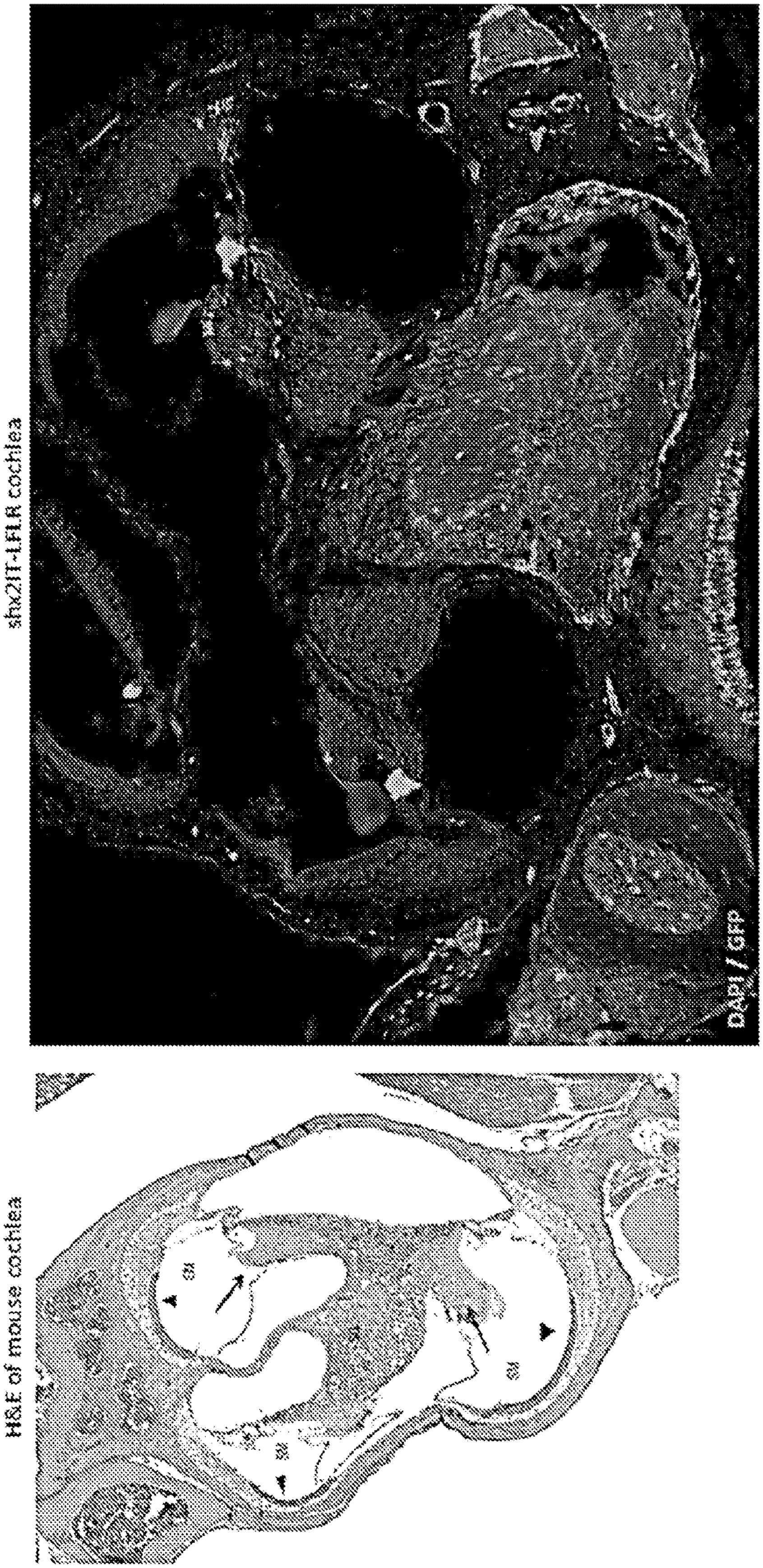
FIG. 2 demonstrates delivery of the GFP transgene to the cochlear after intrathecal injection of the vector. The sagittal cryosection of a cochlea is stained with DAPI and GFP. The hematoxylin and eosin stain is provided for reference only.
Figure 3:
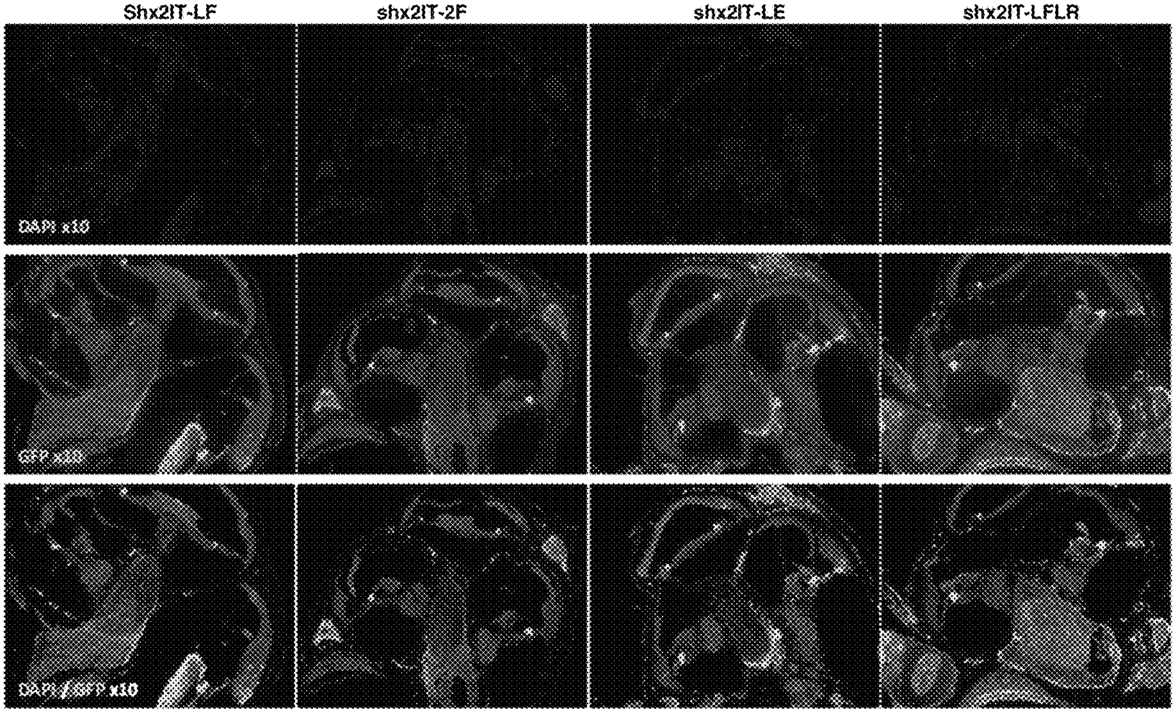
FIG. 3 provides staining of DAPI and GFP in the cochlea from 4 different mice (shx2IT-LF, shx2IT-2F, shx2IT-LE and shx2IT-LFLR) after intrathecal injection of the AAV vector.
Figure 4:
FIG. 4 provides staining of DAPI and GFP in the cochlea from a mouse after intrathecal injection of the AAV vector, and the different areas of the mouse cochlea are indicated.
Figure 5:
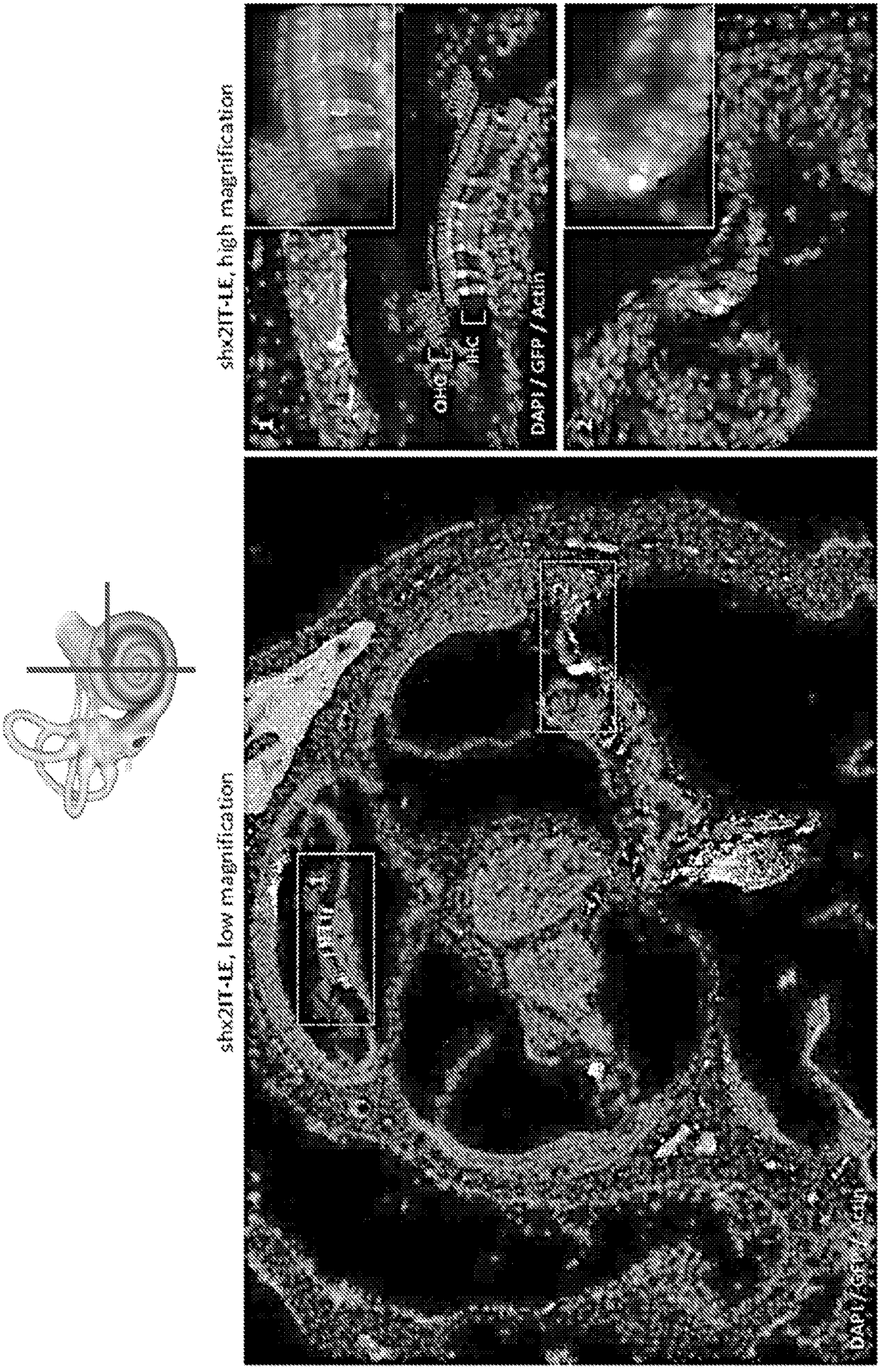
FIG. 5 provides staining for DAPI, GFP and actin in the cochlea from a mouse after intrathecal injection of the AAV vector.

FIGS. 2-5 provide data for the mice injected with scAAV9.shSOD1.CB.GFP. FIG. 2 is a staining for GFP in a sagittal cryosection of a cochlea from a IT treated. The hematoxylin and eosin staining is provided as a reference and is not a photo of a cochlea from an injected mouse (shx2IT-LFLR). This data demonstrates the strong GFP staining throughout the mouse cochlea after IT injection. FIG. 3 provides staining of 4 different mice (shx2IT-LF, shx2IT-2F, shx2IT-LE and shx2IT-LFLR). This figure shows widespread GFP expression and homogenous pattern of GFP expression in all injected mice. The cells in the organ of corti express high levels of GFP. FIG. 4 highlights the different areas of the mouse cochlea which had GFP expression after IT injection. In FIG. 5, the sagittal cryosection of the cochlea from a IT injected mouse (shx2IT-LE) was stained for actin, in addition to GFP and DAPI. This figure shows successful targeting of inner hair cells (IHCs) as they express the GFP transgene in several organ of corti. The figure shows a zoom in to larger magnification to clearly see the IHC cells.

Figure 6:
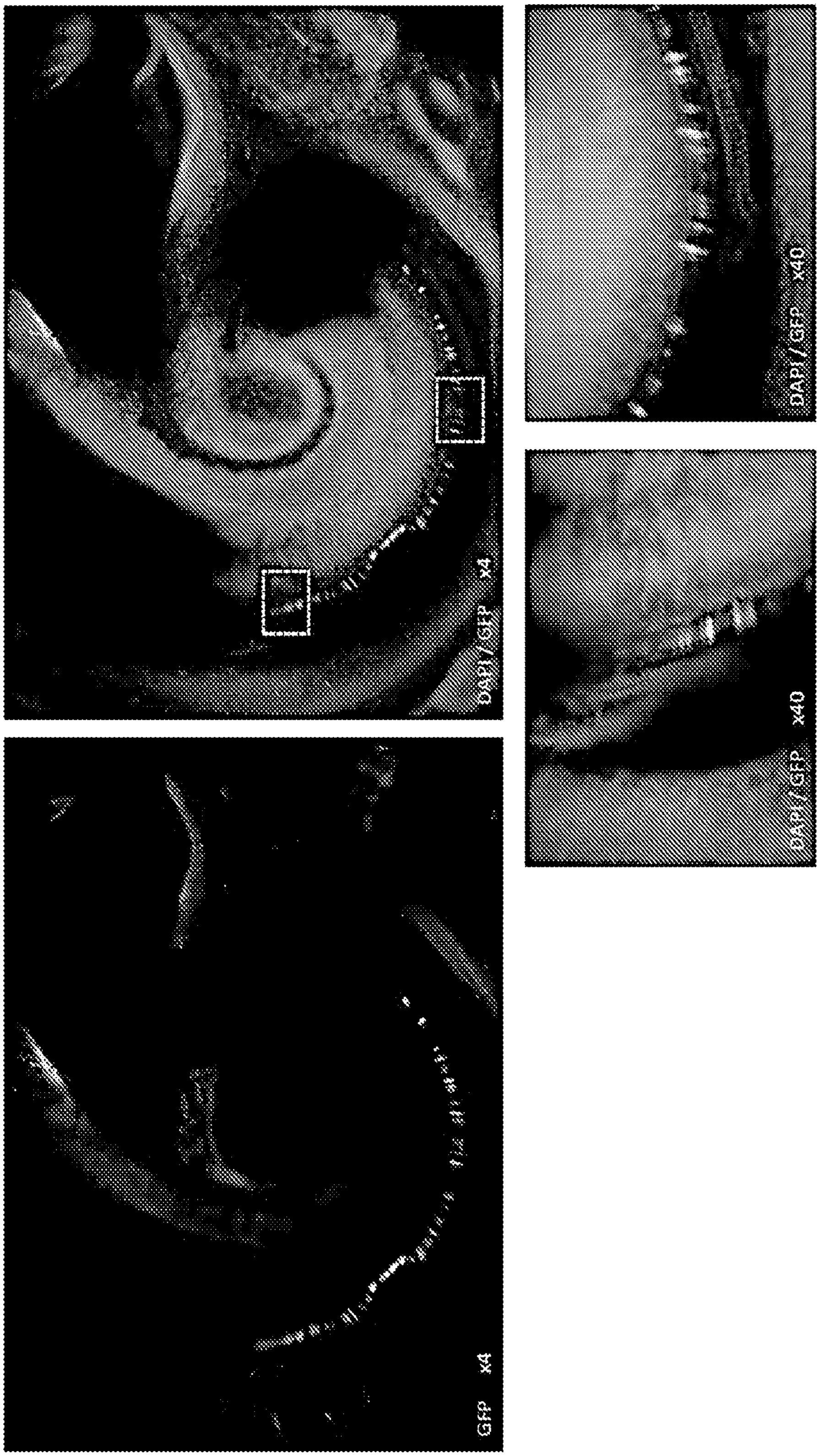
FIG. 6 provides staining for DAPI and GFP in the cochlea from a mouse after intrathecal injection for DAPI and GFP. The cut on this case is directed in a different orientation to allow the visualization of the targeting throughout the different areas of the cochlea.
Figure 7:
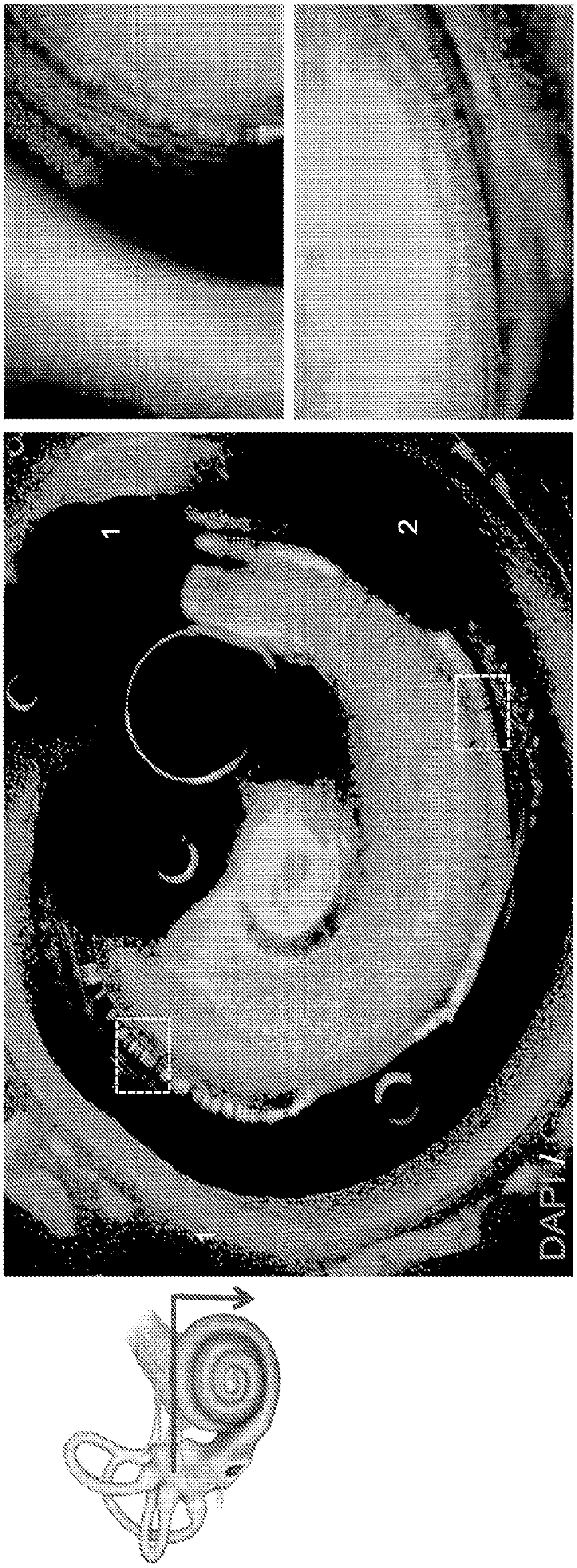
FIG. 7 provides staining for DAPI and GFP in the cochlea from a mouse after intrathecal injection. The cut in this case is directed in a different orientation to allow the visualization of the targeting throughout the different areas of the cochlea.
Figure 8:
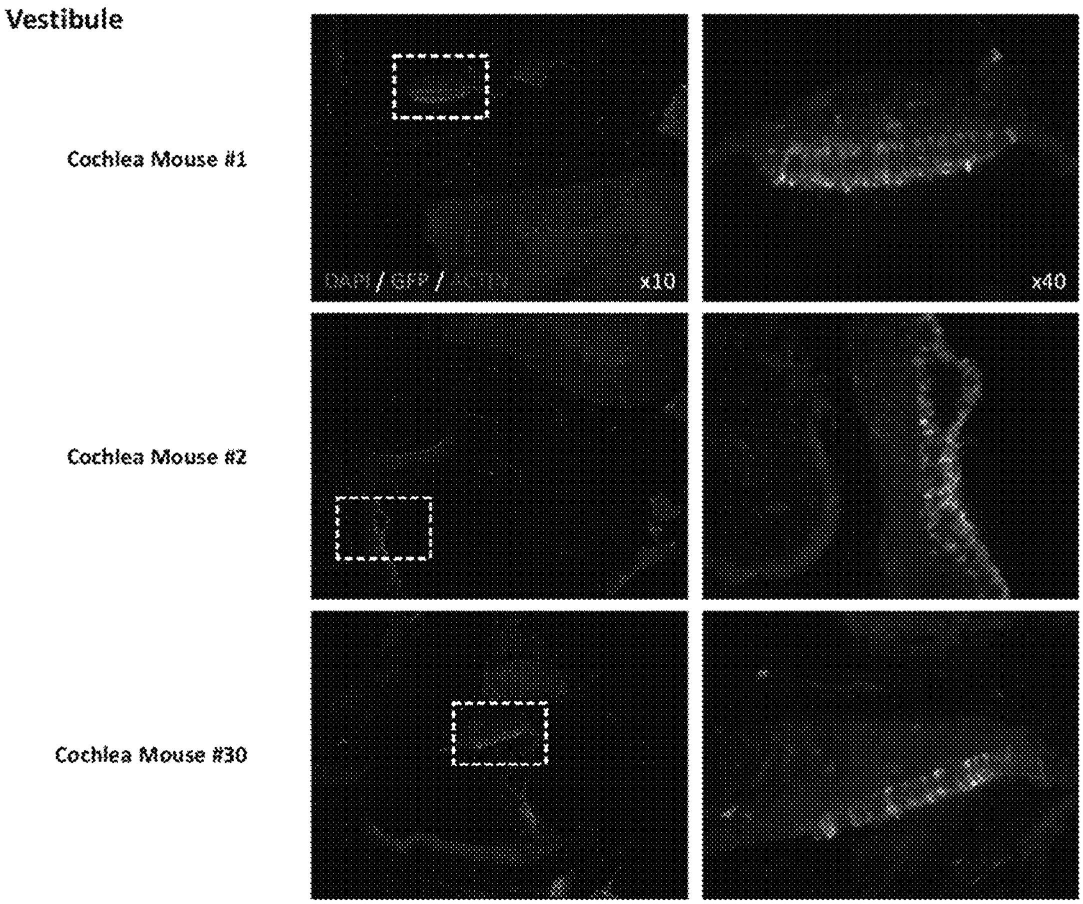
FIG. 8 provides staining for DAPI, GFP and Actin in the vestibule of the cochlea from a mouse after intrathecal injection.
Figure 9:
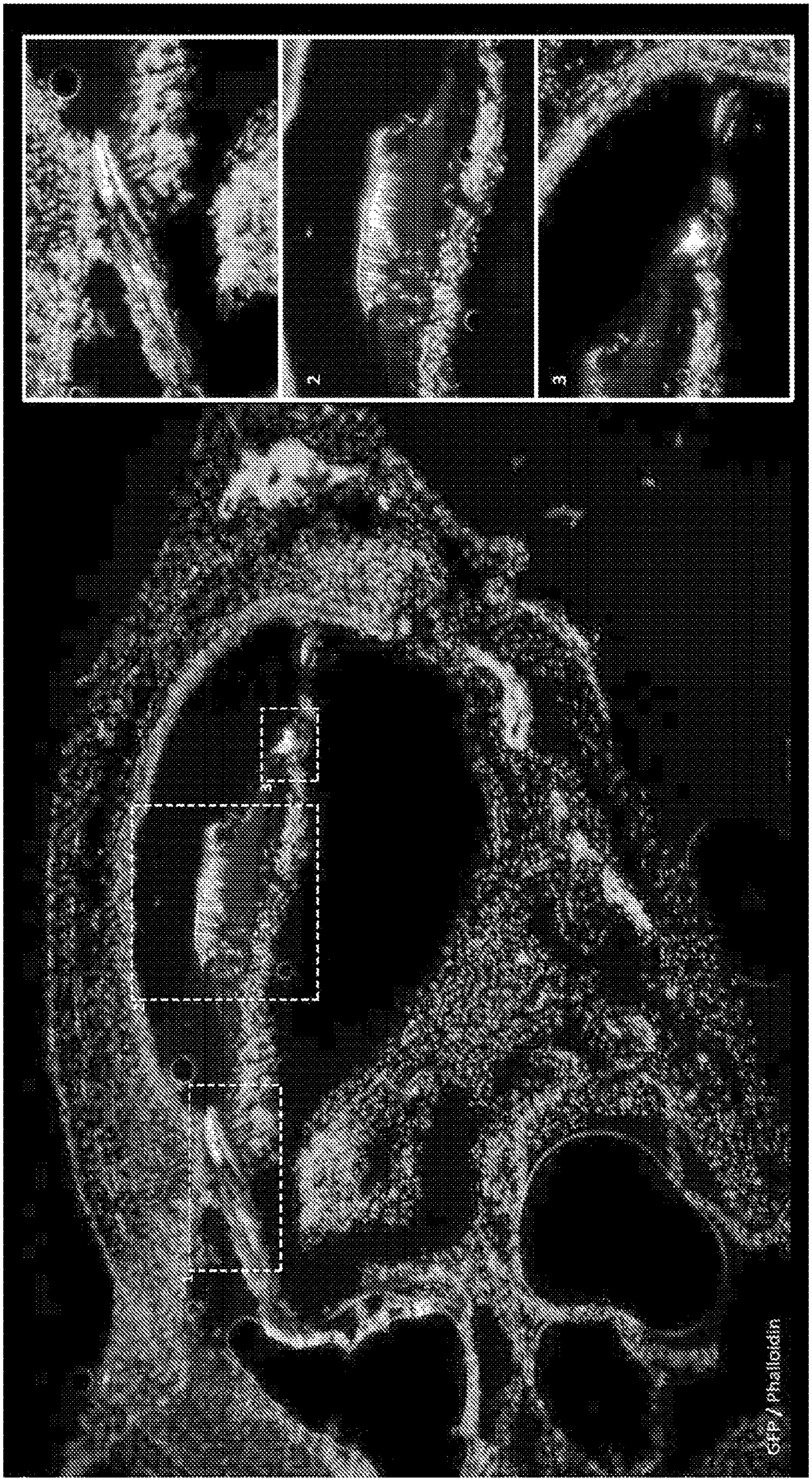
FIG. 9 provides staining for DAPI, GFP and Actin (phalloidin) in the cochlea from a mouse which was exposed to injury causing noise and the AAV was injected immediately after exposure to noise. The numbered sections are regions that are imaged at a higher magnification.
Figure 10:
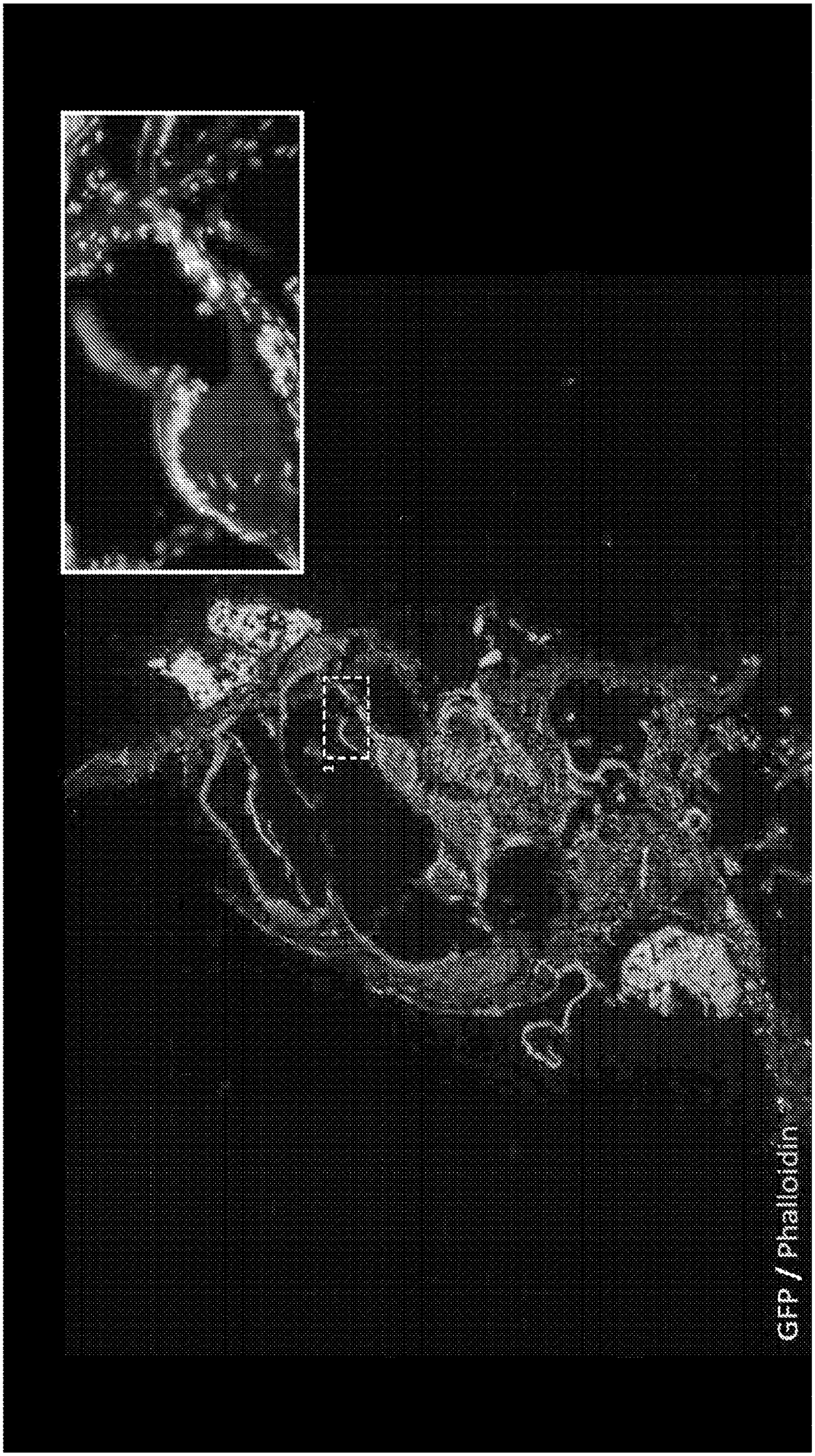
FIG. 10 provides staining for DAPI, GFP and Actin (phalloidin) in the cochlea from a mouse which was exposed to injury causing noise and the AAV was injected immediately after exposure to noise. The section labeled 1 is a region of the cochlea that is imaged at a higher magnification.
Figure 11:
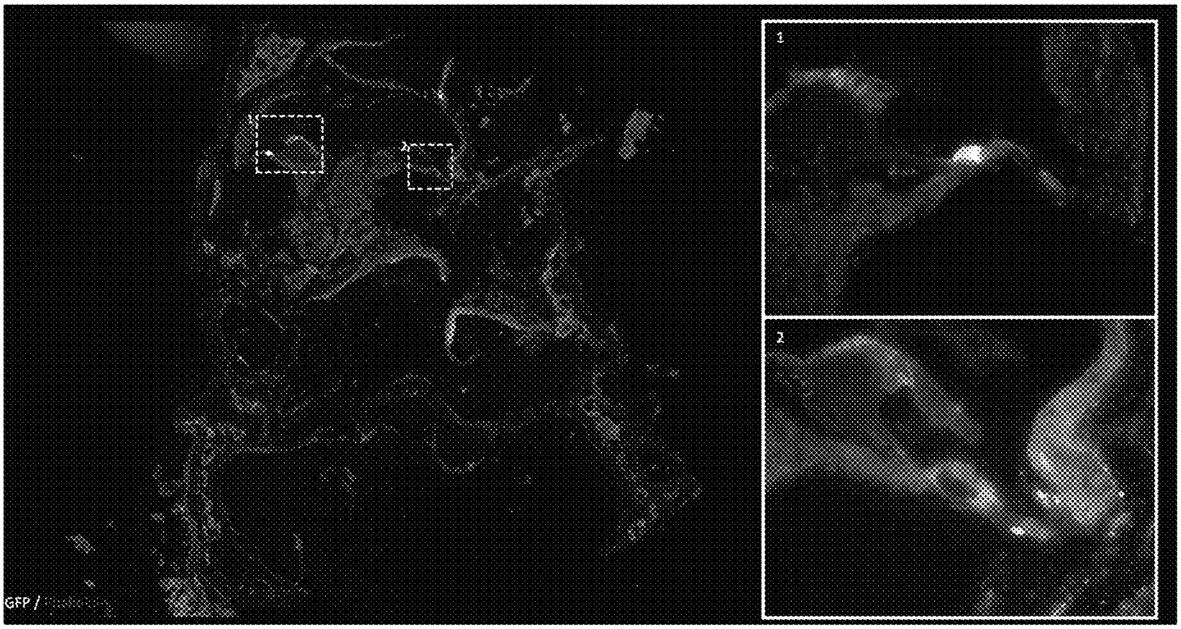
FIG. 11 provides staining for DAPI, GFP and Actin (phalloidin) in the cochlea from a mouse which was exposed to injury causing noise and the AAV was injected immediately after exposure to noise. The numbered sections are regions that are imaged at a higher magnification.
Figure 12:
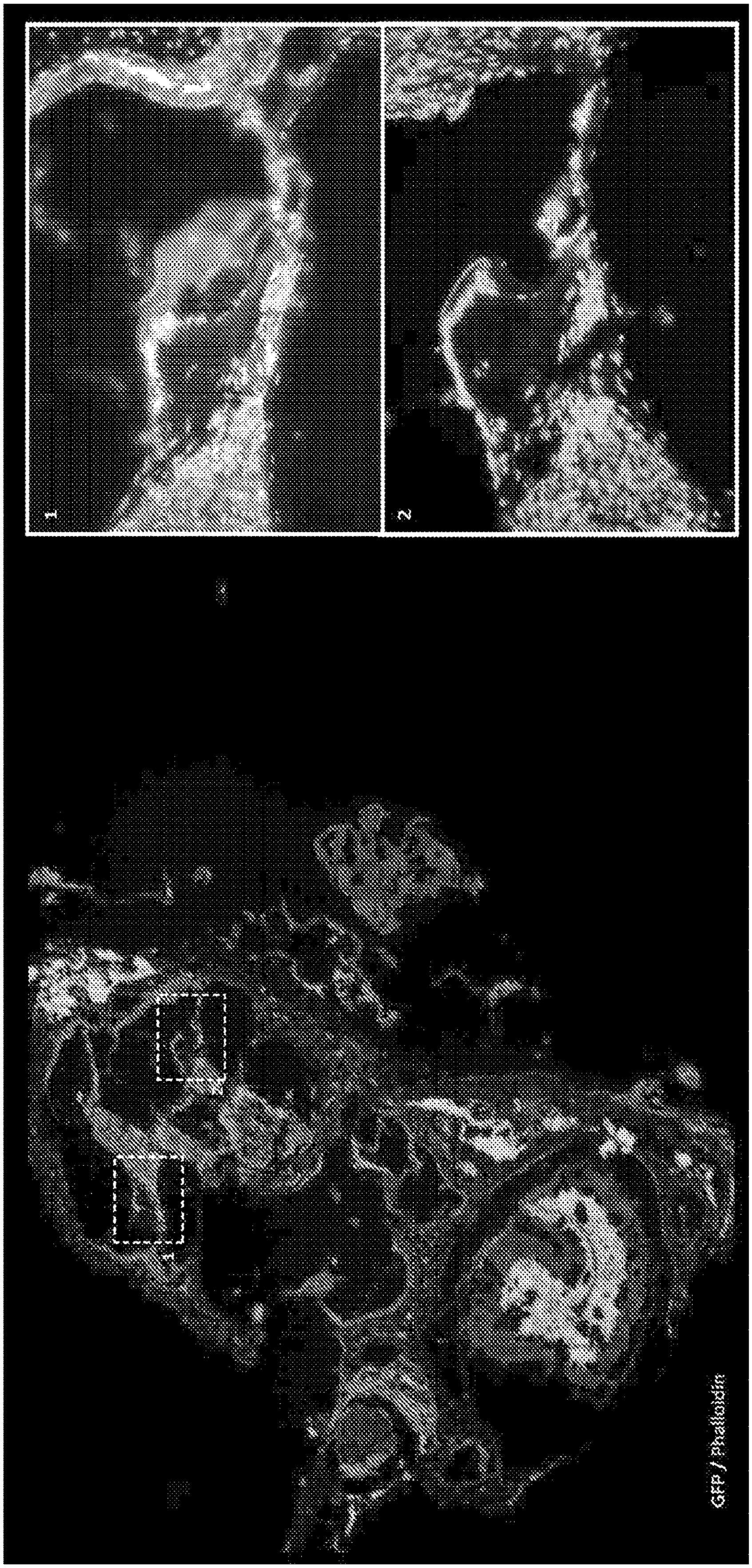
FIG. 12 provides staining for DAPI, GFP and Actin (phalloidin) in the cochlea from a mouse which was exposed to injury causing noise and the AAV was injected immediately after exposure to noise. The numbered sections are regions that are imaged at a higher magnification.
Figure 13:
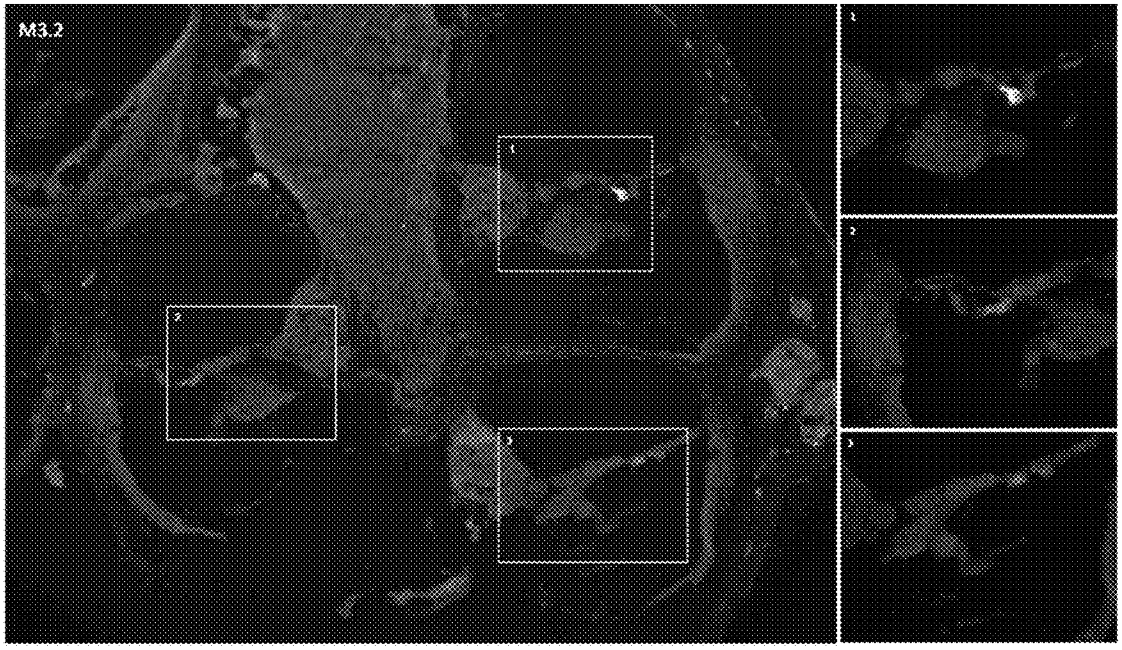
FIG. 13 provides staining for DAPI, GFP and myo7A in the cochlea from a mouse which was exposed to noise and the AAV was injected intrathecally 24 hours after exposure to noise.
Figure 14:
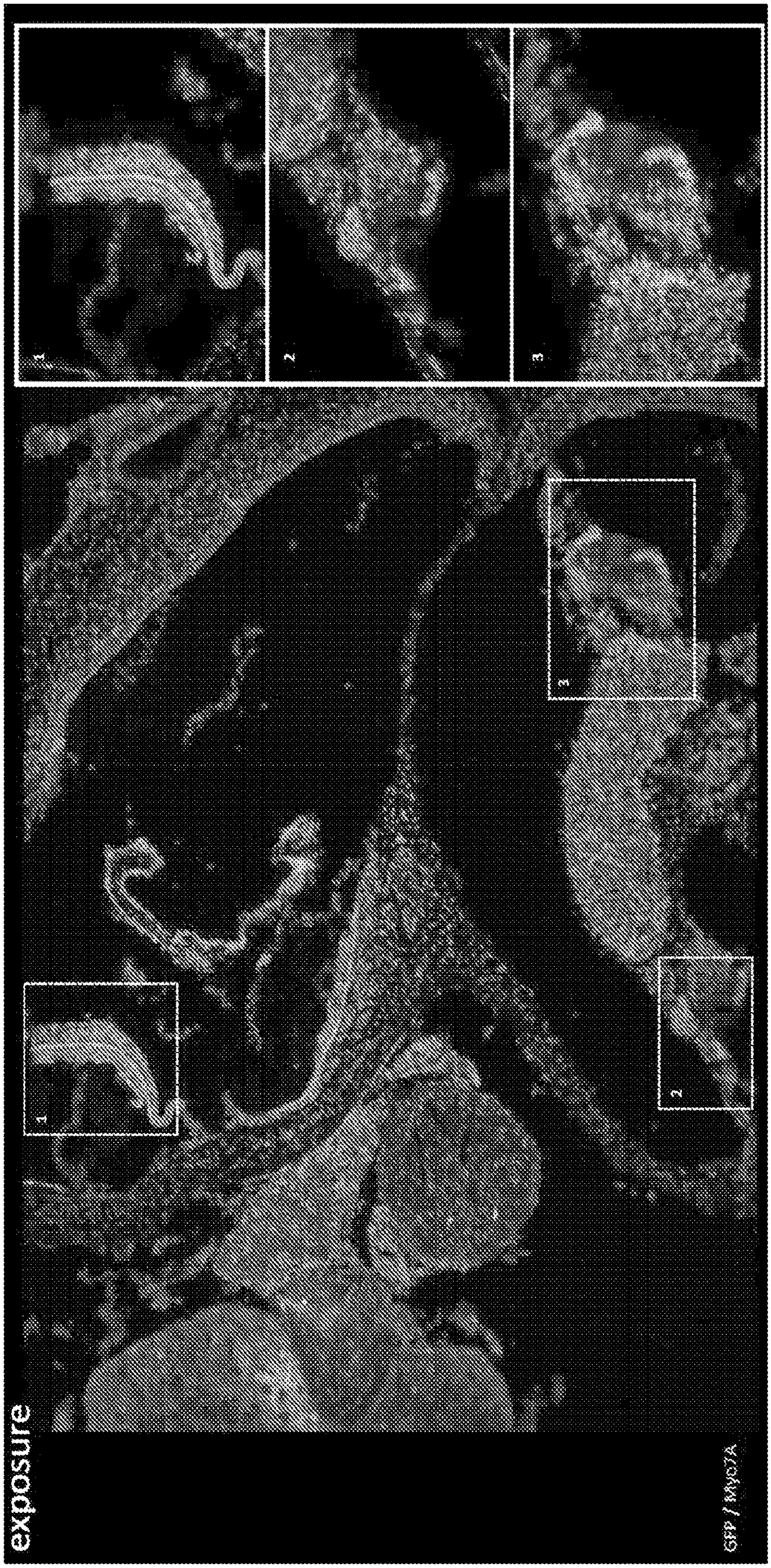
FIG. 14 provides staining for DAPI, GFP and myo7A in the cochlea from a mouse which was exposed to noise and the AAV was injected intrathecally 24 hours after exposure to noise. The numbered sections are regions that are imaged at a higher magnification.
Figure 15:
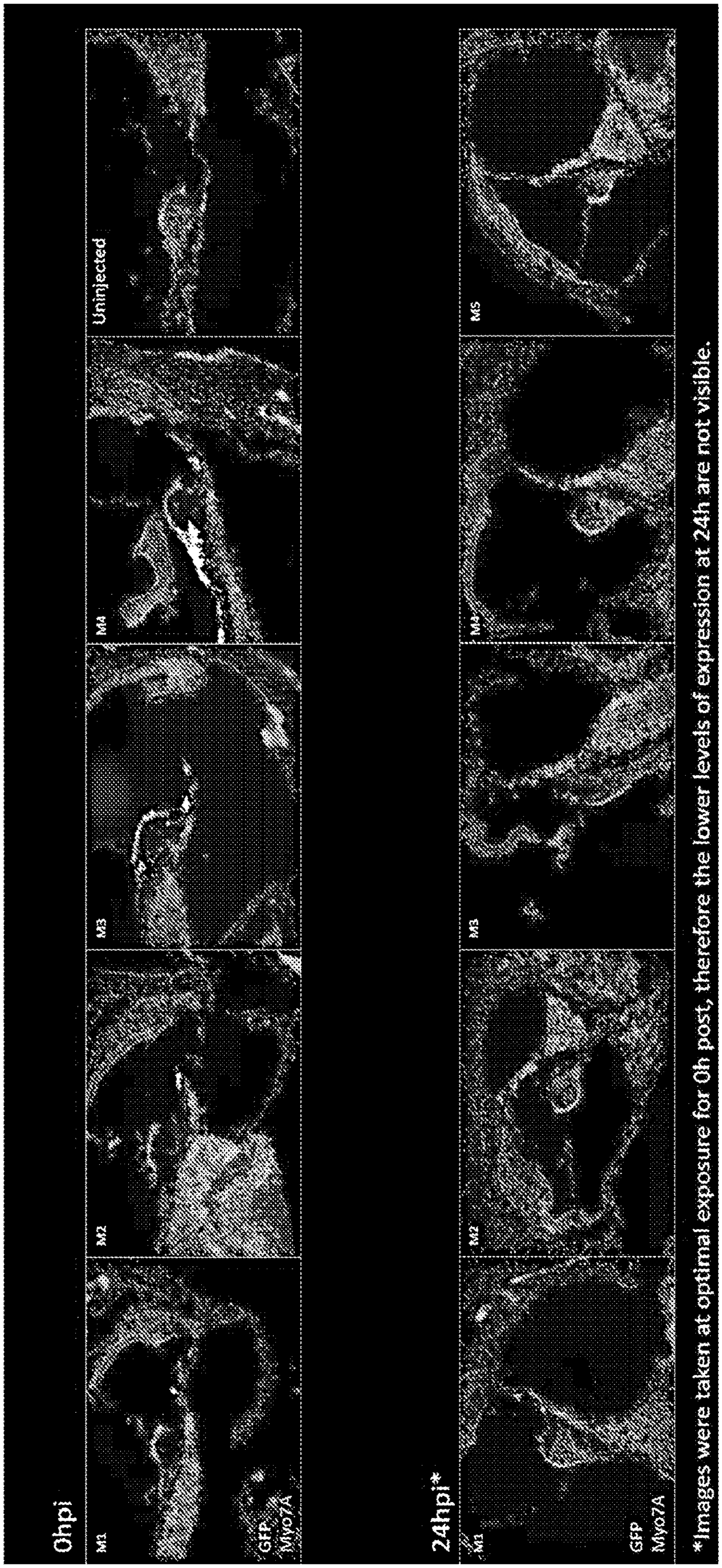
FIG. 15 provides staining for DAPI, GFP and myo7A in the cochlea from multiple mice which were exposed to noise and the AAV was injected intrathecally immediately after (0 hpi) or 24 hours (24 hpi) after exposure to noise.

FIGS. 6-8 provide data for the mice injected with scAAV9.CB.GFP. The cochlea of the IT injected mice were also sectioned in coronal orientation with a vibratome for a different view of the GFP expression pattern. FIGS. 6 and 7 demonstrates that the inner hair cells within the cochlea stain strongly for GFP in an injected mouse (mouse #2 and mouse #0). These figures also demonstrate that IT injection results in broad localization of GFP expression. FIG. 8 provides staining of the vestibule of the IT injected mice with DAPI, GFP and actin. These figures show targeting of the inner hair cells throughout the entire cochlea throughout the different turns where different wave lengths are processed.

Example 3

Transduction of Mouse Cochleae After Intrathecal Delivery and Exposure to Noise Stress to the hair cells in the inner ear of mice was induced by exposing the mouse to 100 db sound pressure level noise for 2 hours. scAAV9.CB.GFP was administered to mice via one intrathecal injection (IT) after exposure to the noise, either immediately after exposure (0 h.p.i.) or 24 hours after exposure (24 h.p.i.). The mice were injected with $1.65\times10^{11}$ vg of scAAV9.CB.GFP. The scAAV9.CB.GFP was formulated in 1×PBS and 0.001% Pluronic F68 (denoted as PBS/F68). The mice were euthanized 3 weeks after injection.

To examine the cochlear expression of the transgene, an immunohistochemistry analysis was performed to visualize GFP protein. Cross sections of the organ tissue was stained for Dapi, GFP and phalloidin, which stains actin filaments or myo7A which stains myosin-VIIa. Staining for myo7a was a specific method for labeling hair cells. As demonstrated in FIGS. 9-12, the inner hair cells expressed transgene GFP after IT injection of scAAV9.CB.GFP immediately after exposure to noise.

Figure 16:
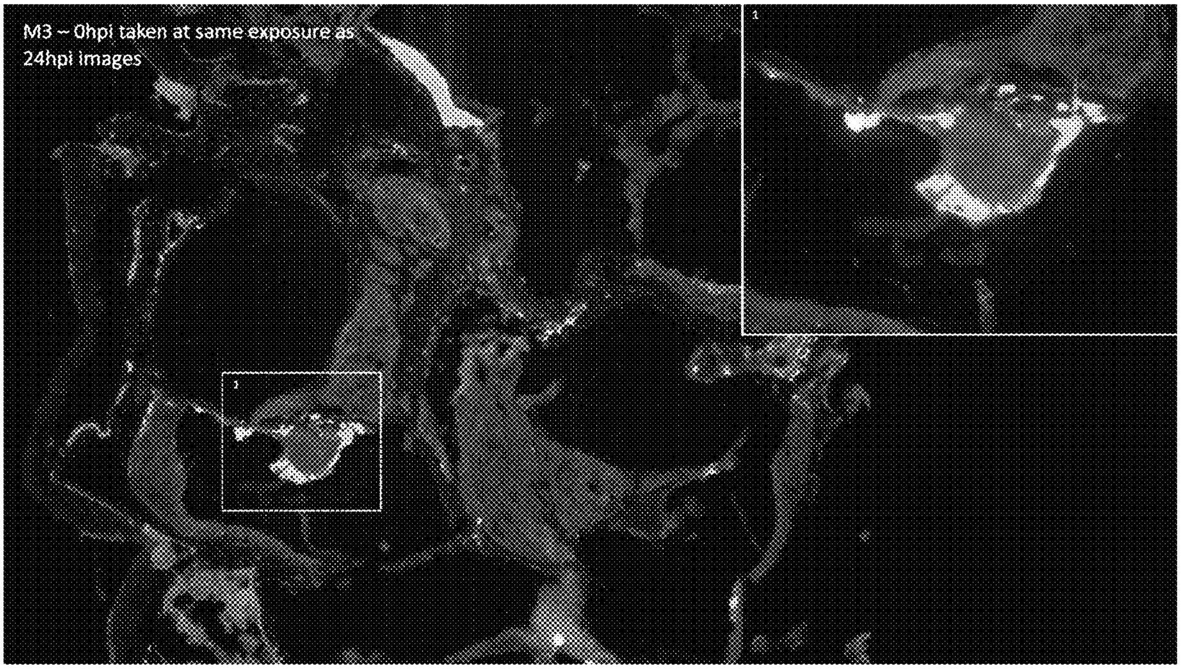
FIG. 16 provides staining for DAPI and GFP in a cochlea from a mouse which was exposed to noise and the AAV was injected immediately after (0 hpi) exposure to noise. This photo is imaged at the optimal exposure of the 24 hpi IT injected mice. This photo demonstrates that GFP expression in the 24 hpi intrathecal injected animals is lower than in 0 hpi intrathecal injected animals, as imaging at the optimal exposure for 24 hpi overexposes 0 hpi.
Figure 17:
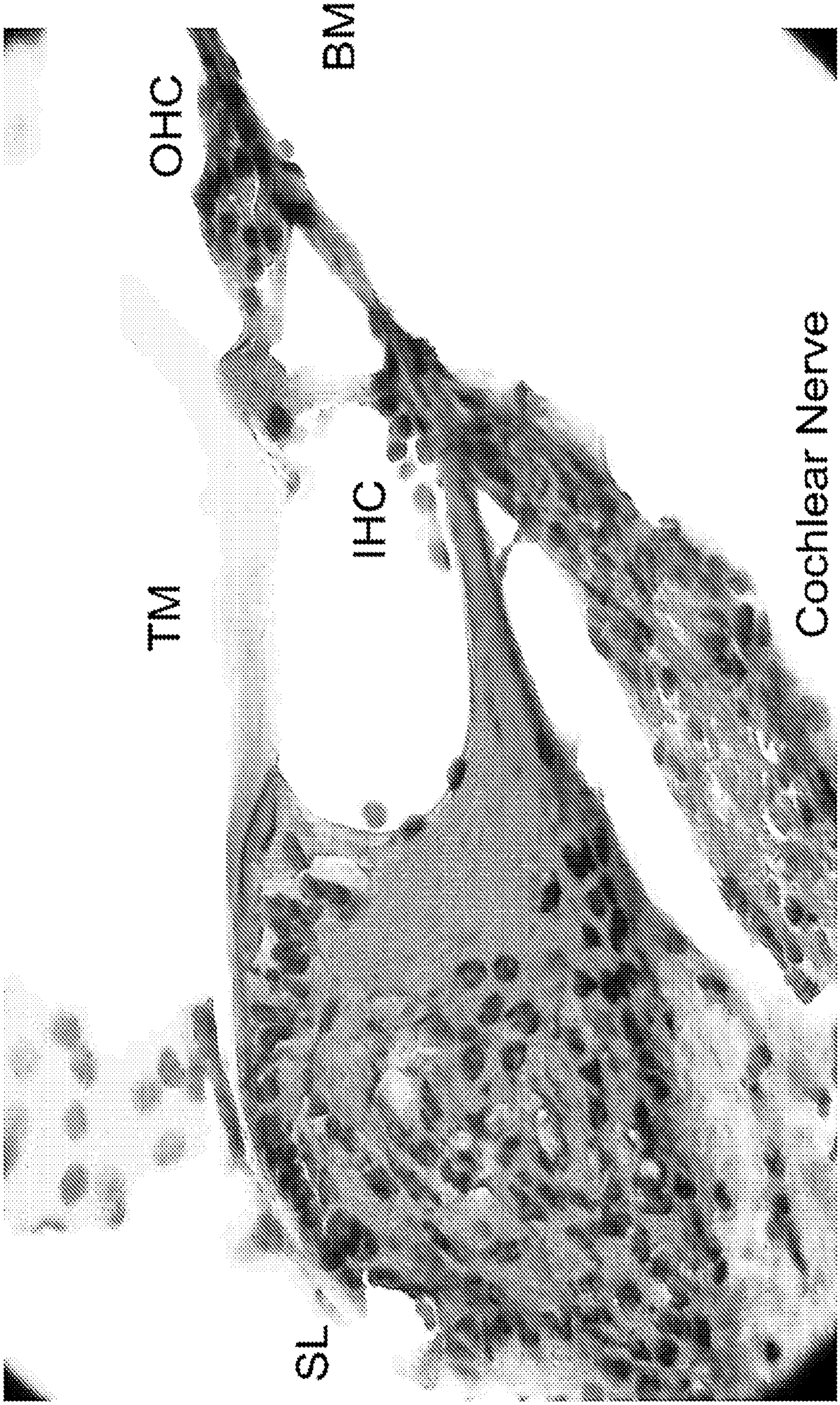
FIG. 17 provides hematoxylin and eosin stain of a cochlear nerve. The abbreviations indicated the locations of structures in the Organ of Corti. SL=Spiral limbus; TM=Tectorial membrane; OHC=Outer hair cells; IHC=Inner hair cells; BM=Basilar membrane.

FIGS. 13-16 provide staining of GFP and myo7A, and showed GFP expression was detected when IT injection occurred 24 hours after exposure to noise, but expression level was overall lower in inner hair cells. GFP expression was lower when the IT injection was delayed 24 hours after exposure to noise when compared to GFP expression when the IT injection occurred immediately after exposure to noise. FIGS. 16 and 17 demonstrate that administering scAAV9.CB.GFP 24 hours after injury resulted in a weaker GFP signal but targeting of the inner hair cells still occurs with the delayed administration. FIG. 16 is imaged at imaged at the optimal exposure of the 24 hpi IT injected mice. This photo demonstrates that GFP expression in the 24 hpi intrathecal injected animals is lower than in 0 hpi intrathecal injected animals, as imaging at the optimal exposure for 24 hpi overexposes 0 hpi.Hematoxylin and Eosin staining shown in FIG. 17 demonstrates that the inner hair cells are not damaged by the noise injury protocol used in this study.

Example 4

Figure 18:
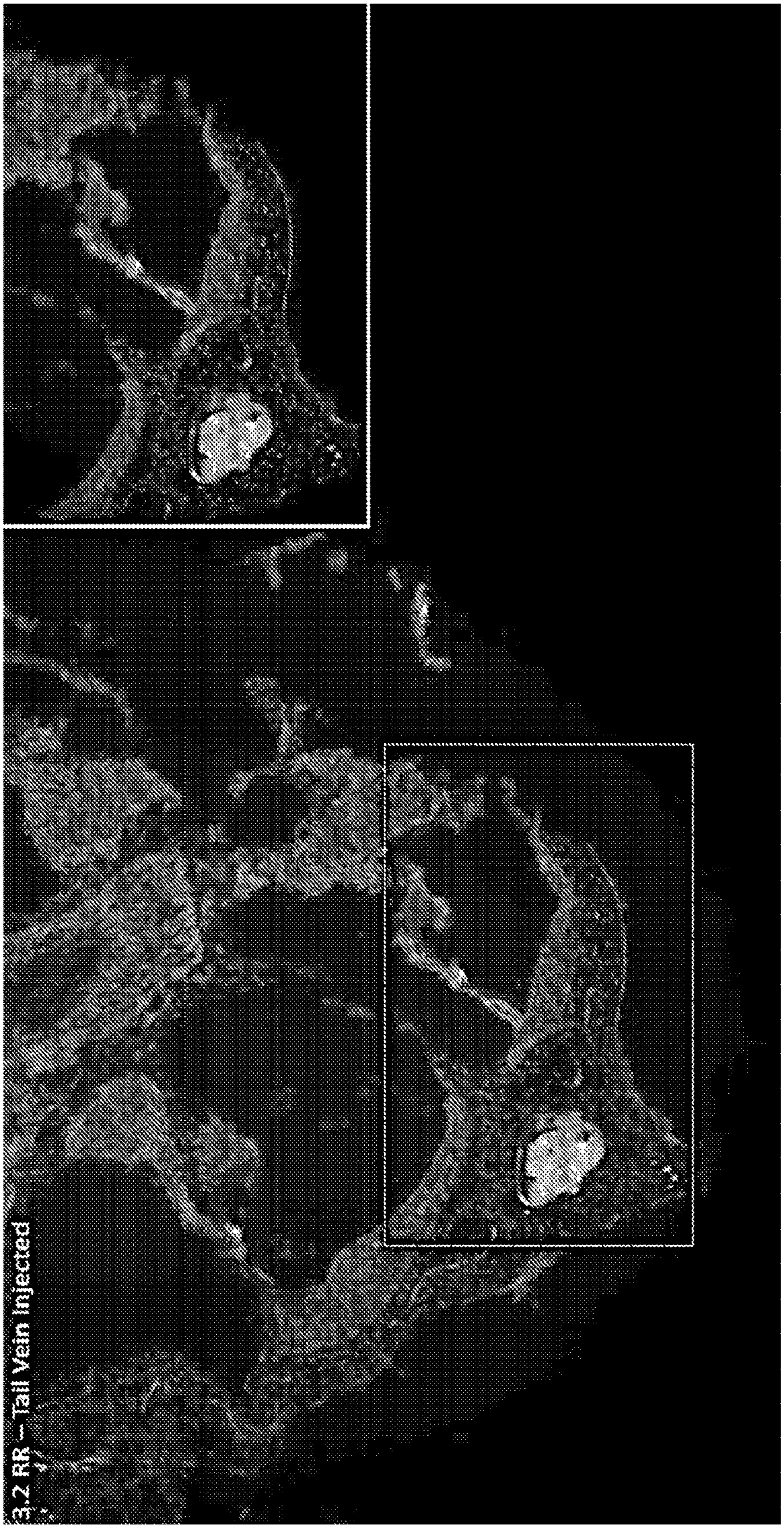
FIG. 18 provides staining for DAPI and GFP in the cochlea from a mouse after intravenous injection of AAV.
Figure 19:
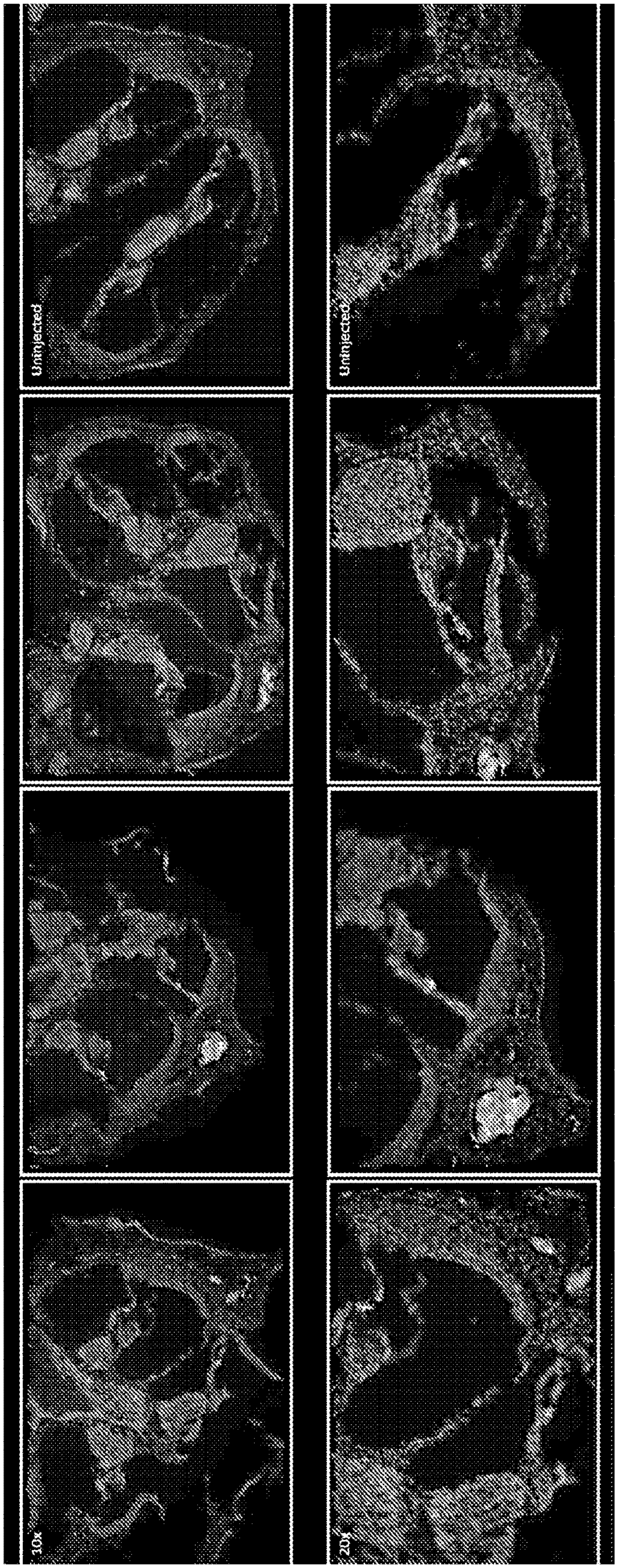
FIG. 19 provides staining for DAPI, GFP and MyoD in the cochlea from multiple mice after intravenous injection of AAV. Each panel is an image of the cochlea from a different mouse (top row is 10× and bottom row is 20×)
Figure 20:
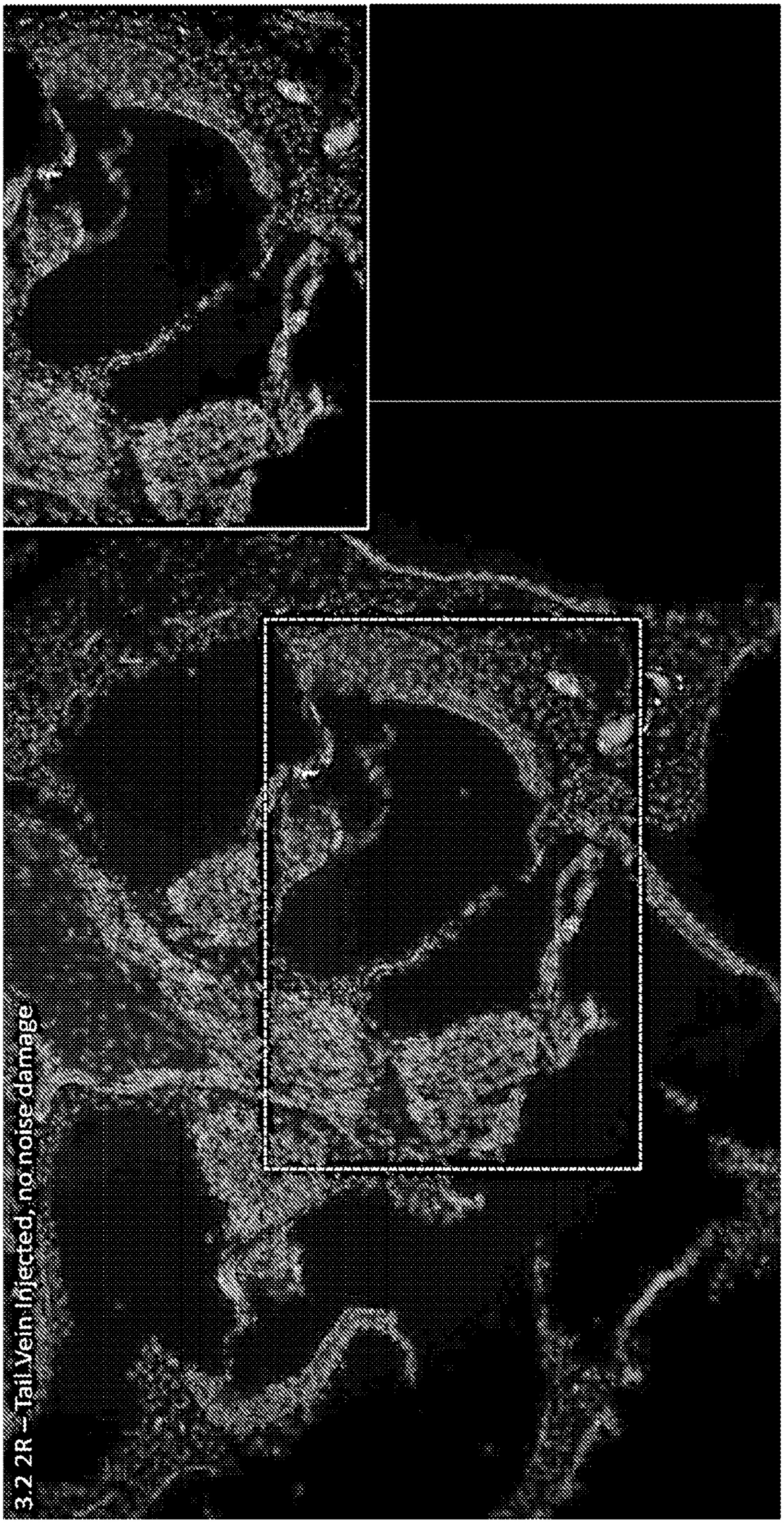
FIG. 20 provides staining for DAPI and GFP in the cochlea from a mouse after intravenous injection of AAV without noise damage.
Figure 21:
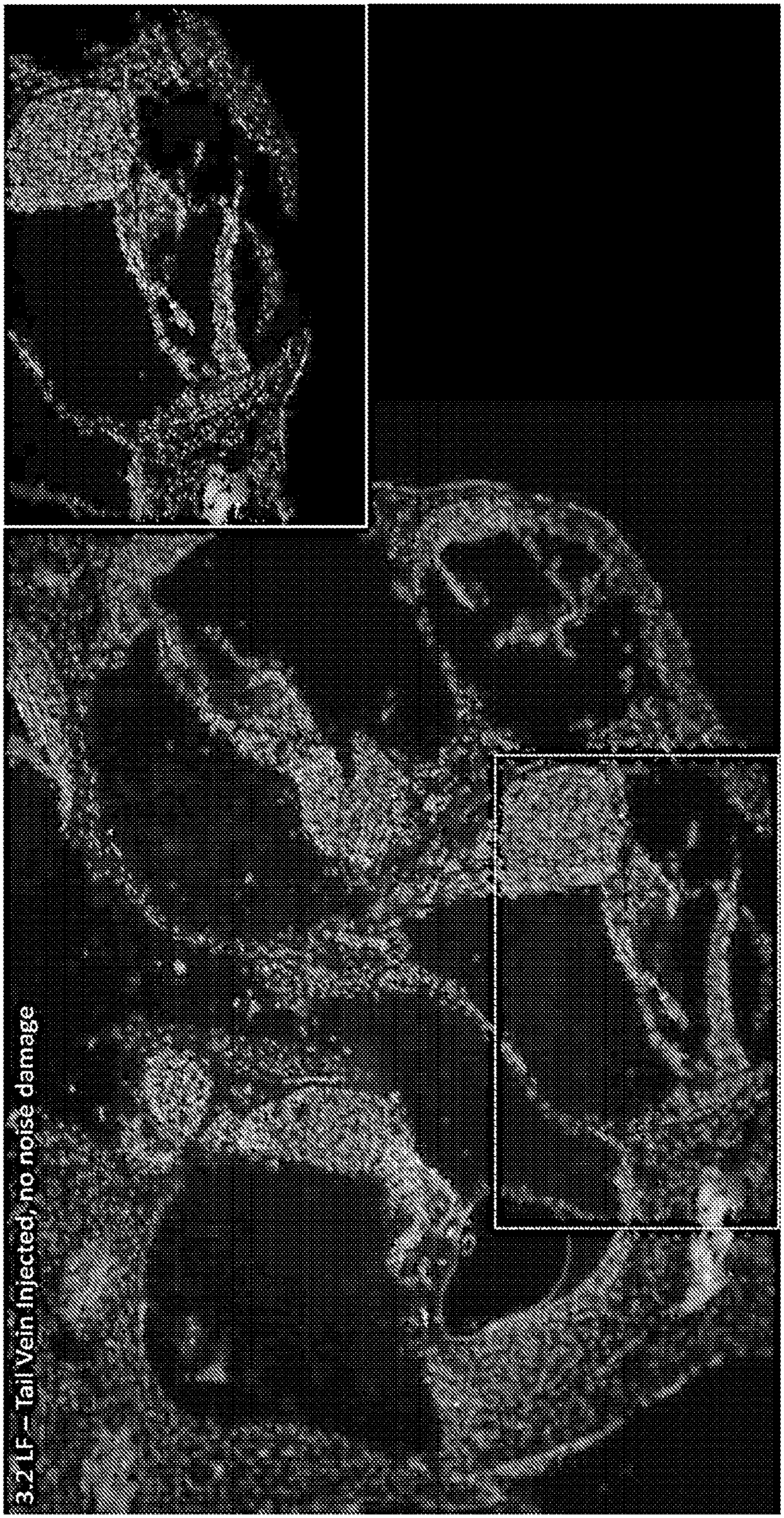
FIG. 21 provides staining for DAPI and GFP in the cochlea from a mouse after intravenous injection of AAV without noise damage.
Figure 22:
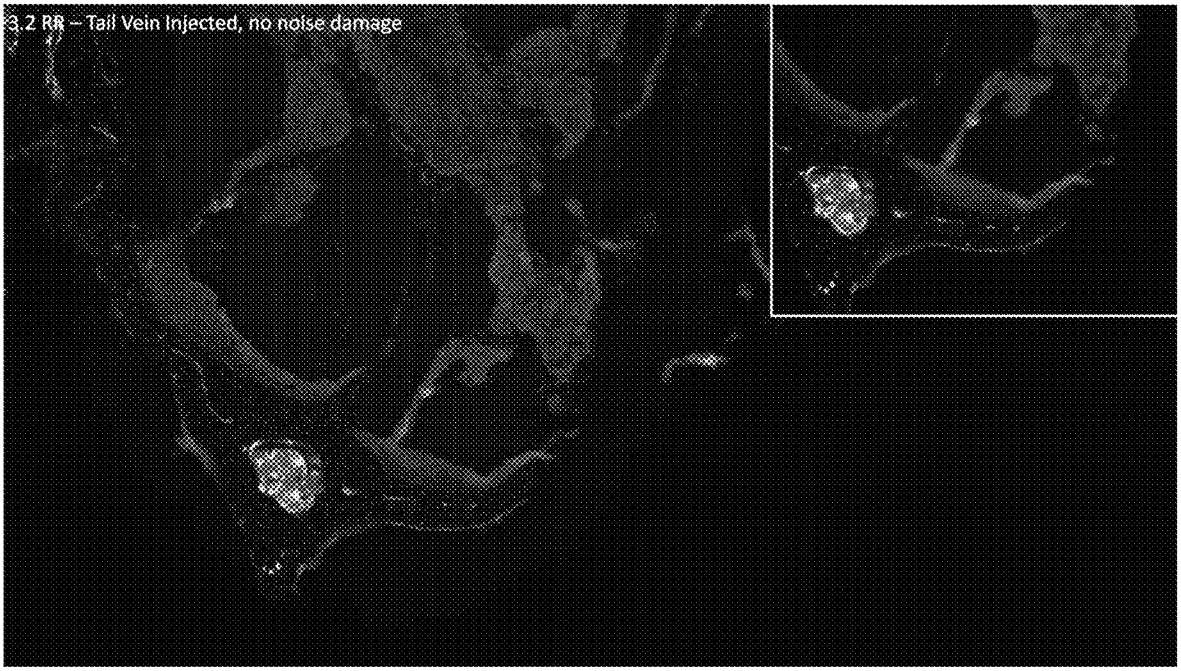
FIG. 22 provides staining for DAPI and GFP in the cochlea from a mouse after intravenous injection of AAV without noise damage.

Transduction of Mouse Cochlear After Intravenous Injection scAAV9.CB.GFP was also administered to normal mice via one tail vein injection. The mice were injected with $1.65\times10^{12}$ vg/kg of scAAV9.CB.GFP. The scAAV9.CB.GFP was formulated in 1×PBS and 0.001% Pluronic F68 (denoted as PBS/F68). The mice were euthanized 3 weeks after injection. As shown in FIG. 18, the preliminary data provided herein show that scAAV9.CB.GFP did deliver GFP to the cochlea but did not transduce the inner hair cells or the spinal ganglion neurons when administered using tail vein injection. Instead, it seems the transduction remained around blood vessels.

Figure 23:
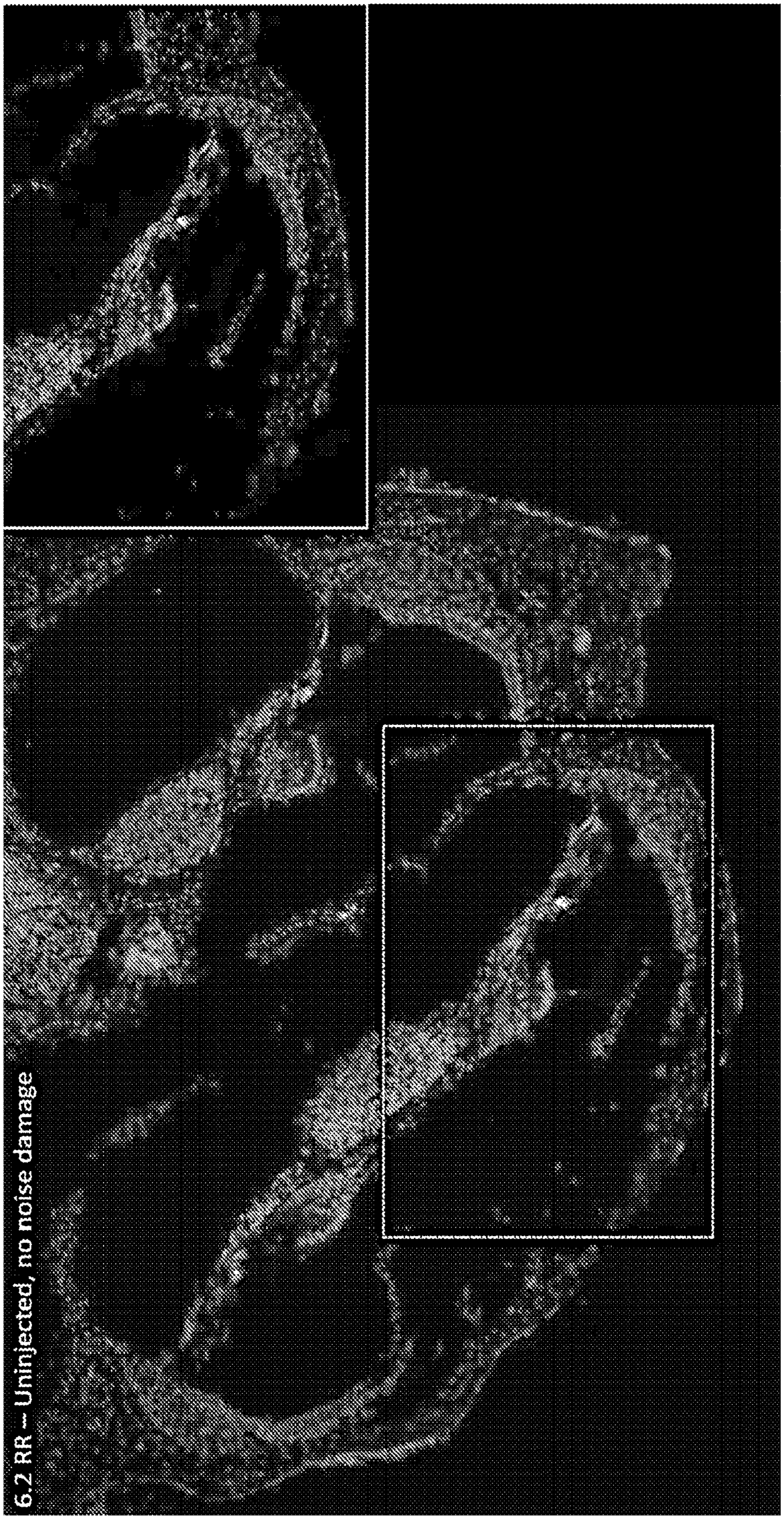
FIG. 23 provides staining for DAPI and GFP in the cochlea from a that control mouse that was exposed to noise damage but did not receive an intravenous injection of AAV.

A subsequent study was carried out in which $1.65\times10^{12}$ of scAAV9.CB.GFP formulated in PBS/F68 was administered to normal mice via one tail vein injection, and the mice were euthanized 3 weeks after injection. The immunohistochemistry data provided in FIGS. 19-22, intravenous injection did not result in transduction of inner hair cells in healthy cochlea. FIG. 23 provides data from an uninjected control mouse that was exposed to noise injury.

What is claimed:

1. A method of delivering a transgene to an inner hair cell in the cochlea of a subject, the method comprising administering a recombinant adeno-associated virus 9 (rAAV9) vector encoding the transgene, wherein the rAAV9 vector is administered to the subject using intrathecal delivery, and the transgene is delivered to an inner hair cell in the cochlea of the subject.

2. The method of claim 1, wherein the subject is suffering from hearing-loss or a hearing loss-related disorder.

3. The method of claim 2, wherein the hearing loss-related disorder is Waardenburg syndrome (WS), Branchiootorenal spectrum disorders, Neurofibromatosis 2 (NF2), Stickler syndrome, Usher syndrome type I, Usher syndrome type II, Usher syndrome type III, Pendred syndrome, Jervell and Lange-Nielsen syndrome, Biotinidase deficiency, Refsum disease, Alport syndrome, or Mohr-Tranebjaerg syndrome.

4. The method of claim 1, wherein the transgene encodes human atonal transcription factor (ATOH1) (SEQ ID NO: 2), otoferlin (SEQ ID NO: 4), gap junction protein beta 2 (SEQ ID NO: 6), pendrin (SLC26A) (SEQ ID NO: 8), forkhead box 1 (FOXG1) (SEQ ID NO: 10), activin A or Inhibin (SEQ ID No: 12), follistatin (FST) (SEQ ID NO: 14), galectin-1 (SEQ ID NO: 19), or galectin-3 (SEQ ID NO: 21).

5. The method of claim 1, wherein the transgene is a miRNA or, siRNA against human atonal transcription factor (ATOH1) (SEQ ID NO: 2), otoferlin (SEQ ID NO: 4), gap junction protein beta 2 (SEQ ID NO: 6), pendrin (SLC26A) (SEQ ID NO: 8), forkhead box 1 (FOXG1) (SEQ ID NO: 10), activin A or Inhibin (SEQ ID No: 12), follistatin (FST) (SEQ ID NO: 14), galectin-1 (SEQ ID NO: 19), or galectin-3 (SEQ ID NO: 21).

6. The method of claim 1, wherein the rAAV9 vector is administered using intrathecal delivery, and the method further comprises placing the subject in the Trendelenburg position after administering of the rAAV9 vector.

* * * * *

SEQUENCE LISTING

```
<160> NUMBER OF SEQ ID NOS: 22

<210> SEQ ID NO 1
<211> LENGTH: 270
<212> TYPE: DNA
<213> ORGANISM: Artificial Sequence
<220> FEATURE:
<223> OTHER INFORMATION: Synthetic Polypeptide

<400> SEQUENCE: 1

ccacgttctg cttcactctc cccatctccc ccccctcccc acccccaatt ttgtatttat      60

ttatttttta attattttgt gcagcgatgg gggcgggggg gggggggggg cgcgcgccag     120

gcggggcggg gcggggcgag gggcggggcg gggcgaggcg gagaggtgcg gcggcagcca     180

atcagagcgg cgcgctccga aagtttcctt ttatggcgag gcggcggcgg cggcggccct     240

ataaaaagcg aagcgcgcgg cgggcgggag                                      270

<210> SEQ ID NO 2
<211> LENGTH: 2212
<212> TYPE: DNA
<213> ORGANISM: Homo sapiens

<400> SEQUENCE: 2

ggagaagcat agttgcacgc gacctggtgt gtgatctccg agtgggtggg ggagggtcga      60

ggagggaaaa aaaaataaga cgttgcagaa gagacccgga aagggccttt tttttggttg     120

agctggtgtc ccagtgctgc ctccgatcct gagcctccga gcctttgcag tgcaatgtcc     180

cgcctgctgc atgcagaaga gtgggctgaa gtgaaggagt tgggagacca ccatcgccag     240

ccccagccgc atcatctccc gcaaccgccg ccgccgccgc agccacctgc aactttgcag     300

gcgagagagc atcccgtcta cccgcctgag ctgtccctcc tggacagcac cgacccacgc     360

gcctggctgg ctcccacttt gcagggcatc tgcacggcac gcgccgccca gtatttgcta     420

cattccccgg agctgggtgc ctcagaggcc gctgcgcccc gggacgaggt ggacggccgg     480

ggggagctgg taaggaggag cagcggcggt gccagcagca gcaagagccc cgggccggtg     540

aaagtgcggg aacagctgtg caagctgaaa ggcggggtgg tggtagacga gctgggctgc     600

agccgccaac gggccccttc cagcaaacag gtgaatgggg tgcagaagca gagacggcta     660

gcagccaacg ccagggagcg gcgcaggatg catgggctga accacgcctt cgaccagctg     720

cgcaatgtta tcccgtcgtt caacaacgac aagaagctgt ccaaatatga gaccctgcag     780
```

-continued

```
atggcccaaa tctacatcaa cgccttgtcc gagctgctac aaacgcccag cggaggggaa    840

cagccaccgc cgcctccagc ctcctgcaaa agcgaccacc accaccttcg caccgcggcc    900

tcctatgaag gggcgcgggg caacgcgacc gcagctgggg ctcagcaggc ttccggaggg    960

agccagcggc cgaccccgcc cgggagttgc cggactcgct tctcagcccc agcttctgcg   1020

ggagggtact cggtgcagct ggacgctctg cacttctcga ctttcgagga cagcgccctg   1080

acagcgatga tggcgcaaaa gaatttgtct ccttctctcc ccgggagcat cttgcagcca   1140

gtgcaggagg aaaacagcaa aacttcgcct cggtcccaca gaagcgacgg ggaattttcc   1200

ccccattccc attacagtga ctcggatgag gcaagttagg aaggtgacag aagcctgaaa   1260

actgagacag aaacaaaact gccctttccc agtgcgcggg aagccccgcg gttaaagatc   1320

cccgcaccct ttaatttttg ctctgcgatg gtcgttgttt agcaacgact tggcttcaga   1380

tggcagctac atttgatggt ttgcaaatgc cgccgctgtt ccaaacttcc tacggtccat   1440

attgtttgat gaaaactttc tgttaaaatt gtgtcctttc cgcccacctt ctgctccccc   1500

tttagataga tacggtataa ttgtaggtac ccgtatatgg catcattatt ctagttccct   1560

gctgccaata cgctgctaaa acgtcgcatc ttctctgtca ctggtttggg tttaatttat   1620

tttacgccct gggcatccat ccttgtgtgt tgcgcactca agtgtgggag atttagtctt   1680

ccgaagttgt tttccaaaat gcacaatgaa acgcaaaatt agtgcttcca aagtggataa   1740

cttttgacta tggaattgtt agaaaacaag aaactttaag gtttatatat tgtataaaca   1800

tacccagtat gtgcatccga tcgcgagaac gttggcgtct tttaggaaac tccgcgcacg   1860

cactttatca gccgctgctg cggtggtggc tccaggagaa actcaactgc caattgcaga   1920

ccagtttttt ttttttaaa cacagccact tataattctt aagctctttg caaatgtttg   1980

tttaaaaaat gaaaaattaa aaaaaatcta gtagtgtcaa acgcatttgg tcaattttat   2040

tttgctttgt taatattaga aaacttattt attattgttt gctaccattt ctacttatct   2100

tgattcattt tttacgtttt ctactcgaga tcattttatt ttaatttagc aaagccaact   2160

gcccttgttt aatgtatttt gttttgcaaa tgattaaaat aaatgtgaaa ag           2212
```

<210> SEQ ID NO 3
<211> LENGTH: 354
<212> TYPE: PRT
<213> ORGANISM: Homo sapiens

<400> SEQUENCE: 3

```
Met Ser Arg Leu Leu His Ala Glu Glu Trp Ala Glu Val Lys Glu Leu
1               5                   10                  15

Gly Asp His His Arg Gln Pro Gln Pro His His Leu Pro Gln Pro Pro
            20                  25                  30

Pro Pro Pro Gln Pro Pro Ala Thr Leu Gln Ala Arg Glu His Pro Val
        35                  40                  45

Tyr Pro Pro Glu Leu Ser Leu Leu Asp Ser Thr Asp Pro Arg Ala Trp
    50                  55                  60

Leu Ala Pro Thr Leu Gln Gly Ile Cys Thr Ala Arg Ala Ala Gln Tyr
65                  70                  75                  80

Leu Leu His Ser Pro Glu Leu Gly Ala Ser Glu Ala Ala Ala Pro Arg
                85                  90                  95

Asp Glu Val Asp Gly Arg Gly Glu Leu Val Arg Arg Ser Ser Gly Gly
            100                 105                 110

Ala Ser Ser Ser Lys Ser Pro Gly Pro Val Lys Val Arg Glu Gln Leu
```

```
        115                 120                 125

Cys Lys Leu Lys Gly Gly Val Val Val Asp Glu Leu Gly Cys Ser Arg
    130                 135                 140

Gln Arg Ala Pro Ser Ser Lys Gln Val Asn Gly Val Gln Lys Gln Arg
145                 150                 155                 160

Arg Leu Ala Ala Asn Ala Arg Glu Arg Arg Arg Met His Gly Leu Asn
                165                 170                 175

His Ala Phe Asp Gln Leu Arg Asn Val Ile Pro Ser Phe Asn Asn Asp
            180                 185                 190

Lys Lys Leu Ser Lys Tyr Glu Thr Leu Gln Met Ala Gln Ile Tyr Ile
        195                 200                 205

Asn Ala Leu Ser Glu Leu Leu Gln Thr Pro Ser Gly Gly Glu Gln Pro
    210                 215                 220

Pro Pro Pro Pro Ala Ser Cys Lys Ser Asp His His His Leu Arg Thr
225                 230                 235                 240

Ala Ala Ser Tyr Glu Gly Gly Ala Gly Asn Ala Thr Ala Ala Gly Ala
                245                 250                 255

Gln Gln Ala Ser Gly Gly Ser Gln Arg Pro Thr Pro Pro Gly Ser Cys
            260                 265                 270

Arg Thr Arg Phe Ser Ala Pro Ala Ser Ala Gly Gly Tyr Ser Val Gln
        275                 280                 285

Leu Asp Ala Leu His Phe Ser Thr Phe Glu Asp Ser Ala Leu Thr Ala
    290                 295                 300

Met Met Ala Gln Lys Asn Leu Ser Pro Ser Leu Pro Gly Ser Ile Leu
305                 310                 315                 320

Gln Pro Val Gln Glu Glu Asn Ser Lys Thr Ser Pro Arg Ser His Arg
                325                 330                 335

Ser Asp Gly Glu Phe Ser Pro His Ser His Tyr Ser Asp Ser Asp Glu
            340                 345                 350

Ala Ser


<210> SEQ ID NO 4
<211> LENGTH: 7214
<212> TYPE: DNA
<213> ORGANISM: Homo sapiens

<400> SEQUENCE: 4

gtgagtcgct gcaggagcag cttagctcgg cttggttgcc ttggtctctg tgggcagcat     60

cggagggggg tcgggaggag gaggaggagg cagcggcaga gaagagagag gcgtgtgagc    120

cgtgctccac cggctagctc cttcccgctg ctcctgcctg gcagtgccag gcagcccaca    180

ccagcatggc cttgctcatc cacctcaaga cagtctcgga gctgcggggc aggggcgacc    240

ggatcgccaa agtgactttc cgagggcaat ccttctactc tcgggtcctg gagaactgtg    300

aggatgtggc tgactttgat gagacatttc ggtggccggt ggccagcagc atcgacagaa    360

atgagatgct ggagattcag gttttcaact acagcaaagt cttcagcaac aagctcatcg    420

ggaccttccg catggtgctg cagaaggtgg tagaggagag ccatgtggag gtgactgaca    480

cgctgattga tgacaacaat gctatcatca agaccagcct gtgcgtggag gtccggtatc    540

aggccactga cggcacagtg ggctcctggg acgatgggga cttcctggga gatgagtctc    600

ttcaagagga agagaaggac agccaagaga cggatggact gctcccaggc tcccggccca    660

gctcccggcc cccaggagag aagagcttcc ggagagccgg gaggagcgtg ttctccgcca    720

tgaagctcgg caaaaaccgg tctcacaagg aggagcccca aagaccagat gaaccggcgg    780
```

```
tgctggagat ggaagacctt gaccatctgg ccattcggct aggagatgga ctggatcccg    840
actcggtgtc tctagcctca gtcacagctc tcaccactaa tgtctccaac aagcgatcta    900
agccagacat taagatggag ccaagtgctg ggcggcccat ggattaccag gtcagcatca    960
cggtgatcga ggcccggcag ctggtgggct tgaacatgga ccctgtggtg tgcgtggagg   1020
tgggtgacga caagaagtac acatccatga aggagtccac taactgcccc tattacaacg   1080
agtacttcgt cttcgacttc catgtctctc cggatgtcat gtttgacaag atcatcaaga   1140
tttcggtgat tcactccaag aacctgctgc gcagtggcac cctggtgggc tccttcaaaa   1200
tggacgtggg aaccgtgtac tcgcagccag agcaccagtt ccatcacaag tgggccatcc   1260
tgtctgaccc cgatgacatc tcctcggggc tgaagggcta cgtgaagtgt gacgttgccg   1320
tggtgggcaa aggggacaac atcaagacgc cccacaaggc caatgagacc gacgaagatg   1380
acattgaggg gaacttgctg ctccccgagg gggtgccccc cgaacgccag tgggcccggt   1440
tctatgtgaa aatttaccga gcagaggggc tgccccgtat gaacacaagc ctcatggcca   1500
atgtaaagaa ggctttcatc ggtgaaaaca aggacctcgt ggacccctac gtgcaagtct   1560
tctttgctgg ccagaagggc aagacttcag tgcagaagag cagctatgag cccctgtgga   1620
atgagcaggt cgtctttaca gacctcttcc ccccactctg caaacgcatg aaggtgcaga   1680
tccgagactc ggacaaggtc aacgacgtgg ccatcggcac ccacttcatt gacctgcgca   1740
agatttctaa tgacggagac aaaggcttcc tgcccacact gggcccagcc tgggtgaaca   1800
tgtacggctc cacacgtaac tacacgctgc tggatgagca tcaggacctg aacgagggcc   1860
tgggggaggg tgtgtccttc cggggcccggc tcctgctggg cctggctgtg gagatcgtag   1920
acacctccaa ccctgagctc accagctcca cagaggtgca ggtggagcag gccacgccca   1980
tctcggagag ctgtgcaggt aaaatggaag aattctttct ctttggagcc ttcctggagg   2040
cctcaatgat cgaccggaga aacggagaca agcccatcac ctttgaggtc accataggca   2100
actatgggaa cgaagttgat ggcctgtccc ggccccagcg gcctcggccc cggaaggagc   2160
cgggggatga ggaagaagta gacctgattc agaacgcaag tgatgacgag gccggtgatg   2220
ccggggacct ggcctcagtc tcctccactc caccaatgcg gccccaggtc accgacagga   2280
actacttcca tctgccctac ctggagcgaa agccctgcat ctacatcaag agctggtggc   2340
cggaccagcg ccgccgcctc tacaatgcca acatcatgga ccacattgcc gacaagctgg   2400
aagaaggcct gaacgacata caggagatga tcaaaacgga gaagtcctac cctgagcgtc   2460
gcctgcgggg cgtcctggag gagctgagct gtggctgctg ccgcttcctc tccctcgctg   2520
acaaggacca gggccactca tcccgcacca ggcttgaccg ggagcgcctc aagtcctgca   2580
tgagggagct ggaaaacatg gggcagcagg ccaggatgct gcgggcccag gtgaagcggc   2640
acacggtgcg ggacaagctg aggctgtgcc agaacttcct gcagaagctg cgcttcctgg   2700
cggacgagcc ccagcacagc attcccgaca tcttcatctg gatgatgagc aacaacaagc   2760
gtgtcgccta tgcccgtgtg ccctccaagg acctgctctt ctccatcgtg gaggaggaga   2820
ctggcaagga ctgcgccaag gtcaagacgc tcttccttaa gctgccaggg aagcggggct   2880
tcggctcggc aggctggaca gtgcaggcca aggtggagct gtacctgtgg ctgggcctca   2940
gcaaacagcg caaggagttc ctgtgcggcc tgccctgtgg cttccaggag gtcaaggcag   3000
cccagggcct gggcctgcat gccttcccac ccgtcagcct ggtctacacc aagaagcagg   3060
cgttccagct ccgagcgcac atgtaccagg cccgcagcct ctttgccgcc gacagcagcg   3120
```

-continued

```
gactctcaga ccccttttgcc cgcgtcttct tcatcaatca gagtcagtgc acagaggtgc   3180
tgaatgagac cctgtgtccc acctgggacc agatgctggt gttcgacaac ctggagctct   3240
atggtgaagc tcatgagctg agggacgatc cgcccatcat tgtcattgaa atctatgacc   3300
aggattccat gggcaaagct gacttcatgg gccggacctt cgccaaaccc ctggtgaaga   3360
tggcagacga ggcgtactgc ccaccccgct tcccacctca gctcgagtac taccagatct   3420
accgtggcaa cgccacagct ggagacctgc tggcggcctt cgagctgctg cagattggac   3480
cagcagggaa ggctgacctg ccccccatca atggcccggt ggacgtggac cgaggtccca   3540
tcatgcccgt gcccatgggc atccggcccg tgctcagcaa gtaccgagtg gaggtgctgt   3600
tctggggcct acgggaccta aagcgggtga acctggccca ggtggaccgg ccacgggtgg   3660
acatcgagtg tgcagggaag ggggtgcagt cgtccctgat ccacaattat aagaagaacc   3720
ccaacttcaa caccctcgtc aagtggtttg aagtggacct cccagagaac gagctgctgc   3780
acccgccctt gaacatccgt gtggtggact gccgggcctt cggtcgctac acactggtgg   3840
gctcccatgc cgtcagctcc ctgcgacgct tcatctaccg gcccccagac cgctcggccc   3900
ccagctggaa caccacggtc aggcttctcc ggcgctgccg tgtgctgtgc aatgggggct   3960
cctcctctca ctccacaggg gaggttgtgg tgactatgga gccagaggta cccatcaaga   4020
aactggagac catggtgaag ctggacgcga cttctgaagc tgttgtcaag gtggatgtgg   4080
ctgaggagga gaaggagaag aagaagaaga agaagggcac tgcggaggag ccagaggagg   4140
aggagccaga cgagagcatg ctggactggt ggtccaagta ctttgcctcc attgacacca   4200
tgaaggagca acttcgacaa caagagccct ctggaattga cttggaggag aaggaggaag   4260
tggacaatac cgagggcctg aaggggtcaa tgaagggcaa ggagaaggca agggctgcca   4320
aagaggagaa gaagaagaaa actcagagct ctggctctgg ccaggggtcc gaggcccccg   4380
agaagaagaa acccaagatt gatgagctta aggtataccc caaagagctg gagtccgagt   4440
ttgataactt tgaggactgg ctgcacactt tcaacttgct tcggggcaag accggggatg   4500
atgaggatgg ctccaccgag gaggagcgca ttgtgggacg cttcaagggc tccctctgcg   4560
tgtacaaagt gccactccca gaggacgtgt cccgggaagc cggctacgac tccacctacg   4620
gcatgttcca gggcatcccg agcaatgacc ccatcaatgt gctggtccga gtctatgtgg   4680
tccgggccac ggacctgcac cctgctgaca tcaacggcaa agctgacccc tacatcgcca   4740
tccggctagg caagactgac atccgcgaca aggagaacta catctccaag cagctcaacc   4800
ctgtctttgg gaagtccttt gacatcgagg cctccttccc catggaatcc atgctgacgg   4860
tggctgtgta tgactgggac ctggtgggca ctgatgacct cattggggaa accaagatcg   4920
acctggagaa ccgcttctac agcaagcacc gcgccacctg cggcatcgcc cagacctact   4980
ccacacatgg ctacaatatc tggcgggacc ccatgaagcc cagccagatc ctgacccgcc   5040
tctgcaaaga cggcaaagtg gacggccccc actttgggcc ccctgggaga gtgaaggtgg   5100
ccaaccgcgt cttcactggg ccctctgaga ttgaggacga gaacggtcag aggaagccca   5160
cagacgagca tgtggcgctg ttggccctga ggcactggga ggacatcccc cgcgcaggct   5220
gccgcctggt gccagagcat gtggagacga ggccgctgct caaccccgac aagccgggca   5280
tcgagcaggg ccgcctggag ctgtgggtgg acatgttccc catggacatg ccagcccctg   5340
ggacgcctct ggacatctca cctcggaagc ccaagaagta cgagctgcgg gtcatcatct   5400
ggaacacaga tgaggtggtc ttggaggacg acgacttctt cacaggggag aagtccagtg   5460
acatcttcgt gagggggtgg ctgaagggcc agcaggagga caagcaggac acagacgtcc   5520
```

actaccactc cctcactggc gagggcaact tcaactggcg ctacctgttc cccttcgact 5580
acctggcggc ggaggagaag atcgtcatct ccaagaagga gtccatgttc tcctgggacg 5640
agaccgagta caagatcccc gcgcggctca ccctgcagat ctgggatgcg gaccacttct 5700
ccgctgacga cttcctgggg gccatcgagc tggacctgaa ccggttcccg cggggcgcaa 5760
agacagccaa gcagtgcacc atggagatgg ccaccgggga ggtggacgtg cccctcgtgt 5820
ccatcttcaa gcaaaagcgc gtcaaaggct ggtggcccct cctggcccgc aatgagaacg 5880
atgagtttga gctcacgggc aaggtggagg ctgagctgca tttactgaca gcagaggagg 5940
cagagaagaa cccagtgggc ctggcccgca atgaacctga cccccctagag aaacccaacc 6000 ggcccgacac gagcttcatc tggttcctga accctctcaa gtcggctcgc tacttcttgt 6060
ggcacacgta tcgctggctg ctcctcaaac tgttgctgct cctgctgctg ctcctcctcc 6120
tcgccctgtt cctctactct gtgcctggct acctggtcaa gaaaatcctc ggggcctgag 6180
cccagtggcc tcctggccgg cccgacacgg ccttcgtctg gttcctcaac cctctcaagt 6240
ccatcaagta cctcatctgc acccggtaca agtggctcat catcaagatc gtgctggcgc 6300
tgttggggct gctcatgttg gggctcttcc tctacagcct ccctggctac atggtcaaaa 6360
agctccttgg ggcatgaagg ccgccagctc ccgccagccg ctccccagcc ctgccgcatt 6420
tcctttcagt ggcttggact ctttcccatc tcccctgggg agcctgagga gcccagcgtc 6480
cactcttcat gccttgggcc gagcctgcct cctgcttgcg gggggccgcct gtcctcactg 6540 ccccaggctg cggcttgccc agtcccgccc ctctgacccc tgcctgtggg ctggggagcc 6600
ttggatgggg tggggacctg gaatgggtct ctcttgcccc acctggctga ggcgccaccc 6660
ttcttcaggc ccaggctcca gaggaagact cctgaaaccc tccccaggtc ttccaagtac 6720
aggattgaag ctttagtgaa attaaccaag gaccatgggt cagtgcccag ggctttaaaa 6780
agaatgaacg agcaaaaggt atccccgccg tgacccctgc agatagcacc ggtctttgat 6840
ccgcagcagg ggccagaccc tgcccacaag tcccagcgcg gctgcttctg ccactgctgg 6900
gctccacttg gctcctctca cttcccaggg ggtcgcctgt cctgcctgtg ggtttccatg 6960
gcttcccaga gctccctctg ccccagccag cgcctccagg cccagctgag gagctgtgag 7020
aagcagcaga ggggactccc catcccgggc acaccctgtc ctcccacccc tgcccccttg 7080
cccttccagc cctttcagct gcagctggga gctggcccgt caagtgctgc ccctgcctgt 7140
gtctgggttt ctgttggctg tttttctttt cttgagtggt gatttttctc taaataaaag 7200
aagtcaagca ctga 7214

<210> SEQ ID NO 5
<211> LENGTH: 1997
<212> TYPE: PRT
<213> ORGANISM: Homo sapiens

<400> SEQUENCE: 5

Met Ala Leu Leu Ile His Leu Lys Thr Val Ser Glu Leu Arg Gly Arg
1 5 10 15

Gly Asp Arg Ile Ala Lys Val Thr Phe Arg Gly Gln Ser Phe Tyr Ser
20 25 30

Arg Val Leu Glu Asn Cys Glu Asp Val Ala Asp Phe Asp Glu Thr Phe
35 40 45

Arg Trp Pro Val Ala Ser Ser Ile Asp Arg Asn Glu Met Leu Glu Ile
50 55 60

-continued

```
Gln Val Phe Asn Tyr Ser Lys Val Phe Ser Asn Lys Leu Ile Gly Thr
65                  70                  75                  80

Phe Arg Met Val Leu Gln Lys Val Val Glu Glu Ser His Val Glu Val
                85                  90                  95

Thr Asp Thr Leu Ile Asp Asp Asn Asn Ala Ile Ile Lys Thr Ser Leu
            100                 105                 110

Cys Val Glu Val Arg Tyr Gln Ala Thr Asp Gly Thr Val Gly Ser Trp
        115                 120                 125

Asp Asp Gly Asp Phe Leu Gly Asp Glu Ser Leu Gln Glu Glu Glu Lys
    130                 135                 140

Asp Ser Gln Glu Thr Asp Gly Leu Leu Pro Gly Ser Arg Pro Ser Ser
145                 150                 155                 160

Arg Pro Pro Gly Glu Lys Ser Phe Arg Arg Ala Gly Arg Ser Val Phe
                165                 170                 175

Ser Ala Met Lys Leu Gly Lys Asn Arg Ser His Lys Glu Glu Pro Gln
            180                 185                 190

Arg Pro Asp Glu Pro Ala Val Leu Glu Met Glu Asp Leu Asp His Leu
        195                 200                 205

Ala Ile Arg Leu Gly Asp Gly Leu Asp Pro Asp Ser Val Ser Leu Ala
    210                 215                 220

Ser Val Thr Ala Leu Thr Thr Asn Val Ser Asn Lys Arg Ser Lys Pro
225                 230                 235                 240

Asp Ile Lys Met Glu Pro Ser Ala Gly Arg Pro Met Asp Tyr Gln Val
                245                 250                 255

Ser Ile Thr Val Ile Glu Ala Arg Gln Leu Val Gly Leu Asn Met Asp
            260                 265                 270

Pro Val Val Cys Val Glu Val Gly Asp Asp Lys Lys Tyr Thr Ser Met
        275                 280                 285

Lys Glu Ser Thr Asn Cys Pro Tyr Tyr Asn Glu Tyr Phe Val Phe Asp
    290                 295                 300

Phe His Val Ser Pro Asp Val Met Phe Asp Lys Ile Ile Lys Ile Ser
305                 310                 315                 320

Val Ile His Ser Lys Asn Leu Leu Arg Ser Gly Thr Leu Val Gly Ser
                325                 330                 335

Phe Lys Met Asp Val Gly Thr Val Tyr Ser Gln Pro Glu His Gln Phe
            340                 345                 350

His His Lys Trp Ala Ile Leu Ser Asp Pro Asp Asp Ile Ser Ser Gly
        355                 360                 365

Leu Lys Gly Tyr Val Lys Cys Asp Val Ala Val Val Gly Lys Gly Asp
    370                 375                 380

Asn Ile Lys Thr Pro His Lys Ala Asn Glu Thr Asp Glu Asp Asp Ile
385                 390                 395                 400

Glu Gly Asn Leu Leu Leu Pro Glu Gly Val Pro Pro Glu Arg Gln Trp
                405                 410                 415

Ala Arg Phe Tyr Val Lys Ile Tyr Arg Ala Glu Gly Leu Pro Arg Met
            420                 425                 430

Asn Thr Ser Leu Met Ala Asn Val Lys Lys Ala Phe Ile Gly Glu Asn
        435                 440                 445

Lys Asp Leu Val Asp Pro Tyr Val Gln Val Phe Phe Ala Gly Gln Lys
    450                 455                 460

Gly Lys Thr Ser Val Gln Lys Ser Ser Tyr Glu Pro Leu Trp Asn Glu
465                 470                 475                 480

Gln Val Val Phe Thr Asp Leu Phe Pro Pro Leu Cys Lys Arg Met Lys
```

-continued

```
                485                 490                 495

Val Gln Ile Arg Asp Ser Asp Lys Val Asn Asp Val Ala Ile Gly Thr
            500                 505                 510

His Phe Ile Asp Leu Arg Lys Ile Ser Asn Asp Gly Asp Lys Gly Phe
        515                 520                 525

Leu Pro Thr Leu Gly Pro Ala Trp Val Asn Met Tyr Gly Ser Thr Arg
    530                 535                 540

Asn Tyr Thr Leu Leu Asp Glu His Gln Asp Leu Asn Glu Gly Leu Gly
545                 550                 555                 560

Glu Gly Val Ser Phe Arg Ala Arg Leu Leu Leu Gly Leu Ala Val Glu
                565                 570                 575

Ile Val Asp Thr Ser Asn Pro Glu Leu Thr Ser Ser Thr Glu Val Gln
            580                 585                 590

Val Glu Gln Ala Thr Pro Ile Ser Glu Ser Cys Ala Gly Lys Met Glu
        595                 600                 605

Glu Phe Phe Leu Phe Gly Ala Phe Leu Glu Ala Ser Met Ile Asp Arg
    610                 615                 620

Arg Asn Gly Asp Lys Pro Ile Thr Phe Glu Val Thr Ile Gly Asn Tyr
625                 630                 635                 640

Gly Asn Glu Val Asp Gly Leu Ser Arg Pro Gln Arg Pro Arg Pro Arg
                645                 650                 655

Lys Glu Pro Gly Asp Glu Glu Glu Val Asp Leu Ile Gln Asn Ala Ser
            660                 665                 670

Asp Asp Glu Ala Gly Asp Ala Gly Asp Leu Ala Ser Val Ser Ser Thr
        675                 680                 685

Pro Pro Met Arg Pro Gln Val Thr Asp Arg Asn Tyr Phe His Leu Pro
    690                 695                 700

Tyr Leu Glu Arg Lys Pro Cys Ile Tyr Ile Lys Ser Trp Trp Pro Asp
705                 710                 715                 720

Gln Arg Arg Arg Leu Tyr Asn Ala Asn Ile Met Asp His Ile Ala Asp
                725                 730                 735

Lys Leu Glu Glu Gly Leu Asn Asp Ile Gln Glu Met Ile Lys Thr Glu
            740                 745                 750

Lys Ser Tyr Pro Glu Arg Arg Leu Arg Gly Val Leu Glu Glu Leu Ser
        755                 760                 765

Cys Gly Cys Cys Arg Phe Leu Ser Leu Ala Asp Lys Asp Gln Gly His
    770                 775                 780

Ser Ser Arg Thr Arg Leu Asp Arg Glu Arg Leu Lys Ser Cys Met Arg
785                 790                 795                 800

Glu Leu Glu Asn Met Gly Gln Gln Ala Arg Met Leu Arg Ala Gln Val
                805                 810                 815

Lys Arg His Thr Val Arg Asp Lys Leu Arg Leu Cys Gln Asn Phe Leu
            820                 825                 830

Gln Lys Leu Arg Phe Leu Ala Asp Glu Pro Gln His Ser Ile Pro Asp
        835                 840                 845

Ile Phe Ile Trp Met Met Ser Asn Asn Lys Arg Val Ala Tyr Ala Arg
    850                 855                 860

Val Pro Ser Lys Asp Leu Leu Phe Ser Ile Val Glu Glu Glu Thr Gly
865                 870                 875                 880

Lys Asp Cys Ala Lys Val Lys Thr Leu Phe Leu Lys Leu Pro Gly Lys
                885                 890                 895

Arg Gly Phe Gly Ser Ala Gly Trp Thr Val Gln Ala Lys Val Glu Leu
            900                 905                 910
```

-continued

Tyr Leu Trp Leu Gly Leu Ser Lys Gln Arg Lys Glu Phe Leu Cys Gly
915 920 925

Leu Pro Cys Gly Phe Gln Glu Val Lys Ala Ala Gln Gly Leu Gly Leu
930 935 940

His Ala Phe Pro Pro Val Ser Leu Val Tyr Thr Lys Lys Gln Ala Phe
945 950 955 960

Gln Leu Arg Ala His Met Tyr Gln Ala Arg Ser Leu Phe Ala Ala Asp
965 970 975

Ser Ser Gly Leu Ser Asp Pro Phe Ala Arg Val Phe Phe Ile Asn Gln
980 985 990

Ser Gln Cys Thr Glu Val Leu Asn Glu Thr Leu Cys Pro Thr Trp Asp
995 1000 1005

Gln Met Leu Val Phe Asp Asn Leu Glu Leu Tyr Gly Glu Ala His
1010 1015 1020

Glu Leu Arg Asp Asp Pro Pro Ile Ile Val Ile Glu Ile Tyr Asp
1025 1030 1035

Gln Asp Ser Met Gly Lys Ala Asp Phe Met Gly Arg Thr Phe Ala
1040 1045 1050

Lys Pro Leu Val Lys Met Ala Asp Glu Ala Tyr Cys Pro Pro Arg
1055 1060 1065

Phe Pro Pro Gln Leu Glu Tyr Tyr Gln Ile Tyr Arg Gly Asn Ala
1070 1075 1080

Thr Ala Gly Asp Leu Leu Ala Ala Phe Glu Leu Leu Gln Ile Gly
1085 1090 1095

Pro Ala Gly Lys Ala Asp Leu Pro Pro Ile Asn Gly Pro Val Asp
1100 1105 1110

Val Asp Arg Gly Pro Ile Met Pro Val Pro Met Gly Ile Arg Pro
1115 1120 1125

Val Leu Ser Lys Tyr Arg Val Glu Val Leu Phe Trp Gly Leu Arg
1130 1135 1140

Asp Leu Lys Arg Val Asn Leu Ala Gln Val Asp Arg Pro Arg Val
1145 1150 1155

Asp Ile Glu Cys Ala Gly Lys Gly Val Gln Ser Ser Leu Ile His
1160 1165 1170

Asn Tyr Lys Lys Asn Pro Asn Phe Asn Thr Leu Val Lys Trp Phe
1175 1180 1185

Glu Val Asp Leu Pro Glu Asn Glu Leu Leu His Pro Pro Leu Asn
1190 1195 1200

Ile Arg Val Val Asp Cys Arg Ala Phe Gly Arg Tyr Thr Leu Val
1205 1210 1215

Gly Ser His Ala Val Ser Ser Leu Arg Arg Phe Ile Tyr Arg Pro
1220 1225 1230

Pro Asp Arg Ser Ala Pro Ser Trp Asn Thr Thr Val Arg Leu Leu
1235 1240 1245

Arg Arg Cys Arg Val Leu Cys Asn Gly Gly Ser Ser Ser His Ser
1250 1255 1260

Thr Gly Glu Val Val Val Thr Met Glu Pro Glu Val Pro Ile Lys
1265 1270 1275

Lys Leu Glu Thr Met Val Lys Leu Asp Ala Thr Ser Glu Ala Val
1280 1285 1290

Val Lys Val Asp Val Ala Glu Glu Glu Lys Glu Lys Lys Lys Lys
1295 1300 1305

-continued

Lys Lys Gly Thr Ala Glu Glu Pro Glu Glu Glu Glu Pro Asp Glu
1310 1315 1320

Ser Met Leu Asp Trp Trp Ser Lys Tyr Phe Ala Ser Ile Asp Thr
1325 1330 1335

Met Lys Glu Gln Leu Arg Gln Gln Glu Pro Ser Gly Ile Asp Leu
1340 1345 1350

Glu Glu Lys Glu Glu Val Asp Asn Thr Glu Gly Leu Lys Gly Ser
1355 1360 1365

Met Lys Gly Lys Glu Lys Ala Arg Ala Ala Lys Glu Glu Lys Lys
1370 1375 1380

Lys Lys Thr Gln Ser Ser Gly Ser Gly Gln Gly Ser Glu Ala Pro
1385 1390 1395

Glu Lys Lys Lys Pro Lys Ile Asp Glu Leu Lys Val Tyr Pro Lys
1400 1405 1410

Glu Leu Glu Ser Glu Phe Asp Asn Phe Glu Asp Trp Leu His Thr
1415 1420 1425

Phe Asn Leu Leu Arg Gly Lys Thr Gly Asp Asp Glu Asp Gly Ser
1430 1435 1440

Thr Glu Glu Glu Arg Ile Val Gly Arg Phe Lys Gly Ser Leu Cys
1445 1450 1455

Val Tyr Lys Val Pro Leu Pro Glu Asp Val Ser Arg Glu Ala Gly
1460 1465 1470

Tyr Asp Ser Thr Tyr Gly Met Phe Gln Gly Ile Pro Ser Asn Asp
1475 1480 1485

Pro Ile Asn Val Leu Val Arg Val Tyr Val Val Arg Ala Thr Asp
1490 1495 1500

Leu His Pro Ala Asp Ile Asn Gly Lys Ala Asp Pro Tyr Ile Ala
1505 1510 1515

Ile Arg Leu Gly Lys Thr Asp Ile Arg Asp Lys Glu Asn Tyr Ile
1520 1525 1530

Ser Lys Gln Leu Asn Pro Val Phe Gly Lys Ser Phe Asp Ile Glu
1535 1540 1545

Ala Ser Phe Pro Met Glu Ser Met Leu Thr Val Ala Val Tyr Asp
1550 1555 1560

Trp Asp Leu Val Gly Thr Asp Asp Leu Ile Gly Glu Thr Lys Ile
1565 1570 1575

Asp Leu Glu Asn Arg Phe Tyr Ser Lys His Arg Ala Thr Cys Gly
1580 1585 1590

Ile Ala Gln Thr Tyr Ser Thr His Gly Tyr Asn Ile Trp Arg Asp
1595 1600 1605

Pro Met Lys Pro Ser Gln Ile Leu Thr Arg Leu Cys Lys Asp Gly
1610 1615 1620

Lys Val Asp Gly Pro His Phe Gly Pro Pro Gly Arg Val Lys Val
1625 1630 1635

Ala Asn Arg Val Phe Thr Gly Pro Ser Glu Ile Glu Asp Glu Asn
1640 1645 1650

Gly Gln Arg Lys Pro Thr Asp Glu His Val Ala Leu Leu Ala Leu
1655 1660 1665

Arg His Trp Glu Asp Ile Pro Arg Ala Gly Cys Arg Leu Val Pro
1670 1675 1680

Glu His Val Glu Thr Arg Pro Leu Leu Asn Pro Asp Lys Pro Gly
1685 1690 1695

Ile Glu Gln Gly Arg Leu Glu Leu Trp Val Asp Met Phe Pro Met

```
    1700                1705                1710

Asp Met  Pro Ala Pro Gly Thr  Pro Leu Asp Ile Ser  Pro Arg Lys
    1715                1720                1725

Pro Lys  Lys Tyr Glu Leu Arg  Val Ile Ile Trp Asn  Thr Asp Glu
    1730                1735                1740

Val Val  Leu Glu Asp Asp Asp  Phe Phe Thr Gly Glu  Lys Ser Ser
    1745                1750                1755

Asp Ile  Phe Val Arg Gly Trp  Leu Lys Gly Gln Gln  Glu Asp Lys
    1760                1765                1770

Gln Asp  Thr Asp Val His Tyr  His Ser Leu Thr Gly  Glu Gly Asn
    1775                1780                1785

Phe Asn  Trp Arg Tyr Leu Phe  Pro Phe Asp Tyr Leu  Ala Ala Glu
    1790                1795                1800

Glu Lys  Ile Val Ile Ser Lys  Lys Glu Ser Met Phe  Ser Trp Asp
    1805                1810                1815

Glu Thr  Glu Tyr Lys Ile Pro  Ala Arg Leu Thr Leu  Gln Ile Trp
    1820                1825                1830

Asp Ala  Asp His Phe Ser Ala  Asp Asp Phe Leu Gly  Ala Ile Glu
    1835                1840                1845

Leu Asp  Leu Asn Arg Phe Pro  Arg Gly Ala Lys Thr  Ala Lys Gln
    1850                1855                1860

Cys Thr  Met Glu Met Ala Thr  Gly Glu Val Asp Val  Pro Leu Val
    1865                1870                1875

Ser Ile  Phe Lys Gln Lys Arg  Val Lys Gly Trp Trp  Pro Leu Leu
    1880                1885                1890

Ala Arg  Asn Glu Asn Asp Glu  Phe Glu Leu Thr Gly  Lys Val Glu
    1895                1900                1905

Ala Glu  Leu His Leu Leu Thr  Ala Glu Glu Ala Glu  Lys Asn Pro
    1910                1915                1920

Val Gly  Leu Ala Arg Asn Glu  Pro Asp Pro Leu Glu  Lys Pro Asn
    1925                1930                1935

Arg Pro  Asp Thr Ser Phe Ile  Trp Phe Leu Asn Pro  Leu Lys Ser
    1940                1945                1950

Ala Arg  Tyr Phe Leu Trp His  Thr Tyr Arg Trp Leu  Leu Leu Lys
    1955                1960                1965

Leu Leu  Leu Leu Leu Leu Leu  Leu Leu Leu Leu Ala  Leu Phe Leu
    1970                1975                1980

Tyr Ser  Val Pro Gly Tyr Leu  Val Lys Lys Ile Leu  Gly Ala
    1985                1990                1995
```

<210> SEQ ID NO 6
<211> LENGTH: 2290
<212> TYPE: DNA
<213> ORGANISM: Homo sapiens

<400> SEQUENCE: 6

```
gttgcggccc cgcagcgccc gcgcgctcct ctccccgact cggagcccct cggcggcgcc     60

cggcccagga cccgcctagg agcgcaggag ccccagcgca gagaccccaa cgccgagacc    120

cccgccccgg ccccgccgcg cttcctcccg acgcagagca aaccgcccag agtagaagat    180

ggattggggc acgctgcaga cgatcctggg gggtgtgaac aaacactcca ccagcattgg    240

aaagatctgg ctcaccgtcc tcttcatttt tcgcattatg atcctcgttg tggctgcaaa    300

ggaggtgtgg ggagatgagc aggccgactt tgtctgcaac accctgcagc caggctgcaa    360
```

```
gaacgtgtgc tacgatcact acttccccat ctcccacatc cggctatggg ccctgcagct    420
gatcttcgtg tccacgccag cgctcctagt ggccatgcac gtggcctacc ggagacatga    480
gaagaagagg aagttcatca agggggagat aaagagtgaa tttaaggaca tcgaggagat    540
caaaacccag aaggtccgca tcgaaggctc cctgtggtgg acctacacaa gcagcatctt    600
cttccgggtc atcttcgaag ccgccttcat gtacgtcttc tatgtcatgt acgacggctt    660
ctccatgcag cggctggtga agtgcaacgc ctggccttgt cccaacactg tggactgctt    720
tgtgtcccgg cccacggaga agactgtctt cacagtgttc atgattgcag tgtctggaat    780
ttgcatcctg ctgaatgtca ctgaattgtg ttatttgcta attagatatt gttctgggaa    840
gtcaaaaaag ccagtttaac gcattgccca gttgttagat taagaaatag acagcatgag    900
agggatgagg caacccgtgc tcagctgtca aggctcagtc gctagcattt cccaacacaa    960
agattctgac cttaaatgca accatttgaa acccctgtag gcctcaggtg aaactccaga   1020
tgccacaatg gagctctgct cccctaaagc ctcaaaacaa aggcctaatt ctatgcctgt   1080
cttaatttc tttcacttaa gttagttcca ctgagacccc aggctgttag ggttattgg   1140
tgtaaggtac tttcatattt taaacagagg atatcggcat ttgtttcttt ctctgaggac   1200
aagagaaaaa agccaggttc cacagaggac acagagaagg tttgggtgtc ctcctggggt   1260
tctttttgcc aactttcccc acgttaaagg tgaacattgg ttctttcatt tgctttggaa   1320
gttttaatct ctaacagtgg acaaagttac cagtgcctta aactctgtta cactttttgg   1380
aagtgaaaac tttgtagtat gataggttat tttgatgtaa agatgttctg gataccatta   1440
tatgttcccc ctgtttcaga ggctcagatt gtaatatgta aatggtatgt cattcgctac   1500
tatgatttaa tttgaaatat ggtcttttgg ttatgaatac tttgcagcac agctgagagg   1560
ctgtctgttg tattcattgt ggtcatagca cctaacaaca ttgtagcctc aatcgagtga   1620
gacagactag aagttcctag tgatggctta tgatagcaaa tggcctcatg tcaaatattt   1680
agatgtaatt ttgtgtaaga aatacagact ggatgtacca ccaactacta cctgtaatga   1740
caggcctgtc caacacatct cccttttcca tgactgtggt agccagcatc ggaaagaacg   1800
ctgatttaaa gaggtcgctt gggaatttta ttgacacagt accatttaat ggggaggaca   1860
aaatggggca ggggagggag aagtttctgt cgttaaaaac agatttggaa agactggact   1920
ctaaagtctg ttgattaaag atgagctttg tctacttcaa aagtttgttt gcttacccct   1980
tcagcctcca attttttaag tgaaaatata gctaataaca tgtgaaaaga atagaagcta   2040
aggtttagat aaatattgag cagatctata ggaagattga acctgaatat tgccattatg   2100
cttgacatgg tttccaaaaa atggtactcc acatatttca gtgagggtaa gtattttcct   2160
gttgtcaaga atagcattgt aaaagcattt tgtaataata aagaatagct ttaatgatat   2220
gcttgtaact aaaataattt tgtaatgtat caaatacatt taaaacatta aaatataatc   2280
tctataataa                                                          2290
```

<210> SEQ ID NO 7
<211> LENGTH: 226
<212> TYPE: PRT
<213> ORGANISM: Homo sapiens

<400> SEQUENCE: 7

```
Met Asp Trp Gly Thr Leu Gln Thr Ile Leu Gly Gly Val Asn Lys His
1               5                   10                  15

Ser Thr Ser Ile Gly Lys Ile Trp Leu Thr Val Leu Phe Ile Phe Arg
            20                  25                  30
```

```
Ile Met Ile Leu Val Val Ala Ala Lys Glu Val Trp Gly Asp Glu Gln
        35                  40                  45

Ala Asp Phe Val Cys Asn Thr Leu Gln Pro Gly Cys Lys Asn Val Cys
    50                  55                  60

Tyr Asp His Tyr Phe Pro Ile Ser His Ile Arg Leu Trp Ala Leu Gln
65                  70                  75                  80

Leu Ile Phe Val Ser Thr Pro Ala Leu Leu Val Ala Met His Val Ala
                85                  90                  95

Tyr Arg Arg His Glu Lys Lys Arg Lys Phe Ile Lys Gly Glu Ile Lys
            100                 105                 110

Ser Glu Phe Lys Asp Ile Glu Glu Ile Lys Thr Gln Lys Val Arg Ile
        115                 120                 125

Glu Gly Ser Leu Trp Trp Thr Tyr Thr Ser Ser Ile Phe Phe Arg Val
    130                 135                 140

Ile Phe Glu Ala Ala Phe Met Tyr Val Phe Tyr Val Met Tyr Asp Gly
145                 150                 155                 160

Phe Ser Met Gln Arg Leu Val Lys Cys Asn Ala Trp Pro Cys Pro Asn
                165                 170                 175

Thr Val Asp Cys Phe Val Ser Arg Pro Thr Glu Lys Thr Val Phe Thr
            180                 185                 190

Val Phe Met Ile Ala Val Ser Gly Ile Cys Ile Leu Leu Asn Val Thr
        195                 200                 205

Glu Leu Cys Tyr Leu Leu Ile Arg Tyr Cys Ser Gly Lys Ser Lys Lys
    210                 215                 220

Pro Val
225
```

<210> SEQ ID NO 8
<211> LENGTH: 2105
<212> TYPE: DNA
<213> ORGANISM: Homo sapiens

<400> SEQUENCE: 8

```
gtcatggcag cgccaggcgg caggtcggag ccgccgcagc tccccgagta cagctgcagc      60

tacatggtgt cgcggccggt ctacagcgag ctcgctttcc agcaacagca cgagcggcgc     120

ctgcaggagc gcaagacgct gcgggagagc ctggccaagt gctgcagttg ttcaagaaag     180

agagcctttg gtgtgctaaa gactcttgtg cccatcttgg agtggctccc caaataccga     240

gtcaaggaat ggctgcttag tgacgtcatt tcgggagtta gtactgggct agtggccacg     300

ctgcaaggga tggcatatgc cctactagct gcagttcctg tcggatatgg tctctactct     360

gctttttcc ctatcctgac atactttatc tttggaacat caagacatat ctcagttgga     420

ccttttccag tggtgagttt aatggtggga tctgttgttc tgagcatggc ccccgacgaa     480

cactttctcg tatccagcag caatggaact gtattaaata ctactatgat agacactgca     540

gctagagata cagctagagt cctgattgcc agtgccctga ctctgctggt tggaattata     600

cagttgatat ttggtggctt gcagattgga ttcatagtga ggtacttggc agatcctttg     660

gttggtggct tcacaacagc tgctgccttc caagtgctgg tctcacagct aaagattgtc     720

ctcaatgttt caaccaaaaa ctacaatgga gttctctcta ttatctatac gctggttgag     780

atttttcaaa atattggtga taccaatctt gctgatttca ctgctggatt gctcaccatt     840

gtcgtctgta tggcagttaa ggaattaaat gatcggttta gacacaaaat cccagtccct     900

attcctatag aagtaattgt gacgataatt gctactgcca tttcatatgg agccaacctg     960
```

```
gaaaaaaatt acaatgctgg cattgttaaa tccatcccaa gggggttttt gcctcctgaa   1020

cttccacctg tgagcttgtt ctcggagatg ctggctgcat cattttccat cgctgtggtg   1080

gcttatgcta ttgcagtgtc agtaggaaaa gtatatgcca ccaagtatga ttacaccatc   1140

gatgggaacc aggaattcat tgcctttggg atcagcaaca tcttctcagg attcttctct   1200

tgttttgtgg ccaccactgc tctttcccgc acggccgtcc aggagagcac tggaggaaag   1260

acacagagct tctaatcttc atcttggctc tgccccagct gtctcaacag agaattcatt   1320

ggtcatctaa tcaaacgaga gagtagtccc caccccctca gcctctctcc taactagtat   1380

ggatcttagg agagctattt ttgccagcga aggtaaagtt tctgaagctt cctttaccc    1440

ctgctattgc cccgttactc catagtcact gtttcaggct gccttggggc aaagctctga   1500

gcctgcctcc gtggaactgt cagaggaggc aggagacaca atcccacctc tcaatgtgca   1560

aatgtggcat ttcgaatttg caataggatg agtaaattta ttttctctga gactttaatg   1620

agaccatgtg ctacaagtac gaagtgttat cagagttgct attatagctg cagcttcaat   1680

aatgcagaaa aatcagctat gtgccatgag aatttatttc ccaagaatac gacaatgatc   1740

tctgttgttg ggaaaggggg gattggtcca tgtttcctgc catggtaaat aactagaagc   1800

ttggcctgaa tggacgccga aaccgcaggt gtgtactatc accaaataaa atccctgtca   1860

aactggcttt aatttcatag gatcagtccc catattttct ttaacttctc tgccatagca   1920

tatatagatg ccatttttgt tcagttttgt ggcttgagca aataactatc actttctcg    1980

acagtattga gcagaagggg gagacaggga agtatgaagt gtgtctgtga acaggctgtc   2040

tcatacacac atccagtgag ctggaagaca caagggagaa ggacgaatcc ttttcatagg   2100

aggtg                                                               2105


<210> SEQ ID NO 9
<211> LENGTH: 423
<212> TYPE: PRT
<213> ORGANISM: Homo sapiens

<400> SEQUENCE: 9

Met Ala Ala Pro Gly Gly Arg Ser Glu Pro Pro Gln Leu Pro Glu Tyr
1               5                   10                  15

Ser Cys Ser Tyr Met Val Ser Arg Pro Val Tyr Ser Glu Leu Ala Phe
            20                  25                  30

Gln Gln Gln His Glu Arg Arg Leu Gln Glu Arg Lys Thr Leu Arg Glu
        35                  40                  45

Ser Leu Ala Lys Cys Cys Ser Cys Ser Arg Lys Arg Ala Phe Gly Val
    50                  55                  60

Leu Lys Thr Leu Val Pro Ile Leu Glu Trp Leu Pro Lys Tyr Arg Val
65                  70                  75                  80

Lys Glu Trp Leu Leu Ser Asp Val Ile Ser Gly Val Ser Thr Gly Leu
                85                  90                  95

Val Ala Thr Leu Gln Gly Met Ala Tyr Ala Leu Leu Ala Ala Val Pro
            100                 105                 110

Val Gly Tyr Gly Leu Tyr Ser Ala Phe Phe Pro Ile Leu Thr Tyr Phe
        115                 120                 125

Ile Phe Gly Thr Ser Arg His Ile Ser Val Gly Pro Phe Pro Val Val
    130                 135                 140

Ser Leu Met Val Gly Ser Val Val Leu Ser Met Ala Pro Asp Glu His
145                 150                 155                 160
```

Phe Leu Val Ser Ser Ser Asn Gly Thr Val Leu Asn Thr Thr Met Ile
                165                 170                 175

Asp Thr Ala Ala Arg Asp Thr Ala Arg Val Leu Ile Ala Ser Ala Leu
            180                 185                 190

Thr Leu Leu Val Gly Ile Ile Gln Leu Ile Phe Gly Gly Leu Gln Ile
        195                 200                 205

Gly Phe Ile Val Arg Tyr Leu Ala Asp Pro Leu Val Gly Gly Phe Thr
    210                 215                 220

Thr Ala Ala Ala Phe Gln Val Leu Val Ser Gln Leu Lys Ile Val Leu
225                 230                 235                 240

Asn Val Ser Thr Lys Asn Tyr Asn Gly Val Leu Ser Ile Ile Tyr Thr
                245                 250                 255

Leu Val Glu Ile Phe Gln Asn Ile Gly Asp Thr Asn Leu Ala Asp Phe
            260                 265                 270

Thr Ala Gly Leu Leu Thr Ile Val Val Cys Met Ala Val Lys Glu Leu
        275                 280                 285

Asn Asp Arg Phe Arg His Lys Ile Pro Val Pro Ile Pro Ile Glu Val
    290                 295                 300

Ile Val Thr Ile Ile Ala Thr Ala Ile Ser Tyr Gly Ala Asn Leu Glu
305                 310                 315                 320

Lys Asn Tyr Asn Ala Gly Ile Val Lys Ser Ile Pro Arg Gly Phe Leu
                325                 330                 335

Pro Pro Glu Leu Pro Pro Val Ser Leu Phe Ser Glu Met Leu Ala Ala
            340                 345                 350

Ser Phe Ser Ile Ala Val Val Ala Tyr Ala Ile Ala Val Ser Val Gly
        355                 360                 365

Lys Val Tyr Ala Thr Lys Tyr Asp Tyr Thr Ile Asp Gly Asn Gln Glu
    370                 375                 380

Phe Ile Ala Phe Gly Ile Ser Asn Ile Phe Ser Gly Phe Phe Ser Cys
385                 390                 395                 400

Phe Val Ala Thr Thr Ala Leu Ser Arg Thr Ala Val Gln Glu Ser Thr
                405                 410                 415

Gly Gly Lys Thr Gln Ser Phe
            420

<210> SEQ ID NO 10
<211> LENGTH: 3491
<212> TYPE: DNA
<213> ORGANISM: Homo sapiens

<400> SEQUENCE: 10
aattgtggct atagccgcct cgatcgctgt ctccccagcc tcgccgcggc cgctccggga 60
cgcgcccgcc cgccgcccgg ctctcccccc ctttgggctg ctgctgctgc tgctgtgact 120
gctgctgcga gaggaggagg aggaggagga agcagcgggg gggggagcgg ggggtggggg 180
gggagaccaa gaagtacagt tgggagcgag ggagcttcac ccccggggcg gtggttgttt 240
ctttttcttt tctttctttt ttcttttcct tttttttttt ttttctaatt cctgaggggt 300
ggttgctgct tttgctacat gacttgccag cgcccgagcc tgcggtccaa ctgcgctgct 360
gccggagcgc tcagtgccgc cgctgccgcc cgcgcccccc gcgccccgtt cggcacccac 420
cggtcgccgc cgcccgccgc gccgctgtcc cgctcccgcg ccgccgccgc cgtttccccc 480
cgacgactgg gtgatgctgg acatgggaga taggaaagag gtgaaaatga tccccaagtc 540
ctcgttcagc atcaacagcc tggtgcccga ggcggtccag aacgacaacc accacgcgag 600

-continued

```
ccacggccac cacaacagcc accaccccca gcaccaccac caccaccacc accatcacca    660
ccacccgccg ccgcccgccc cgcaaccgcc gccgccgccg cagcagcagc agccgccgcc    720
gccgccgccc ccggcaccgc agcccccccca gacgcggggc gccccggccg ccgacgacga   780
caagggcccc cagcagctgc tgctcccgcc gccgccaccg ccaccaccgg ccgccgccct    840
ggacggggct aaagcggacg ggctgggcgg caagggcgag ccgggcggcg ggccggggga    900
gctggcgccc gtcgggccgg acgagaagga gaagggcgcc ggcgccgggg gggaggagaa    960
gaagggggcg ggcgagggcg gcaaggacgg ggaggggggc aaggagggcg agaagaagaa   1020
cggcaagtac gagaagccgc cgttcagcta caacgcgctc atcatgatgg ccatccggca   1080
gagccccgag aagcggctca cgctcaacgg catctacgag ttcatcatga agaacttccc   1140
ttactaccgc gagaacaagc agggctggca gaactccatc cgccacaatc tgtccctcaa   1200
caagtgcttc gtgaaggtgc cgcgccacta cgacgacccg ggcaagggca actactggat   1260
gctggacccg tcgagcgacg acgtgttcat cggcggcacc acgggcaagc tgcggcgccg   1320
ctccaccacc tcgcgggcca agctggcctt caagcgcggt gcgcgcctca cctccaccgg   1380
cctcaccttc atggaccgcg ccggctccct ctactggccc atgtcgccct tcctgtccct   1440
gcaccacccc cgcgccagca gcactttgag ttacaacggc accacgtcgg cctaccccag   1500
ccaccccatg ccctacagct ccgtgttgac tcagaactcg ctgggcaaca accactcctt   1560
ctccaccgcc aacggcctga gcgtggaccg gctggtcaac ggggagatcc cgtacgccac   1620
gcaccacctc acggccgccg cgctagccgc ctcggtgccc tgcggcctgt cggtgccctg   1680
ctctgggacc tactccctca accccctgctc cgtcaacctg ctcgcgggcc agaccagtta   1740
ctttttcccc cacgtcccgc acccgtcaat gacttcgcag agcagcacgt ccatgagcgc   1800
cagggccgcg tcctcctcca cgtcgccgca ggccccctcg accctgccct gtgagtcttt   1860
aagaccctct ttgccaagtt ttacgacggg actgtctggg ggactgtctg attatttcac   1920
acatcaaaat caggggtctt cttccaaccc tttaatacat taacatccct gggaccagac   1980
tgtaagtgaa cgttttacac acatttgcat tgtaaatgat aattaaaaaa ataagtccag   2040
gtatttttta ttaagccccc ccctcccatt tctgtacgtt tgttcagtct ctagggttgt   2100
ttattattct aacaaggtgt ggagtgtcag cgaggtgcaa tgtggggaga atacattgta   2160
gaatataagg tttggaagtc aaattatagt agaatgtgta tctaaatagt gactgctttg   2220
ccatttcatt caaacctgac aagtctatct ctaagagccg ccagatttcc atgtgtgcag   2280
tattataagt tatcatggaa ctatatggtg gacgcagacc ttgagaacaa cctaaattat   2340
ggggagaatt ttaaaatgtt aaactgtaat ttgtatttaa aaagcattcg tagtaaaggt   2400
gcccaagaaa ttattttggc catttattgt tttgtccttt tctttaaaga actgtttttt   2460
tttcttttgt ttacttttag accaaagatt gggttctaga aaatgcactt ggtatactaa   2520
gtattaaaac aaacaaaaag gaaagttgtt tcagttggca acactgccca ttcaattgaa   2580
tcagaagggg acaaaattaa cgattgcctt cagtttgtgt tgtgtatatt ttgatgtatg   2640
tggtcactaa caggtcactt ttattttttc taaatgtagt gaaatgttaa tacctattgt   2700
acttataggt aaaccttgca aatatgtaac ctgtgttgcg caaatgccgc ataaatttga   2760
gtgattgtta atgttgtctt aaaatttctt gattgtgata ctgtggtcat atgcccgtgt   2820
ttgtcactta caaaaatgtt tactatgaac acacagaaat aaaaaatagg ctaaattcat   2880
atatatcttg atacttttgt ctcttttatt aagtagagct aattttttaa agaccaatca   2940
acttataggg aattcaaagg ctttttcagc caaactaaaa tttaaactgc tcctttaatt   3000
```

```
tgaactgact ctaaaaatga aaatagtatt tttccctttg tgaacaaatt ttacaaggag   3060

cagcctattt aataaacact agctttaaac aaagtatagg cttttcagct gatacctgta   3120

agtttctgtg gatatacagc aaaaagagat ataatttaat tttctgtgca tagctcttta   3180

ccctgtgttt atttccaaat ccattaatag aatgccattt atatattttg tttcaggtat   3240

attgttaata gagcttggca aattataaat aaatatatgt atatggttag atagaagtga   3300

ctataatgca cacatatgta atatatatag acacacagag cccttcagtt caggtacaat   3360

ttgcgctatg aatgctgcaa acatttttgt ttaaatattt gtatttatac tttctaagtc   3420

agcatttatt tttgtggctg tttacccaca atgaaagagt tctaataaag atgtgctgaa   3480

gttgcaatat a                                                        3491
```

```
<210> SEQ ID NO 11
<211> LENGTH: 488
<212> TYPE: PRT
<213> ORGANISM: Homo sapiens

<400> SEQUENCE: 11

Leu Asp Met Gly Asp Arg Lys Glu Val Lys Met Ile Pro Lys Ser Ser
1               5                   10                  15

Phe Ser Ile Asn Ser Leu Val Pro Glu Ala Val Gln Asn Asp Asn His
            20                  25                  30

His Ala Ser His Gly His His Asn Ser His His Pro Gln His His His
        35                  40                  45

His His His His His His His His Pro Pro Pro Pro Ala Pro Gln Pro
    50                  55                  60

Pro Pro Pro Pro Gln Gln Gln Gln Pro Pro Pro Pro Pro Pro Pro Ala
65                  70                  75                  80

Pro Gln Pro Pro Gln Thr Arg Gly Ala Pro Ala Ala Asp Asp Asp Lys
                85                  90                  95

Gly Pro Gln Gln Leu Leu Leu Pro Pro Pro Pro Pro Pro Pro Pro Ala
            100                 105                 110

Ala Ala Leu Asp Gly Ala Lys Ala Asp Gly Leu Gly Gly Lys Gly Glu
        115                 120                 125

Pro Gly Gly Gly Pro Gly Glu Leu Ala Pro Val Gly Pro Asp Glu Lys
    130                 135                 140

Glu Lys Gly Ala Gly Ala Gly Gly Glu Glu Lys Lys Gly Ala Gly Glu
145                 150                 155                 160

Gly Gly Lys Asp Gly Glu Gly Gly Lys Glu Gly Glu Lys Lys Asn Gly
                165                 170                 175

Lys Tyr Glu Lys Pro Pro Phe Ser Tyr Asn Ala Leu Ile Met Met Ala
            180                 185                 190

Ile Arg Gln Ser Pro Glu Lys Arg Leu Thr Leu Asn Gly Ile Tyr Glu
        195                 200                 205

Phe Ile Met Lys Asn Phe Pro Tyr Tyr Arg Glu Asn Lys Gln Gly Trp
    210                 215                 220

Gln Asn Ser Ile Arg His Asn Leu Ser Leu Asn Lys Cys Phe Val Lys
225                 230                 235                 240

Val Pro Arg His Tyr Asp Asp Pro Gly Lys Gly Asn Tyr Trp Met Leu
                245                 250                 255

Asp Pro Ser Ser Asp Asp Val Phe Ile Gly Gly Thr Thr Gly Lys Leu
            260                 265                 270

Arg Arg Arg Ser Thr Thr Ser Arg Ala Lys Leu Ala Phe Lys Arg Gly
```

```
        275                 280                 285

Ala Arg Leu Thr Ser Thr Gly Leu Thr Phe Met Asp Arg Ala Gly Ser
    290                 295                 300

Leu Tyr Trp Pro Met Ser Pro Phe Leu Ser Leu His His Pro Arg Ala
305                 310                 315                 320

Ser Ser Thr Leu Ser Tyr Asn Gly Thr Thr Ser Ala Tyr Pro Ser His
                325                 330                 335

Pro Met Pro Tyr Ser Ser Val Leu Thr Gln Asn Ser Leu Gly Asn Asn
            340                 345                 350

His Ser Phe Ser Thr Ala Asn Gly Leu Ser Val Asp Arg Leu Val Asn
        355                 360                 365

Gly Glu Ile Pro Tyr Ala Thr His His Leu Thr Ala Ala Ala Leu Ala
    370                 375                 380

Ala Ser Val Pro Cys Gly Leu Ser Val Pro Cys Ser Gly Thr Tyr Ser
385                 390                 395                 400

Leu Asn Pro Cys Ser Val Asn Leu Leu Ala Gly Gln Thr Ser Tyr Phe
                405                 410                 415

Phe Pro His Val Pro His Pro Ser Met Thr Ser Gln Ser Ser Thr Ser
            420                 425                 430

Met Ser Ala Arg Ala Ala Ser Ser Ser Thr Ser Pro Gln Ala Pro Ser
        435                 440                 445

Thr Leu Pro Cys Glu Ser Leu Arg Pro Ser Leu Pro Ser Phe Thr Thr
    450                 455                 460

Gly Leu Ser Gly Gly Leu Ser Asp Tyr Phe Thr His Gln Asn Gln Gly
465                 470                 475                 480

Ser Ser Ser Asn Pro Leu Ile His
                485
```

<210> SEQ ID NO 12
<211> LENGTH: 6046
<212> TYPE: DNA
<213> ORGANISM: Homo sapiens

<400> SEQUENCE: 12

```
acagtgccaa taccatgaag aggagctcag acagctctta ccacatgata caagagccgg     60

ctggtggaag agtggggacc agaaagagaa tttgctgaag aggagaagga aaaaaaaaac    120

accaaaaaaa aaaataaaaa aatccacaca cacaaaaaaa cctgcgcgtg aggggggagg    180

aaaagcaggg ccttttaaaa aggcaatcac aacaactttt gctgccagga tgcccttgct    240

ttggctgaga ggatttctgt tggcaagttg ctggattata gtgaggagtt cccccacccc    300

aggatccgag gggcacagcg cggcccccga ctgtccgtcc tgtgcgctgg ccgccctccc    360

aaaggatgta cccaactctc agccagagat ggtggaggcc gtcaagaagc acattttaaa    420

catgctgcac ttgaagaaga gacccgatgt cacccagccg gtacccaagg cggcgcttct    480

gaacgcgatc agaaagcttc atgtgggcaa agtcggggag aacgggtatg tggagataga    540

ggatgacatt ggaaggaggg cagaaatgaa tgaacttatg gagcagacct cggagatcat    600

cacgtttgcc gagtcaggaa cagccaggaa gacgctgcac ttcgagattt ccaaggaagg    660

cagtgacctg tcagtggtgg agcgtgcaga agtctggctc ttcctaaaag tccccaaggc    720

caacaggacc aggaccaaag tcaccatccg cctcttccag cagcagaagc acccgcaggg    780

cagcttggac acaggggaag aggccgagga agtgggctta aagggggaga ggagtgaact    840

gttgctctct gaaaaagtag tagacgctcg gaagagcacc tggcatgtct tccctgtctc    900
```

-continued

```
cagcagcatc cagcggttgc tggaccaggg caagagctcc ctggacgttc ggattgcctg    960
tgagcagtgc caggagagtg gcgccagctt ggttctcctg ggcaagaaga agaagaaaga   1020
agaggagggg gaagggaaaa agaagggcgg aggtgaaggt ggggcaggag cagatgagga   1080
aaaggagcag tcgcacagac ctttcctcat gctgcaggcc cggcagtctg aagaccaccc   1140
tcatcgccgg cgtcggcggg gcttggagtg tgatggcaag gtcaacatct gctgtaagaa   1200
acagttcttt gtcagtttca aggacatcgg ctggaatgac tggatcattg ctccctctgg   1260
ctatcatgcc aactactgcg agggtgagtg cccgagccat atagcaggca cgtccgggtc   1320
ctcactgtcc ttccactcaa cagtcatcaa ccactaccgc atgcggggcc atagcccctt   1380
tgccaacctc aaatcgtgct gtgtgcccac caagctgaga cccatgtcca tgttgtacta   1440
tgatgatggt caaaacatca tcaaaaagga cattcagaac atgatcgtgg aggagtgtgg   1500
gtgctcatag agttgcccag cccaggggga aagggagcaa gagttgtcca gagaagacag   1560
tggcaaaatg aagaaatttt taaggtttct gagttaacca gaaaaataga aattaaaaac   1620
aaaacaaaaa aaaaaacaaa aaaaaacaaa agtaaattaa aaacaaaacc tgatgaaaca   1680
gatgaaggaa gatgtggaaa aaatccttag ccagggctca gagatgaagc agtgaaagag   1740
acaggaattg ggagggaaag ggagaatggt gtacccttta tttcttctga aatcacactg   1800
atgacatcag ttgtttaaac ggggtattgt cctttccccc cttgaggttc ccttgtgagc   1860
cttgaatcaa ccaatctagt ctgcagtagt gtggactaga acaacccaaa tagcatctag   1920
aaagccatga gtttgaaagg gcccatcaca ggcactttcc tacccaatta cccaggtcat   1980
aaggtatgtc tgtgtgacac ttatctctgt gtatatcagc atacacacac acacacacac   2040
acacacacac acacacaggc atttccacac attacatata tacacatact ggtaaaagaa   2100
caatcgtgtg caggtggtca cacttccttt ttctgtacca cttttgcaac aaaacaaaac   2160
aaacaacatt aaaaaattga gaacaagtat ggaaagaatg aaagatcaag gaaaaaagaa   2220
taccaagtta catttcgtta aggtgcttat gatcttagaa ctatgcaacc taataggttt   2280
gaaactgttt acctgagaga gaacaaaaag agagactttt ttgtattgga agtaatctga   2340
ttaattttta ttttcttcaa ggagagatac ttgaaaggaa tatgtttgtc catctgttgg   2400
atccaaacat ttctatattt tgtaaatgtt gttgttgttt ttttttaat cgtttactat   2460
ttgcactaca atggtgtttg acctgtctaa tccttattta acaagtattt tctttggttg   2520
ggggtggggg tggggtttaa gagctgcact taatgtgagc tataaaagaa ctgctacagc   2580
acacaaaata gctattttta ttattataat tataattatt attattattt tgtaccttaa   2640
aaaatagaca catacaccaa agacatttgt gtgagccttt aaacagtctg tctgtggttg   2700
gtatcattca ccatcaatga gtcaggggtt gggattcaag gttgagtagt gtggattgtg   2760
ttcaggctta aaagacctga gaagtttggt ttttgactcc ttttacatcc atgaaacagg   2820
acatttcata ctggatgtac agtagttgta cactgttgga tatcaagttc aatcaaattc   2880
atggaactac atgcttgtat gtgtatatat acattgcttg tgcatatgca tatctgtatg   2940
tatatataca tgtattgtac catgtccata cacattttaa gcacttcagg ctgtcatttt   3000
ttaatgttct taaagcaatg aatgtttgtg tgcaaaacac agtattttta agaaggatag   3060
gctatagttt ttgcttttac tctgaactag gtgggcgcat ttcaaaaatt cggatgggaa   3120
aaagcctgga aattccagtg aatattcagc aaggccctct ttcattgtac agggatcaaa   3180
tttcctcctc ttttttgtgc cccctcccac ttctacaagt tatcccctgt ggggaaaaca   3240
ggatgataat caaaactctg ggctgatgtt tttccaactt agtgtctatt ggaatcaatc   3300
```

-continued

```
ttaaatcaga agctttttca gaaaaataat atttaggcca gaattagagt tgagtgtatt   3360
ttttaaaaat gattaaggct tggttgtgag aaatattacc tgtaccagct gggaaaaata   3420
atgtcatcac taactaaaag ataattaatt tgagagaaag tgttaagaga gggagagtaa   3480
ggaagagaac agttaagagg aggcagaggt gagggcagta gtaaaaatct ctaaaatttt   3540
aatttacagc caaaattctt catgtgtaaa tttgtattga ttcagatgca gaaatgaaaa   3600
aaaaacacct ttgttttata aatatcaaag tacatgctta aagccaagtt tttatctagt   3660
ttattctagt acttagcttg cctggaatag ctaataaatt attcatgtat gtgcttttga   3720
aaatccagag ccctattttt acacacttgt gtgaagttgg caaacatttt gaaaaatgga   3780
aaaaagtttc taataattgg gaacaattac attaattaat attttgtaaa atattgaagc   3840
ttttagccct atgtcaattt gtagattaaa ataaattaat tataggaaag gaagataaca   3900
gtgagaaacc aaacattaca aaaggtggtt tagctctcct tgaaaaatat actaagttgg   3960
tatactataa cacttggcta tatgtaggca atgtcactac tgggcaaata cacttactgt   4020
gttctagagg cagccctttc ttatgcagaa aatacaatac gcactgcatg agaagcttga   4080
gagtggattc taatccaggt ctgtcgacct tggatatcat gcatgtggga aggtgggtgt   4140
ggtgagaaaa gttttaaggc aagagtagat ggccatgttc aactttacaa aatttcttgg   4200
aaaactggca gtattttgaa ctgcatcttc tttggtaccg gaacctgcag aaacagtgtg   4260
agaaattaag tcctggttca ctgcgcagta gcaaagatgg tcaaggccat ggaaaaagca   4320
gaaatttacc aagaaagctg atacccatgt atagttccca ctcatctcaa atacatctgc   4380
tatcttttta agctaagtcc tagacatatc ggggataaca tgggggttga ttagtgacca   4440
cagttatcag aagcagagaa atgtaattcc atattttatt tgaaacttat tccatatttt   4500
aattggatat tgagtgattg ggttatcaaa cacccacaaa ctttaatttt gttaaattta   4560
tatggctttg aaatagaagt ataagttgct accatttttt gataacattg aaagatagta   4620
ttttaccatc tttaatcatc ttggaaaata caagtcctgt gaacaaccac tctttcacct   4680
agcagcatga ggccaaaagt aaaggcttta aattataaca tatgggattc ttagtagtat   4740
gttttttttct tgaaactcag tggctctatc taaccttact atctcctcac tctttctcta   4800
agactaaact ctaggctctt aaaaatctgc ccacaccaat cttagaagct ctgaaaagaa   4860
tttgtcttta aatatctttt aatagtaaca tgtattttat ggaccaaatt gacattttcg   4920
actatttttt ccaaaaaagt caggtgaatt tcagcacact gagttgggaa tttcttatcc   4980
cagaagacca accaatttca tatttattta agattgattc catactccgt tttcaaggag   5040
aatccctgca gtctccttaa aggtagaaca aatactttct atttttttt caccattgtg   5100
ggattggact ttaagaggtg actctaaaaa aacagagaac aaatatgtct cagttgtatt   5160
aagcacggac ccatattatc atattcactt aaaaaaatga tttcctgtgc accttttggc   5220
aacttctctt ttcaatgtag ggaaaaactt agtcaccctg aaaacccaca aaataaataa   5280
aacttgtaga tgtgggcaga aggtttgggg gtggacattg tatgtgttta aattaaaccc   5340
tgtatcactg agaagctgtt gtatgggtca gagaaaatga atgcttagaa gctgttcaca   5400
tcttcaagag cagaagcaaa ccacatgtct cagctatatt attatttatt ttttatgcat   5460
aaagtgaatc atttcttctg tattaatttc caaagggttt taccctctat ttaaatgctt   5520
tgaaaaacag tgcattgaca atgggttgat atttttcttt aaaagaaaaa tataattatg   5580
aaagccaaga taatctgaag cctgttttat tttaaaactt tttatgttct gtggttgatg   5640
```

```
ttgtttgttt gtttgtttct attttgttgg ttttttactt tgttttttgt tttgttttgt   5700

tttgttttgc atactacatg cagttcttta accaatgtct gtttggctaa tgtaattaaa   5760

gttgttaatt tatatgagtg catttcaact atgtcaatgg tttcttaata tttattgtgt   5820

agaagtactg gtaatttttt tatttacaat atgtttaaag agataacagt ttgatatgtt   5880

ttcatgtgtt tatagcagaa gttatttatt tctatggcat tccagcggat attttggtgt   5940

ttgcgaggca tgcagtcaat attttgtaca gttagtggac agtattcagc aacgcctgat   6000

agcttctttg gccttatgtt aaataaaaag acctgtttgg gatgta                  6046


<210> SEQ ID NO 13
<211> LENGTH: 426
<212> TYPE: PRT
<213> ORGANISM: Homo sapiens

<400> SEQUENCE: 13

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
            260                 265                 270

Gly Gly Gly Glu Gly Gly Ala Gly Ala Asp Glu Glu Lys Glu Gln Ser
        275                 280                 285

His Arg Pro Phe Leu Met Leu Gln Ala Arg Gln Ser Glu Asp His Pro
    290                 295                 300
```

His Arg Arg Arg Arg Arg Gly Leu Glu Cys Asp Gly Lys Val Asn Ile
305 310 315 320

Cys Cys Lys Lys Gln Phe Phe Val Ser Phe Lys Asp Ile Gly Trp Asn
325 330 335

Asp Trp Ile Ile Ala Pro Ser Gly Tyr His Ala Asn Tyr Cys Glu Gly
340 345 350

Glu Cys Pro Ser His Ile Ala Gly Thr Ser Gly Ser Ser Leu Ser Phe
355 360 365

His Ser Thr Val Ile Asn His Tyr Arg Met Arg Gly His Ser Pro Phe
370 375 380

Ala Asn Leu Lys Ser Cys Cys Val Pro Thr Lys Leu Arg Pro Met Ser
385 390 395 400

Met Leu Tyr Tyr Asp Asp Gly Gln Asn Ile Ile Lys Lys Asp Ile Gln
405 410 415

Asn Met Ile Val Glu Glu Cys Gly Cys Ser
420 425

<210> SEQ ID NO 14
<211> LENGTH: 2549
<212> TYPE: DNA
<213> ORGANISM: Homo sapiens

<400> SEQUENCE: 14
gtccattgaa tcgcgcgggc ggccggcggc gagcgcgggg ctgcgccggg atcgctgcgc 60
cctccgccgc tggcctctgc gacgcgcgcc gctcgcccga gccacccgcc gccgcgccgg 120
ctccccgcgc cgctgcgctc ctcgccccgc gcctgccccc aggatggtcc gcgcgaggca 180
ccagccgggt gggctttgcc tcctgctgct gctgctctgc cagttcatgg aggaccgcag 240
tgcccaggct gggaactgct ggctccgtca agcgaagaac ggccgctgcc aggtcctgta 300
caagaccgaa ctgagcaagg aggagtgctg cagcaccggc cggctgagca cctcgtggac 360
cgaggaggac gtgaatgaca acacactctt caagtggatg attttcaacg gggggcgccc 420
caactgcatc ccctgtaaag aaacgtgtga gaacgtggac tgtggacctg ggaaaaaatg 480
ccgaatgaac aagaagaaca aaccccgctg cgtctgcgcc ccggattgtt ccaacatcac 540
ctggaagggt ccagtctgcg ggctggatgg gaaaacctac cgcaatgaat gtgcactcct 600
aaaggcaaga tgtaaagagc agccagaact ggaagtccag taccaaggca gatgtaaaaa 660
gacttgtcgg gatgttttct gtccaggcag ctccacatgt gtggtggacc agaccaataa 720
tgcctactgt gtgacctgta atcggatttg cccagagcct gcttcctctg agcaatatct 780
ctgtgggaat gatggagtca cctactccag tgcctgccac ctgagaaagg ctacctgcct 840
gctgggcaga tctattggat tagcctatga gggaaagtgt atcaaagcaa agtcctgtga 900
agatatccag tgcactggtg ggaaaaaatg tttatgggat ttcaaggttg ggagaggccg 960
gtgttccctc tgtgatgagc tgtgccctga cagtaagtcg gatgagcctg tctgtgccag 1020
tgacaatgcc acttatgcca gcgagtgtgc catgaaggaa gctgcctgct cctcaggtgt 1080
gctactggaa gtaaagcact ccggatcttg caactgaatc tgcccgtaaa acctgagcca 1140
ttgattcttc agaactttct gcagtttttg acttcataga ttatgcttta aaaaaatttt 1200
tttaacttat tgcataacag cagatgccaa aaacaaaaaa agcatctcac tgcaagtcac 1260
ataaaaatgc aacgctgtaa tatggctgta tcagagggct ttgaaaacat acactgagct 1320
gcttctgcgc tgttgttgtc cgtatttaaa caacagctcc cctgtattcc cccatctagc 1380
catttcggaa gacaccgagg aagaggagga agatgaagac caggactaca gctttcctat 1440

```
atcttctatt ctagagtggt aaactctcta taagtgttca gtgttgacat agcctttgtg   1500

caaaaaaaaa aaaaaaaaaa aagaaaaaga aaaaaagaaa aatatattgt ccatactgta   1560

aataagtgta tgcttattta tttgggggga aaactataca ttaaaggacc tttgtcctaa   1620

agctctctcc caggccacct tgttactcat tggacacgga gaggcattca ttgtgaggtc   1680

tactggatga ggcccatagt tgagacttgt agacatttat ttatactgtg tcatgtttta   1740

taatttatac ataaaatgtc tggttgactg tataccttgt ttttgaagaa atttattcgt   1800

gaaaggaaga gcagttgtta tttattgtga ggtctcttgc ttgtaaagta aaagcttttt   1860

ttccttgtaa accatttaag tccattcctt actattcact cactcatctg tctcccttca   1920

tttcactgtt agactctttt ccactttcaa caaacttgca tgtcagtttc tgtcatgttt   1980

atttattgga ttctctgctg cctgatctgt acatacatga tccctcgggt tttgtttaca   2040

aggaaccttg actgaccaaa aggcattata actctgactc aaatacaagg tacagaagat   2100

aagcatcttt gaggaaactc ctacttcagt tcttttgtta tgatgaagac atttgtgaga   2160

gaggagatga ttagaattct agtaatgtac ttttaagatg ttacagatac aaagaaatga   2220

tgtgggtgtc aggagactaa aggatgttga aggctacaca ttcaaccttt tgttaggtgt   2280

ttcctttaag ctactcagct gtacctttta aattagttct ttttcaacca gtatatcact   2340

aaaagttata tcaaagcttt atcagttcaa gtttcttgct tttcataata ctttttttctg   2400

atgcaatttt atattttcaa acatggcaag ttaaaatata aattcattta aatatatagt   2460

tttgtacttt tctaccatgt aaatgtgcaa tgtatataaa agttataatg tgtatttgta   2520

aataaatgat gagtgaaaaa ataaaaaaa                                     2549
```

<210> SEQ ID NO 15
<211> LENGTH: 317
<212> TYPE: PRT
<213> ORGANISM: Homo sapiens

<400> SEQUENCE: 15

```
Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175
```

```
Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn
305                 310                 315


<210> SEQ ID NO 16
<211> LENGTH: 270
<212> TYPE: DNA
<213> ORGANISM: Artificial Sequence
<220> FEATURE:
<223> OTHER INFORMATION: Synthetic Polynucleotide

<400> SEQUENCE: 16

ccacgttctg cttcactctc cccatctccc ccccctcccc acccccaatt ttgtatttat      60

ttatttttta attattttgt gcagcgatgg gggcgggggg gggggggggg cgcgcgccag     120

gcggggcggg gcggggcgag gggcggggcg gggcgaggcg gagaggtgcg gcggcagcca     180

atcagagcgg cgcgctccga aagtttcctt ttatggcgag gcggcggcgg cggcggccct     240

ataaaaagcg aagcgcgcgg cgggcgggag                                      270


<210> SEQ ID NO 17
<211> LENGTH: 280
<212> TYPE: DNA
<213> ORGANISM: Artificial Sequence
<220> FEATURE:
<223> OTHER INFORMATION: Synthetic Polynucleotide

<400> SEQUENCE: 17

cgttacataa cttacggtaa atggcccgcc tggctgaccg cccaacgacc cccgcccatt      60

gacgtcaata atgacgtatg ttcccatagt aacgccaata gggactttcc attgacgtca     120

atgggtggag tatttacggt aaactgccca cttggcagta catcaagtgt atcatatgcc     180

aagtacgccc cctattgacg tcaatgacgg taaatggccc gcctggcatt atgcccagta     240

catgacctta tgggactttc ctacttggca gtacatctac                           280


<210> SEQ ID NO 18
<211> LENGTH: 1629
<212> TYPE: DNA
<213> ORGANISM: Artificial Sequence
<220> FEATURE:
<223> OTHER INFORMATION: Synthetic Polynucleotide

<400> SEQUENCE: 18

tttggaggcc gccctgtccc ccataacctg cccacctctc tgccccattc ccacagctca      60
```

ctgcatttg tccctgctgc cagtcgtgtg ccatgggctc tcctgtgctc ccccggggtc 120
tcatttcccc atccgtgtag ggctgacgcc actggccccg cccagcctgg gaggatggag 180 agggggact tgaggagtgg ccagtactgg gtttcggcag caggtgcaaa tcccaggtgg 240
ggactgtgtt ccagggactc ctggactcct gttaggccag caggctaagg ggcagacggc 300
atcctggggt cttcctggga cagggtcgtc gggtctgagg ggacccaggc cctagcagaa 360
gctgactcct gtcacggtca cttcccagcg gtgctcagcc cgcctgacgg aagcagctgg 420
gcagtggggc ctgtgaccag caggcggcgc tggcgagcta tagcgcccct ttgggccccc 480
accccacctt ctgggcagct tccctgcaga caccccagtt atgggggcta gggacccaaa 540
agagacatcc ttctgccacc cagagctgcc ctggcgaggt gcactatggg gccgccgaca 600
gctgcgtggc tgccgagggc ggaaaggaga aactgtcatg tcccgatagg gccgcgcgag 660
gtctccatcc tcgacaacgc taataacaaa gacgtgtgct cctctttgct tggttccccc 720
cactccttta aatcacagat ttcacttcag tttatctgtg tcgctgtcac acgtggggtg 780
gctcccagtc agctggtttg gcaaagtttc tggatgatta cggaataaca tgtgtcccca 840
acccgcagag caggttgtgg gggcaatgtt gcattgacca gcgtcagaga acacacatca 900
gaggcaaggg tgggtgtgca ggagggagaa ggcgcagaag gcagggcttt agctcagcac 960
tctccctcct gccatgctct gcctgaccgt tccctctctg agtcccaaac agccaggtag 1020
aggaggaaga aatggggctg agaccccagc acatcagtga ttaagtcagg atcaggtgcg 1080
gtttcctgct caggtgctga gacagcaggc ggtgtcctgc aaacaacagg aggcacctga 1140
agctagcctg gggggcccac gcccaggtgc ggtgcattca gcagcacagc cagagacaga 1200
ccccaatgac cccgcctccc tgtcggcagc cagtgctctg cacagagccc tgagcagcct 1260
ctggacatta gtcccagccc cagcacggcc cgtcccccac gctgatgtca ccgcacccag 1320
accttggagg ccccctccgg ctccgcctcc tgggagaagg ctctggagtg aggaggggag 1380
ggcagcagtg ctggctggac agctgctctg ggcaggagag agagggagag acaagagaca 1440
cacacagaga gacggcgagg aagggaaaga cccagaggga cgcctagaac gagacttgga 1500
gccagacaga ggaagagggg acgtgtgttt gcagactggc tgggcccgtg acccagcttc 1560
ctgagtcctc cgtgcaggtg gcagctgtac caggctggca ggtcactgag agtgggcagc 1620
tgggcccca 1629

<210> SEQ ID NO 19
<211> LENGTH: 528
<212> TYPE: DNA
<213> ORGANISM: Homo Sapiens

<400> SEQUENCE: 19
atctctctcg ggtggagtct tctgacagct ggtgcgcctg cccgggaaca tcctcctgga 60
ctcaatcatg gcttgtggtc tggtcgccag caacctgaat ctcaaacctg gagagtgcct 120
tcgagtgcga ggcgaggtgg ctcctgacgc taagagcttc gtgctgaacc tgggcaaaga 180
cagcaacaac ctgtgcctgc acttcaaccc tcgcttcaac gcccacggcg acgccaacac 240
catcgtgtgc aacagcaagg acggcggggc ctgggggacc gagcagcggg aggctgtctt 300
tcccttccag cctggaagtg ttgcagaggt gtgcatcacc ttcgaccagg ccaacctgac 360
cgtcaagctg ccagatggat acgaattcaa gttccccaac cgcctcaacc tggaggccat 420
caactacatg gcagctgacg gtgacttcaa gatcaaatgt gtggcctttg actgaaatca 480
gccagcccat ggcccccaat aaaggcagct gcctctgctc cctctgaa 528

<210> SEQ ID NO 20
<211> LENGTH: 135
<212> TYPE: PRT
<213> ORGANISM: Homo Sapiens

<400> SEQUENCE: 20

Met Ala Cys Gly Leu Val Ala Ser Asn Leu Asn Leu Lys Pro Gly Glu
1 5 10 15

Cys Leu Arg Val Arg Gly Glu Val Ala Pro Asp Ala Lys Ser Phe Val
20 25 30

Leu Asn Leu Gly Lys Asp Ser Asn Asn Leu Cys Leu His Phe Asn Pro
35 40 45

Arg Phe Asn Ala His Gly Asp Ala Asn Thr Ile Val Cys Asn Ser Lys
50 55 60

Asp Gly Gly Ala Trp Gly Thr Glu Gln Arg Glu Ala Val Phe Pro Phe
65 70 75 80

Gln Pro Gly Ser Val Ala Glu Val Cys Ile Thr Phe Asp Gln Ala Asn
85 90 95

Leu Thr Val Lys Leu Pro Asp Gly Tyr Glu Phe Lys Phe Pro Asn Arg
100 105 110

Leu Asn Leu Glu Ala Ile Asn Tyr Met Ala Ala Asp Gly Asp Phe Lys
115 120 125

Ile Lys Cys Val Ala Phe Asp
130 135

<210> SEQ ID NO 21
<211> LENGTH: 943
<212> TYPE: DNA
<213> ORGANISM: Homo Sapiens

<400> SEQUENCE: 21
gcccgcagca cctcctcgcc agcagccgtc cggagccagc caacgagcgg aaaatggcag 60
acaatttttc gctccatgat gcgttatctg ggtctggaaa cccaaaccct caaggatggc 120
ctggcgcatg gggaaccag cctgctgggg caggggggcta cccaggggct tcctatcctg 180
gggcctaccc cgggcaggca cccccagggg cttatcctgg acaggcacct ccaggcgcct 240
accctggagc acctggagct tatcccggag cacctgcacc tggagtctac ccagggccac 300
ccagcggccc tggggcctac ccatcttctg gacagccaag tgccaccgga gcctaccctg 360
ccactggccc ctatggcgcc cctgctgggc cactgattgt gccttataac ctgcctttgc 420
ctgggggagt ggtgcctcgc atgctgataa caattctggg cacggtgaag cccaatgcaa 480
acagaattgc tttagatttc caaagaggga atgatgttgc cttccacttt aacccacgct 540
tcaatgagaa caacaggaga gtcattgttt gcaatacaaa gctggataat aactggggaa 600
gggaagaaag acagtcggtt ttcccatttg aaagtgggaa accattcaaa atacaagtac 660
tggttgaacc tgaccacttc aaggttgcag tgaatgatgc tcacttgttg cagtacaatc 720
atcgggttaa aaaactcaat gaaatcagca aactgggaat ttctggtgac atagacctca 780
ccagtgcttc atataccatg atataatctg aaaggggcag attaaaaaaa aaaaaagaat 840
ctaaacctta catgtgtaaa ggtttcatgt tcactgtgag tgaaaatttt tacattcatc 900
aatatccctc ttgtaagtca tctacttaat aaatattaca gtg 943

<210> SEQ ID NO 22

-continued

```
<211> LENGTH: 250
<212> TYPE: PRT
<213> ORGANISM: Homo Sapiens

<400> SEQUENCE: 22

Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250
```